(12) United States Patent
Bradbury et al.

(10) Patent No.: US 11,660,354 B2
(45) Date of Patent: May 30, 2023

(54) INHIBITOR-FUNCTIONALIZED ULTRASMALL NANOPARTICLES AND METHODS THEREOF

(71) Applicants: Memorial Sloan Kettering Cancer Center, New York, NY (US); Cornell University, Ithaca, NY (US); The Curators of the University of Missouri, Columbia, MO (US)

(72) Inventors: Michelle S. Bradbury, New York, NY (US); Thomas P. Quinn, Columbia, MO (US); Barney Yoo, New York, NY (US); Wolfgang Weber, Larchmont, NY (US); Karim Touijer, New York, NY (US); Howard Scher, Tenafly, NJ (US); Kai Ma, Ithaca, NY (US); Ulrich Wiesner, Ithaca, NY (US)

(73) Assignees: Memorial Sloan Kettering Cancer Center, New York, NY (US); Cornell University, Ithaca, NY (US); The Curators of the University of Missouri, Columbia, MO (US)

( * ) Notice: Subject to any disclaimer, the term of this patent is extended or adjusted under 35 U.S.C. 154(b) by 8 days.

(21) Appl. No.: 16/463,865

(22) PCT Filed: Nov. 29, 2017

(86) PCT No.: PCT/US2017/063641
§ 371 (c)(1),
(2) Date: May 24, 2019

(87) PCT Pub. No.: WO2018/102372
PCT Pub. Date: Jun. 7, 2018

(65) Prior Publication Data
US 2019/0282712 A1 Sep. 19, 2019

Related U.S. Application Data

(60) Provisional application No. 62/427,845, filed on Nov. 30, 2016.

(51) Int. Cl.
| A61K 49/00 | (2006.01) |
|---|---|
| A61K 51/08 | (2006.01) |
| A61K 51/12 | (2006.01) |
| C07K 7/02 | (2006.01) |
| C07K 17/00 | (2006.01) |
| G01N 33/574 | (2006.01) |

(52) U.S. Cl.
CPC ...... *A61K 49/0067* (2013.01); *A61K 49/0002* (2013.01); *A61K 49/0056* (2013.01); *A61K 51/08* (2013.01); *A61K 51/088* (2013.01); *A61K 51/1244* (2013.01); *C07K 7/02* (2013.01); *C07K 17/00* (2013.01); *G01N 33/57434* (2013.01)

(58) Field of Classification Search
CPC ............ A61K 49/0067; A61K 49/0002; A61K 49/0056; A61K 51/088; A61K 51/1244; C07K 7/02
See application file for complete search history.

(56) References Cited

U.S. PATENT DOCUMENTS 5,686,410 A 11/1997 Albert et al.

FOREIGN PATENT DOCUMENTS

| WO | WO-2006/110745 A2 | 10/2006 |
|---|---|---|
| WO | WO-2014/127365 A1 | 8/2014 |
| WO | WO-2016/164578 A1 | 10/2016 |
| WO | WO-2016/176462 A1 | 11/2016 |
| WO | WO-2018/102372 A1 | 6/2018 |

OTHER PUBLICATIONS

Over Kratochwil et al., Semin Nucl Med 46:405-418, 2016. (Year: 2016).*
Banerjee, S.R. et al., Preclinical Comparative Study of 68Ga-Labeled DOTA, NOTA, and HBED-CC Chelated Radiotracers for Targeting PSMA, Biocoryugate Chem., 27(6):1447-1455, (2016).
Benesová, M et al., Preclinical Evaluation of a Tailor-Made DOTA-Conjugated PSMA Inhibitor with Optimized Linker Moiety for Imaging and Endoradiotherapy of Prostate Cancer, J. Nucl Med, 56(6):914-920, (2015).
Moon, S.H., et al., Development of a complementary PET/MR dual-modal imaging probe for targeting prostate-specific membrane antigen (PSMA), Nanomedicine: Nanotechnology, Biology and Medicine, 4(12):871-879, (2016).
Anderson, C. J. and Welch, M. J., Radiometal-Labeled Agents (Non-Technetium) for Diagnostic Imaging, Chem. Rev., 99:2219-2234 (1999).
Anderson, C.J. and Ferdani, R., Copper-64 Radiopharmaceuticals for PET Imaging of Cancer: Advances in Preclinical and Clinical Research, Cancer Biother Radiopharm, 24(4):379-393 (2009).
Bacia, K. et al., Fluorescence cross-correlation spectroscopy in living cells, Nature Methods, 3(2):83-89 (2006).
Bandari, R.P. et al., Synthesis and biological evaluation of copper-64 radiolabeled [DUPA-6-Ahx-(NODAGA)-5-Ava-BBN(7-14)NH2], a novel bivalent targeting vector having affinity for two distinct biomarkers (GRPr/PSMA) of prostate cancer, Nucl Med Biol, 41(4):355-63 (2014).
Banerjee, S. et al., Preclinical Comparative Study of 68Ga-Labeled DOTA, NOTA, and HBED-CC Chelated Radiotracers for Targeting PSMA, Bioconjugate Chemistry, 27(6):1447-1455 (2016).
Banerjee, S. R. et al., Synthesis and evaluation of technetium-99m and rhenium-labeled inhibitors of the prostate-specific membrane antigen (PSMA), Journal of Medicinal Chemistry, American Chemical Society, 51(15):4504-4517 (2008).

(Continued)

*Primary Examiner* — Robert S Cabral
(74) *Attorney, Agent, or Firm* — Choate, Hall & Stewart LLP; William R. Haulbrook; Margo R. Monroe

(57) ABSTRACT

Described herein are novel conjugates containing an inhibitor (e.g., a PSMA inhibitor, e.g., a gastrin-releasing peptide receptor inhibitor) and metal chelator that are covalently attached to a macromolecule (e.g., a nanoparticle, a polymer, a protein). Such conjugates exhibit distinct properties over the free, unbound inhibitor/chelator construct.

25 Claims, 26 Drawing Sheets

Specification includes a Sequence Listing.

(56) References Cited

OTHER PUBLICATIONS

Banerjee, S.R. et al., 68Ga-Labeled Inhibitors of Prostate-Specific Membrane antigen (PSMA) for Imaging Prostate Cancer, J Med Chem, 53(14):5333-5341 (2010).
Barve, A. et al., Prostate Cancer Relevant Antigens and Enzymes for Targeted Drug Delivery, J Control Release, 0:118-132 (2014).
Baum, R.P. et al., 177Lu-Labeled Prostate-Specific Membrane Antigen Radioligand Therapy of Metastatic Castration-Resistant Prostate Cancer: Safety and Efficacy, J Nucl Med, 57(7):1006-1013 (2016).
Benesova, M. et al., Linker Modification Strategies To Control the Prostate-Specific Membrane Antigen (PSMA)-Targeting and Pharmacokinetic Properties of DOTA-Conjugated PSMA Inhibitors, J. Med. Chem., 59:1761-1775 (2016).
Benezra, M. et al., Multimodal silica nanoparticles are effective cancer-targeted probes in a model of human melanoma, J Clin Invest, 121(7):2768-2780 (2011).
Benezra, M. et al., Serial monitoring of human systemic and xenograft models of leukemia using a novel vascular disrupting agent, Leukemia, 26(8):1771-1778 (2012).
Benezra, M. et al., Ultrasmall integrin-targeted silica nanoparticles modulate signaling events and cellular processes in a concentration-dependent manner, Small, 11 (14):1721-1732 (2015).
Bradbury, M.S. et al., Clinically-translated silica nanoparticles as dual-modality cancer-targeted probes for image-guided surgery and interventions, Integr Biol (Camb), 5(1):74-86 (2013).
Chang, A.J., et al., "High-Risk" Prostate Cancer: Classification and Therapy, Nat Rev Clin Oncol, 11(6):308-323 (2014).
Chapman, S. et al., Nanoparticles for cancer imaging: The good, the bad, and the promise, Nano Today, 8(5):454-460 (2013).
Chen, F. et al., Cancer-Targeting Ultrasmall Silica Nanoparticles for Clinical Translation: Physicochemical Structure and Biological Property Correlations, Chem. Mater., 29:8766-8779 (2017).
Chen, F., et al., Target-or-Clear Zirconium-89 Labeled Silica Nanoparticles for Enhanced Cancer-Directed Uptake in Melanoma: A Comparison of Radiolabeling Strategies, Chem. Mater., 29:8269-8281 (2017).
Chen, J. et al., Evaluation of an (111)In-DOTA-Rhenium Cyclized alpha-MSH Analog: A Novel Cyclic-Peptide Analog with Improved Tumor-Targeting Properties, J Nucl Med, 42(12):1847-1855 (2001).
Chen, J. et al., Melanoma-Targeting Properties of (99m)Technetium-labeled Cyclic alpha-Melanocyte-stimulating Hormone Peptide Analogues, Cancer Res, 60(20):5649-5658 (2000).
Cousins, A. et al., Clinical relevance of novel imaging technologies for sentinel lymph node identificaiton and staging, Biotechnology Advances, 21:269-279 (2014).
Crehange, G. et al., Management of prostate cancer patients with lymph node involvement: A rapidly evolving paradigm, Cancer Treat Rev, 38(8):956-967 (2012).
Datta, K. et al., Mechanism of lymph node metastasis in prostate cancer, Future Oncol, 6(5):823-836 (2010).
De Boer, E. et al., Optical innovations in surgery, BJS, 102:e56-e72 (2015).
Deri, M. et al., PET imaging with (8)(9)Zr: From Radiochemistry to the Clinic, Nucl Med Biol, 40(1):3-14 (2013).
Dumont, R.A. et al., Targeted Radiotherapy of Prostate Cancer with a Gastrin-Releasing Peptide Receptor Antagonist Is Effective as Monotherapy and in Combination with Rapamycin, J Nucl Med, 54(5):762-769 (2013).
Eder, M. et al., Novel Preclinical and Radiopharmaceutical Aspects of [68GA]GA-PSMA-HBED-CC: A New PET Tracer for Imaging of Prostate Cancer, Pharmaceuticals (Basel), 7(7):779-796 (2014).
Eder, M. et al., Preclinical Evaluation of a Bispecific Low-Molecular Heterodimer Targeting Both PSMA and GRPR for Improved PET Imaging and Therapy of Prostate Cancer, Prostate, 74(6):659-668 (2014).
Eiber, M. et al., Simultaneous $^{68}$Ga-PSMA HBED-CC PET/MRI Improves the Localizaton of Primary Prostate Cancer, European Urology, 79:829-836 (2016).
Ellwood-Yen, K. et al., Myc-driven murine prostate cancer shares molecular features with human prostate tumors, Cancer Cell, 4(3):223-238 (2003).
Epstein, J. I. et al., Prediction of Progression Following Radical Prostatectomy A Multivariate Analysis of 721 Men with Long-term Follow-up, The American Journal of Surgical Pathology, 20(3):286-292 (1996).
Eschmann, S. M. et al., Comparison of $^{11}$C-choline-PET/CT and whole body-MRI for staging of prostate caner, Nuklearmedizin, 46:161-168 (2007).
Evans, M.J. et al., Noninvasive measurement of androgen receptor signaling with a positron-emitting radiopharmaceutical that targets prostate-specific membrane antigen, Proc Natl Acad Sci U S A, 108(23):9578-9582 (2011).
Fortuin, A. et al., Molecular and Functional Imaging for Detection of Lymph Node Metastases in Prostate Cancer, Int J Mol Sci, 14(7):13842-13857 (2013).
Foster, B.A. et al., Characterization of Prostatic Epithelial Cell Lines Derived from Transgenic Adenocarcinoma of the Mouse Prostate (TRAMP) Model, Cancer Res, 57(16):3325-3330 (1997).
Gao, D. et al., Organoid Cultures Derived from Patients with Advanced Prostate Cancer, Cell, 159(1):176-187 (2014).
Gingrich, J.R. and Greenberg, N.M., A Transgenic Mouse Prostate Cancer Model, Toxicol Pathol, 24(4):502-504 (1996).
Gonen, M., PhD, et al., Statistical Issues in Analysis of Diagnostic Imaging Eperiments iwth Multiple Observations per Patient, Radiology, Statistical Issues in Diagnostic Imaging, 221(3):763-767(2001).
Goulding, H. et al., A New Immunohistochemical Antibody for the Assessment of Estrogen Receptor Status on Routine Formalin-Fixed Tissue Samples, Human Pathology, 26(3):291-294 (1995).
Greenberg, N. et al., Prostate cancer in a transgenic mouse, Proc Natl Acad Sci U S A, 92(8):3439-3443 (1995).
Guo, H. et al., Gallium-67-Labeled Lactam Bridge-Cyclized alpha-Melanocyte Stimulating Hormone Peptide for Primary and Metastatic Melanoma Imaging, Bioconjug Chem, 20(12):2356-2363 (2009).
Han, M. and Partin, A.W., Current Clinical Applications of the (111)In-capromab Pendetide Scan (ProstaScint® Scan, Cyt-356), Rev Urol, 3(4):165-171 (2001).
Harisinghani, M. G. et al., Noninvasive Detection of Clinically Occult Lymph-Node Metastases in Prostate Cancer, N Engl J Med, 348(25):2491-2499 (2003).
Heller, G., Power Calculations for Preclinical Studies Using a K-Sample Rank Test and the Lehmann Alternative Hypothesis, Stat Med, 25(15):2543-2553 (2006).
Hillier, S.M. et al., 99mTc-Labeled Small-Molecule Inhibitors of Prostate-Specific Membrane Antigen for Molecular Imaging of Prostate Cancer, J Nucl Med, 54(8):1369-1376 (2013).
Holland, J.P. et al., 89Zr-DFO-J591 for ImmunoPET of Prostate-Specific Membrane Antigen Expression In Vivo, J Nucl Med, 51 (8):1293-1300 (2010).
Huss, W. J. et al., Autochthonous mouse models for prostate cancer: past, present and future, Cancer Biology, 11:245-259 (2001).
International Search Report, PCT/US2017/063641 (Inhibitor-Functionalized Ultrasmall Nanoparticles and Methods Thereof, filed Nov. 29, 2017), issued by ISA/EPO, 5 pages, dated Mar. 6, 2018.
Keshari, K.R. et al., Hyperpolarized [1-13C]dehydroascorbate MR Spectroscopy in a Murine Model of Prostate Cancer: Comparison with 18F-FDG PET, J Nucl Med, 54(6):922-928 (2013).
Kim, S.E. et al., Ultrasmall nanoparticles induce ferroptosis in nutrient-deprived cancer cells and suppress tumour growth, Nat Nanotechnol, 11(11):977-985 (2016).
Kobayashi, H. et al., Multiplexed imaging in cancer diagnosis: applications and future advances, The Lancet Oncology, 11(6):589-595 (2010).
Kratochwil, C. et al., 225AC-PSMA-617 for PSMA-Targeted alpha-Radiation Therapy of Metastatic Castration-Resistant Prostate Cancer, J Nucl Med, 57(12):1941-1944 (2016).
Kratochwil, C. et al., PSMA-Targeted Radionuclide Therapy of Metastatic Castration-Resistant Prostate Cancer with 177Lu-Labeled PSMA-617, J Nucl Med, 57(8):1170-1176 (2016).

(56) References Cited

OTHER PUBLICATIONS

Larson, D. R. et al., Silica Nanoparticle Architecture Determines Radiative Properties of Encapsulated Fluorophores, Chem. Mater., 20:2677-2684 (2008).
Longmire, M. et al., Multicolor in vivo targeted imaging to guide real-time surgery of HER2-positive micrometastases in a two-tumor coincident model of ovarian cancer, Cancer Sci, 100(6):1099-1104 (2009).
Lucarelli, R.T. et al., New Approaches to Lymphatic Imaging, Lymphat Research and Biology, 7(4):205-214 (2009).
Ma, K. and Wiesner, U., Modular and Orthogonal Post-PEGylation Surface Modifications by Insertion Enabling Penta-Functional Ultrasmall Organic-Silica Hybrid Nanoparticles, Chem. Mater., 29:6840-6855 (2017).
Ma, K. et al., Control of Ultrasmall Sub-10 nm Ligand-Functionalized Fluorescent Core?Shell Silica Nanoparticle Growth in Water, Chem. Mater., 27:4119-4133 (2015).
Ma, K. et al., Elucidating the Mechanism of Silica Nanoparticle PEGylation Processes Using Fluorescence Correlation Spectroscopies, Chem Mater, 28(5):1537-1545 (2016).
Mansi, R. et al., Bombesin-Targeted PET of Prostate Cancer, J Nucl Med, 57(Suppl 3):67s-72s (2016).
Mansi, R. et al., Development of a potent DOTA-conjugated bombesin antagonist for targeting GRPr-positive tumours, Eur. J. Nucl. Med. Mol. Imaging, 38:97-107 (2011).
Mansi, R. et al., Targeting GRPR in urological cancers-from basic research to clinical application, Nature Review, Urology, 10:235-244 (2013) with Supplementary Table 1 attached.
Maurer, T. et al., Current use of PSMA-PET in prostate cancer management, Natures Review, Urology, 13:226-235 (2016).
Mease, R.C. et al., PET Imaging in Prostate Cancer: Focus on Prostate-Specific Membrane Antigen, CurrTop Med Chem, 13(8):951-962 (2013).
Minamimoto, R. et al., Pilot Comparison of (6)(8)Ga-RM2 PET and (6)(8)Ga-PSMA-11 PET in Patients with Biochemically Recurrent Prostate Cancer, J Nucl Med, 57(4):557-562 (2016).
Nawijn, M. et al., Genetically Engineered Mouse Models of Prostate Cancer, European Urology Supplements, 7:566-575(2008).
Nedrow, J. R. et al., Targeting PSMA with a Cu-64 Labeled Phosphoramidate Inhibitor for PET/CT Imaging of Variant PSMA-Expressing Xenografts in Mouse Models of Prostate Cancer, Mol. Imaging Biol., 18:402-410 (2016).
Osborne, J.R. et al., A Prospective Pilot Study of (89)Zr-J591/Prostate Specific Membrane Antigen Positron Emission Tomography in Men with Localized Prostate Cancer Undergoing Radical Prostatectomy, J Urol, 191(5):1439-1445 (2014).
Pandit-Taskar, N. et al., Evaluation of Castration-Resistant Prostate Cancer with Androgen Receptor-Axis Imaging, J Nucl Med, 57(Suppl 3):73s-78s (2016).
Pandit-Taskar, N. et al., First-in-Human Imaging with 89Zr-Df-IAB2M Anti-PSMA Minibody in Patients with Metastatic Prostate Cancer: Pharmacokinetics, Biodistribution, Dosimetry, and Lesion Uptake, J Nucl Med, 57(12):1858-1864 (2016).
Parisotto, M. and Metzger, D., Genetically engineered mouse models of prostate cancer, Mol Oncol, 7(2):190-205 (2013).
Philips E. et al., Clinical translation of an ultrasmall inorganic optical-PET imaging nanoparticle probe, Sci Transl Med, 6(260):260ra149 (2014).
Reinfelder, J., MD et al., First Experience With SPECT/CT Using a $^{99m}$Tc-Labeled Inhibitor for Prostate-Specific Membrane Antigen in Patients With Biochemical Recurrence of Prostate Cancer, Clinical Nuclear Medicine, 42(1):26-33 (2017).
Rowe, S.P. et al., 18F-DCFBC PET/CTforPSMA-Based Detection and Characterization of Primary Prostate Cancer, J Nucl Med, 56(7):1003-1010 (2015).
Rowe, S.P. et al., Prostate-Specific Membrane Antigen-Targeted Radiohalogenated PET and Therapeutic Agents for Prostate Cancer, J Nucl Med, 57(Suppl 3):90s-96s (2016).
Siegel, R. et al., Cancer Statistics, 2017, CA Cancer J Clin 67(1):7-30 (2017).
Silberstein, J. L. and Laudone, V. P., Pelvic Lymph Node Dissection for Prostate Cancer, Radical Prostatectomy: Surgical Perspectives, 4:57-74 (2014).
Vali, R. et al., Imaging of prostate cancer with PET/CT using (18)F-Fluorocholine, Am J Nucl Med Mol Imaging, 5(2):96-108 (2015).
Vargas, H.A. et al., Performance Characteristics of MR Imaging in the Evaluation of Clinically Low-Risk Prostate Cancer: A Prospective Study, Radiology, 265(2):478-487 (2012).
Vela, I. and Chen, Y., Prostate cancer organoids: a potential new tool fortesting drug sensitivity, Expert Rev Anticancer Ther, 15(3):261-263 (2015).
Warram, J.M. et al., Antibody Based Imaging Strategies of Cancer, Cancer Metastasis Rev, 33(0):809-822 (2014).
Watson, P.A. et al., Context-Dependent Hormone-Refractory Progression Revealed Through Characterization of a Novel Murine Prostate Cancer Cell Line, Cancer Res, 65(24):11565-11571 (2005).
Weineisen, M. et al., 68Ga- and 177Lu-Labeled PSMA I&T: Optimization of a PSMA-Targeted Theranostic Concept and First Proof-of-Concept Human Studies. J Nucl Med. 2015;56(8):1169-76. PubMed PMID: 26089548.
Weiser, G. et al., Diagnosis of recurrent prostate cancer with PET/CT imaging using the gastrin-releasing peptide receptor antagonist 68Ga-RM2: Preliminary results in patients with negative or inconclusive [18F]Fluoroethylcholine-PET/CT Gesche, Eur. J. Nucl. Med. Mol. Imaging, 44:1463-1472 (2017).
Weissleder, R., MD, PhD et al., Ultrasmall Superparamagnetic Iron Oxide: An Intravenous Contrast Agent for Assessing Lymph Nodes with MRI Imaging, Radiology, 175(2):494-498 (1990).
Written Opinion, PCT/US2017/063641 (Inhibitor-Functionalized Ultrasmall Nanoparticles and Methods Thereof, filed Nov. 29, 2017), issued by ISA/EPO, 6 pages, dated Mar. 6, 2018.
Zhang, H. et al., Dual-Modality Imaging of Prostate Cancer with a Fluorescent and Radiogallium-Labeled Gastrin-Releasing Peptide Receptor Antagonist, J Nucl Med, 58(1):29-35 (2017).
Zhang, X. et al., [$^{99m}$Tc(CO)$_3$]$^+$ and [$^{99m}$TcO$_2$]$^+$ Radiolabeled Cyclic Melanotropin Peptides for Melanoma SPECT Imaging, Current Radiopharmaceuticals, 7:63-74 (2014).
Zhang, Y. et al., PET tracers based on Zirconium-89, Curr Radiopharm, 4(2):131-139 (2011).

* cited by examiner

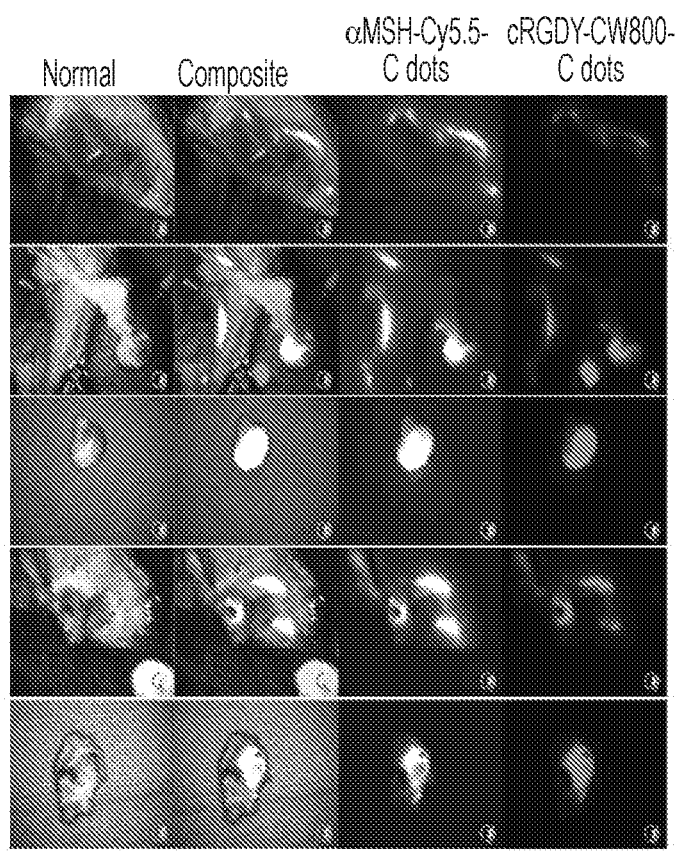
FIG. 16A
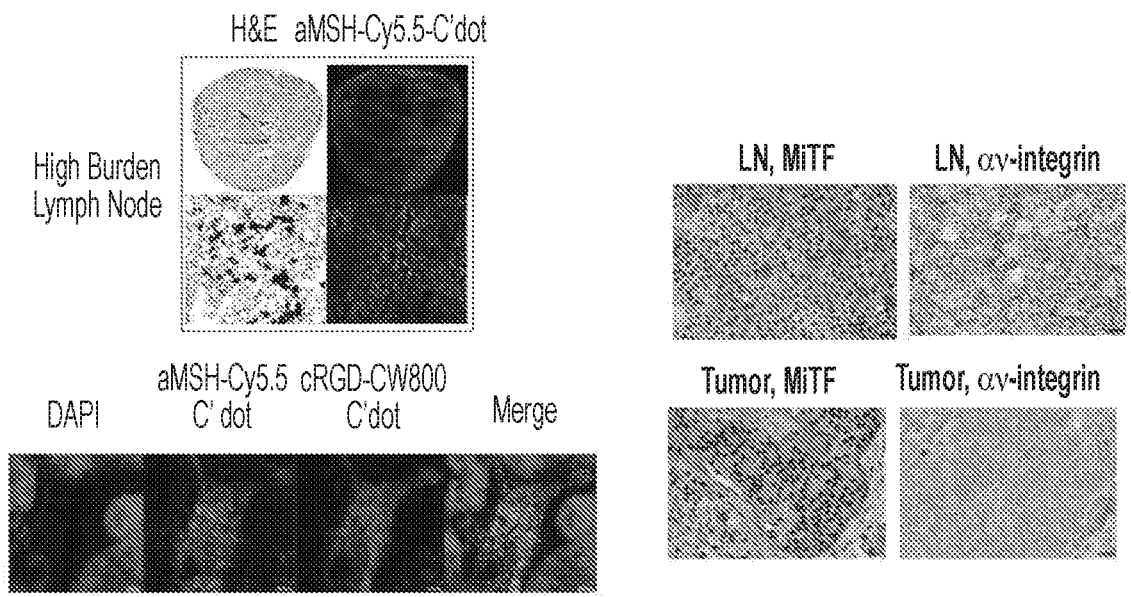
FIG. 16B
FIG. 16C

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(4)
<223> OTHER INFORMATION: /note="Cyclic"

<400> SEQUENCE: 1

Arg Gly Asp Tyr
1

<210> SEQ ID NO 2
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: source
<223> OTHER INFORMATION: /note="N-term 4-amino-1-carboxy-methyl-
      piperidine modified"
<220> FEATURE:
<221> NAME/KEY: MOD_RES
<222> LOCATION: (8)..(8)
<223> OTHER INFORMATION: Statine

<400> SEQUENCE: 2

His Gln Trp Ala Val Gly His Xaa Leu
1               5
```

INHIBITOR-FUNCTIONALIZED ULTRASMALL NANOPARTICLES AND METHODS THEREOF

CROSS REFERENCE TO RELATED APPLICATIONS

This application claims the benefit of U.S. Application Ser. No. 62/427,845 filed on Nov. 30, 2016, and is the national stage entry of PCT Application No. PCT/US17/63641, filed on Nov. 29, 2017, the disclosures of which are hereby incorporated by reference in their entireties.

GOVERNMENT SUPPORT

This invention was made with government support under grant numbers CA092629 and CA199081 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Nov. 20, 2017, is named 2003080-1491_SL.txt and is 1,041 bytes in size.

TECHNICAL FIELD

The invention relates generally to the development of conjugates for attaching an inhibitor and a metal chelator to a macromolecule (e.g., nanoparticle, polymer, protein). More particularly, in certain embodiments, the invention relates to attaching prostate specific membrane antigen (PSMA) inhibitors or gastrin-releasing peptide receptor (GRPr) inhibitors to ultrasmall nanoparticles.

BACKGROUND

Prostate cancer (PC) is one of the most common types of cancer in men. PC usually grows slowly and initially remains confined to the prostate gland, where it may not cause serious harm. An estimated 26,730 men are expected to succumb to PC in the U.S. in 2017, making this cancer the second most common cause of cancer-related death in men. The major determinants of prostate cancer-specific mortality are a high Gleason score (greater than or equal to 8), seminal vesicle invasion, and lymph node (LN) metastasis. In the presence of LN metastasis, the long-term risk of death from PC is substantially increased, estimated at between 23% and 42%. In addition, at the time of tumor resection, failure to obtain negative surgical margins implies an inadequate excision that potentially leaves viable cancer cells at the site. In many cancers, positive surgical margins are associated with higher risk of local recurrence and systemic progression of disease. Unlike tumor stage and grade, positive surgical margins are the only prognostic factor primarily influenced by the surgeon's performance. Intraoperative challenges often include anatomical constraints, such as tumor impingement on neurovascular or bony structures, as in the case of radical prostatectomy for PC or excision of limb sarcomas. Other technical challenges include difficulties of visually distinguishing cancerous from healthy tissue during surgery, particularly for microscopic infiltration. The ability to detect the exact tumor margin, as well as foci of residual cancer in real-time, will allow surgeons to resect residual cancer to decrease the rate of positive surgical margins and thus treatment failure. It will also provide assurance that cancer is not present in certain critical structures and thereby reduce unnecessary functional tissue damage.

While some types of prostate cancer grow slowly and may need minimal or no treatment, other types are aggressive. Various prostate tissue specific surface proteins have been evaluated as potential binding targets to improve tumor uptake and retention of therapeutic agents. The most extensively characterized surface protein has been prostate-specific membrane antigen (PSMA).

Nanotherapeutic delivery vehicles are typically macro- or supra-molecular multicomponent systems having size up to about 1,000 nm in diameter, that are either inherently therapeutic (e.g., no active pharmaceutical ingredient) or function as therapeutic delivery systems. To date, liposomal nanoparticles and biologics comprise a large proportion of the number of FDA-approved products or products in clinical trials used to treat a variety of cancer types, while a number of polymer-based particle formulations are currently in early phase trials.

Desirable candidates for nanotherapeutic delivery systems share a common feature of incorporating and releasing a drug compound, such as PSMA inhibitors, in a controlled manner, which can favorably alter drug bioavailability and pharmacokinetics, while minimizing off-target toxicities. Ideally, an imaging label is incorporated therein to assess their precise localization and retention at disease sites.

However, these systems function using different mechanisms. For example, antibody drug conjugates (ADCs) achieve lower drug toxicity primarily through active targeting of tumor cells and conditional release of drug molecules. Upon binding a cell surface antigen, active drug release occurs after cellular internalization and endosomal uptake. On the other hand, liposomes and polymer-based drug delivery systems, which are typically much larger assembled complexes (~20-150 nm diameters) passively loaded with a greater payload (10,000 drug molecules for Doxil), have generally lacked targeting capabilities (BIND-014 is an exception). Therefore, these complexes rely primarily on the well-known enhanced permeability and retention (EPR) effect.

Moreover, while radioimmunoconjugates and radiolabeled particle probes are also available for imaging metastases, these have been limited by their larger size (e.g., greater than 20-nm), prolonged kinetics, and higher background signal. In addition to not being suitable for intraoperative imaging, superparamagnetic iron oxide nanoparticles were not approved by the Food and Drug Administration for clinical use as MRI lymphography contrast agents, although showing promising preclinical and clinical results. The $^{111}$In-labeled, anti-PSMA monoclonal antibody (mAb) ProstaScint, primarily indicated in patients at high risk for metastases, demonstrates slow whole-body distribution, leading to extended (greater than 3 day) post-injection (p.i.) imaging intervals. While improvements to mAb-based imaging have come from the use of J591 mAb, which binds an external PSMA epitope, and the use of $^{89}$Zr for PET imaging, slow mAb target recognition and clearance have resulted in a less than optimal imaging time frame. Radiolabeled steroids, like $^{18}$F-fluorodihydrotestosterone ($^{18}$F-FDHT), are very hydrophobic, leading to significant background activity.

The role of cross-sectional imaging and imaging tracers for perioperative detection of LN metastases remains limited, with no reliable imaging modality currently available.

A recent meta-analysis reported the sensitivity of CT for detection of LN metastases as 42% at a specificity of 82%. Existing PET tracers also perform suboptimally. Although $^{18}$F-FDG is most commonly used, its specificity and sensitivity vary greatly with PC stage and aggressiveness. $^{11}$C-choline has a 90% reported specificity and 57% sensitivity, whereas $^{18}$F-fluoromethylcholine has a specificity of 94% and sensitivity of ~56%. Additional limitations include high energy gamma emissions during positron decay of $^{11}$C and $^{18}$F, making it difficult to localize nodes with a handheld intraoperative probe, as well as short physical half-lives requiring tracer injection shortly before surgery and leading to significant radiation exposure during prostatectomy.

Inhibitor and antagonist peptido-based agents targeting PSMA and GRPr have shown promise for imaging preclinical PC xenograft models. Many of these peptide-based PC-targeting probes have been modified with various linkers and radiometal chelators for PC imaging and therapy, such as the widely-studied Lys-urea-Glu PSMA inhibitor (PSMAi) probe. Unfortunately, many PSMA-targeting peptido-probes suffer from extremely high renal and salivary gland uptake, limiting radiotherapeutic doses and reducing efficacy. Further, it is common to observe abnormally high pancreatic uptake of $^{68}$Ga- or $^{177}$Lu-GRPr antagonist, RM2, which otherwise shows enhanced tumor uptake in preclinical and clinical studies. Importantly, although $^{68}$Ga-RM2 exhibits distinct clearance and tissue distribution profiles relative to PSMAi-$^{68}$Ga-HBED, suggesting feasibility of dual-peptide imaging of heterogeneous receptor expression, heterodimeric constructs of GRP$_{(7-14)}$ and PSMAi demonstrate targeting with high gut uptake, limiting clinical utility.

Alternative nanotherapeutic delivery systems include ultrasmall nanoparticles. Ultrasmall (e.g., having a diameter up to 20 nm) FDA-approved fluorescent organo-silica particles (C dots) that were previously surface-adapted with PET radiolabels and the integrin-targeting peptide cyclo-(Arg-Gly-Asp-Tyr) (cRGDY) (SEQ ID NO: 1) were found to be a working molecular cancer imaging agent in humans. For example, C dots were shown to preferentially accumulate within αvβ3 integrin-expressing primary and/or metastatic lesions in small and larger animal and human subject melanoma models in addition to demonstrating bulk renal clearance. Details on C dots are described in U.S. Pat. No. 8,298,677 B2 "Fluorescent silica-based nanoparticles", U.S. Publication No. 2013/0039848 A1 "Fluorescent silica-based nanoparticles", and U.S. Publication No. US 2014/0248210 A1 "Multimodal silica-based nanoparticles", the contents of which are incorporated herein by reference in their entireties. Moreover, ultrasmall poly(ethylene glycol)-coated (PEGylated) near-infrared (NIR) fluorescent silica nanoparticle, referred to as C' dots, with diameters controllable down to the sub-10 nm range that were additionally surface-modified with a 14-mer peptide analog, alpha-melanocyte stimulating hormone (α-MSH) were found to target melanocortin-1 receptors (MC1-R) expressed on malignant melanoma cells.

The prostate specific membrane antigen (PSMA) inhibitor and metal chelator construct, known as PSMAi-HBED-CC in the literature, is currently the most clinically advanced molecule for the detection of primary prostate tumors and metastatic lesions.

There remains a need for improved delivery systems for treatment of prostate cancer. Such systems need to offer multi-marker detection capabilities to address heterogeneity of cancer markers targeting different biological processes, particularly across pathological stages, to determine best treatment management options.

SUMMARY

Described herein are prostate cancer (PC)-targeting nanoparticles (e.g., PC-targeting dots (C' dots)) to detect disease and enable more reliable staging of disease. This technology provides the ability to identify patients potentially curable by surgical resection versus those for whom systemic therapy would be required. Assessing and surgically treating metastases, while addressing disease heterogeneity through the identification of two predictive biomarkers that assess distinct biological processes, has implications on the choice of systemic therapeutic options. Surface chemical designs are described for accurately identifying one or more metastatic markers expressed by PC models and human subjects. The addition of real-time, optically-driven molecular phenotyping capabilities in surgical settings help to enable detection of multiple critical cancer targets (multiplexing) that are known to control different biological processes. Such readouts provide a precision-based approach to surgical staging and management that may complement preoperative PET-CT and anatomic assessments of the draining tumor lymphatics and surgical margins.

The technology described herein reliably detects and treats cancer-bearing nodes and sites of residual disease. The technology provides real-time in vivo molecular characterization of multiple cancer targets that can improve sensitivity, specificity, and detection accuracy. Moreover, the described platform provides improved metastatic disease assessment and surgical treatment of PC by (1) promoting multivalent interactions with receptor targets that enhance potency and target-to-background ratios (contrast); and (2) exploiting its superior photophysical properties, alongside device technologies, to maximize detection sensitivity.

The technology offers at least the following advantages compared to alternative technologies: (1) an "all-in-one" dual-modality and clinically-translatable inhibitor (e.g., PSMA inhibitor, e.g., GRPr inhibitor)-targeting platform for perioperative management of PC; (2) utilization of spectrally-distinct PC-targeting C' dots and fluorescence-based multiplexing strategies for real-time evaluation of multiple molecular cancer phenotypes; (3) qualification of reliable staging biomarkers targeting different biological processes for direct clinical validation; (4) characterization of inhibitor expression levels for new metastatic PC subclones and human prostate organoid-based models that may more faithfully reproduce human disease; (5) efficient optimization of new surface designs for renally-clearable PC-targeted C' dots which overcome high non-specific uptake in radiosensitive organs (e.g., kidney, salivary glands), where such non-specific uptake has limited radiotherapeutic dosing and treatment efficacy; (6) use of particle-encapsulated NIR dyes to obviate attendant losses in bioactivity seen with NIR dye-conjugated inhibitor, the latter precluding NIR-driven optical applications; and (7) chemical adaptation of linker-peptide chemistries prior to C' dot attachment to preserve pharmacophore activity while enhancing radiolabeling and tumor-targeting efficiencies.

For example, commercially available PSMAi-HBED-CC compounds are not compatible for conjugation to nanotherapeutic delivery systems. All reported studies evaluating PSMA inhibitor-metal chelator constructs have thus far focused on the use of the free compound. Preclinical studies have shown the PSMA inhibitor to be more effective (e.g., enhanced binding and cellular uptake) when coupled to certain types of metal chelators, than when used alone. While the PSMA inhibitor alone has been used on macromolecules for PSMA targeting, the development of PSMA inhibitor-metal chelator constructs, for example, PSMAi-HBED-CC analogs, compatible for conjugation onto a macromolecular entity have not been reported. Described herein are conjugates comprising a PSMA inhibitor and metal chelator that are covalently attached to a macromolecule (e.g., a nanoparticle, a polymer, a protein). Such conjugates may exhibit enhancements in binding and cell uptake properties (due to multivalency) and pharmacokinetics (due to increased molecular weight or size) over the free, unbound PSMA inhibitor/chelator construct. For example, PSMA inhibitor displayed on a macromolecule (e.g., nanoparticle) surface has reduced kidney uptake compared with PSMA inhibitor constructs alone.

In one aspect, the invention is directed to a composition (e.g., a conjugate) comprising a prostate specific membrane antigen inhibitor (PSMAi)/chelator construct covalently attached to a macromolecule (e.g., nanoparticle, e.g., polymer, e.g., protein).

In certain embodiments, the construct has the structure:

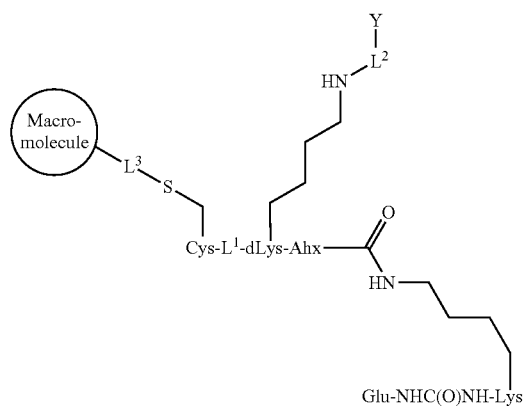

wherein: $L^1$ is a peptidic fragment comprising from 1 to about 10 natural or unnatural amino acid residues, or an optionally substituted, bivalent, $C_{1-20}$ saturated or unsaturated, straight or branched, hydrocarbon chain, wherein one or more methylene units of the hydrocarbon chain are optionally and independently replaced by —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—; $L^2$ is an optionally substituted, bivalent, $C_{1-10}$ saturated or unsaturated, straight or branched, hydrocarbon chain, wherein one or more methylene units of the hydrocarbon chain are optionally and independently replaced by -Cy-, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—; $L^3$ is a covalent bond or a crosslinker derived from a bifunctional crosslinking reagent capable of conjugating a reactive moiety of the (PSMAi)/chelator construct with a reactive moiety of the macromolecule, each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; Y is a chelator moiety; and R is hydrogen, $C_{1-6}$ alkyl, or a nitrogen protecting group; wherein each amino acid residue, unless otherwise indicated, may be protected or unprotected on its terminus and/or side chain group.

In certain embodiments, $L^1$ is a peptidic fragment comprising 1, 2, 3, 4, or 5 natural or unnatural amino acid residues. In certain embodiments, $L^1$ comprises one or two units of 6-aminohexanoic acid (Ahx). In certain embodiments, $L^1$ is -Ahx-Ahx-. In certain embodiments, $L^1$ is a $C_{1-10}$ saturated or unsaturated, straight or branched, hydrocarbon chain, wherein one or more methylene units of the hydrocarbon chain are optionally and independently replaced by —NR—, —O—, or —C(O)—. In certain embodiments, $L^1$ comprises one or more units of —(CH$_2$CH$_2$O)— or —(OCH$_2$CH$_2$)—.

In certain embodiments, $L^2$ is a $C_{1-3}$ saturated or unsaturated, straight or branched, hydrocarbon chain, wherein one or more methylene units of the hydrocarbon chain are optionally and independently replaced by -Cy-, —NR—, —N(R)C(O)—, —C(O)N(R)—, —O—, —C(O)—, —OC(O)—, or —C(O)O—. In certain embodiments, $L^2$ is a $C_{1-3}$ saturated or unsaturated, straight or branched, hydrocarbon chain, wherein one, two, or three, methylene units of the hydrocarbon chain are optionally and independently replaced by -Cy-, —NR—, or —C(O)—. In certain embodiments, -Cy- is phenylene. In certain embodiments, $L^2$ is —C(O)— or —C(O)NH-phenylene.

In certain embodiments, the chelator is DOTA. In certain embodiments, the chelator is NOTA.

In certain embodiments, $L^3$ is derived from a bifunctional crosslinking reagent capable of conjugating a sulfhydryl on the (PSMAi)/chelator construct with a moiety of the macromolecule.

In certain embodiments, the bifunctional crosslinking reagent is a maleimide or haloacetyl. In certain embodiments, the bifunctional crosslinking reagent is a maleimide.

In certain embodiments, the macromolecule is a nanoparticle (e.g., an ultrasmall nanoparticle, e.g., a C-dot, e.g., a C'-dot). In certain embodiments, the macromolecule has a diameter no greater than 20 nm (e.g., has a diameter no greater than 15 nm, e.g., has a diameter no greater than 10 nm).

In certain embodiments, the composition comprises: a fluorescent silica-based nanoparticle comprising: a silica-based core; a fluorescent compound within the core; a silica shell surrounding a portion of the core; an organic polymer attached to the nanoparticle, thereby coating the nanoparticle, wherein the nanoparticle has a diameter no greater than 20 nm.

In certain embodiments, from 1 to 100 (e.g., from 1 to 60, e.g., from 1 to 50 e.g., from 1 to 30, e.g., from 1 to 20) PSMAi ligands are attached to the macromolecule. In certain embodiments, the macromolecule comprises a radiolabel (e.g., $^{89}$Zr, $^{64}$Cu, $^{68}$Ga, $^{86}$Y, $^{124}$I, $^{177}$Lu, $^{225}$Ac, $^{212}$Pb, $^{67}$Cu and $^{211}$At).

In certain embodiments, the chelator comprises a member selected from the group consisting of N,N'-Bis(2-hydroxy-5-(carboxyethyl)-benzyl)ethylenediamine-N,N'-diacetic acid (HBED-CC) (HBED-CC), 1,4,7,10-tetraazacyclododecane-1,4,7,10-tetraacetic acid (DOTA), diethylenetriaminepentaacetic (DTPA), desferrioxamine (DFO), and triethylenetetramine (TETA).

In certain embodiments, the composition comprises:

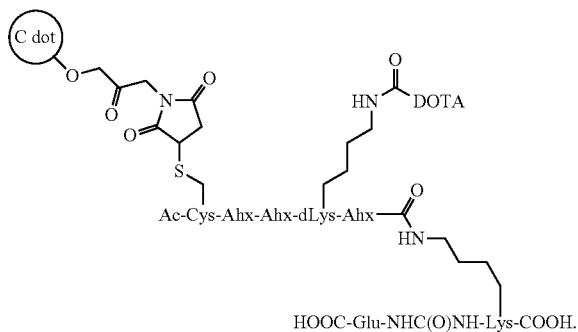

HOOC-Glu-NHC(O)NH-Lys-COOH.

In certain embodiments, the composition comprises:

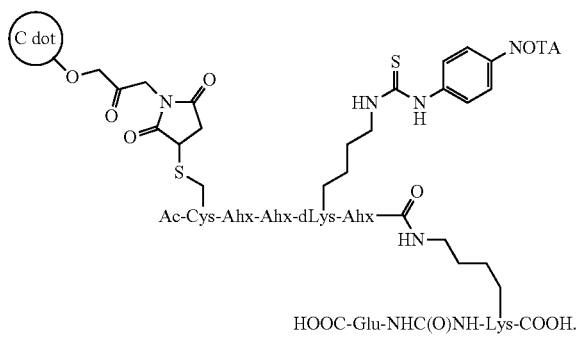

HOOC-Glu-NHC(O)NH-Lys-COOH.

In certain embodiments, the method comprises loading orthogonally protected lysine building block comprising a suitable protecting group (e.g., Fmoc-Lys(Dde)-OH) on a resin (e.g., a 2-ClTrt resin) (e.g., in a manual reaction vessel); removing the suitable protecting group from the resin to produce a first compound; contacting (e.g., at the same time as the removing step) protected glutamic acid (e.g., di-tBU protected) with suitable reagents (e.g., triphosgene and DIEA, e.g., for 6 h at 0° C.) to produce a glutamic isocyanate building block [OCN-Glu-(OtBu)$_2$]; contacting (e.g., overnight, e.g., at room temperature) the isocyanate building block [OCN-Glu-(OtBu)2] with a free α amino group of the first compound to yield a fully protected urea on a second compound on the resin.

In certain embodiments, the second compound is further reacted by removing a protecting group (e.g., by 2% hydrazine) on a Lys of the second compound; obtaining a third compound by building a peptide sequence (e.g., Ac-Cys-Ahx-Ahx-dLys-Ahx-) on the s-amino group of the Lys of the second compound; removing suitable protecting groups (e.g., with Trt for Cys and Mtt for Lys) as appropriate (e.g., via treatment with 20% Piperidine, e.g., for 10 min); optionally, assembling (e.g. And recoupling at every cycle) a peptide chain via sequential acylation (e.g., 20 min for coupling) with "in situ" activated suitably protected amino acids (e.g., where the "in situ" activated Fmoc-amino acids were carried out using with uronium salts and DIEA); removing a suitable protecting group on dLys (e.g., in the same reaction); cleaving the third compound from the resin (e.g., via treatment of TFA) to produce a fourth compound;

contacting (e.g., overnight, e.g., in DMF) the fourth compound with a suitable chelator reagent (e.g., p-SCN-Bn-NOTA) in the presence of a suitable base to produce a chelator-labeled (e.g., NOTA-labeled, e.g., DOTA-labeled, e.g., HBED-CC-labeled) fifth compound; removing protecting groups from the fifth compound (e.g., via TFA, e.g., in the presence of scavengers (e.g., at a 2.5% w/v concentration) (e.g., wherein the scavengers comprise one or more of phenol, water, TIS, TA, and EDT) to produce a sixth compound (e.g., target molecule, e.g., PSMAi-NOTA, e.g., PSMAi-DOTA, e.g., PSMAi-HBED-CC); optionally purifying the sixth compound; and attaching (e.g., covalently, e.g., malemide chemistry) the sixth compound to a macromolecule (e.g., nanoparticle (e.g., C' or C dot), e.g., polymer, e.g., protein); (e.g., selectively protecting a diprotected HBED-CC using trityl type protecting group (e.g., Trt, ClTrt, Mtt, Mmt) or similar).

In certain embodiments, the third compound is or comprises:

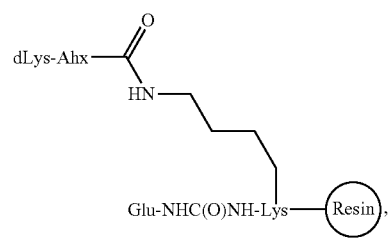

wherein one or more amino acid side chain groups or termini are optionally protected with a suitable protecting group.

In certain embodiments, the third compound is:

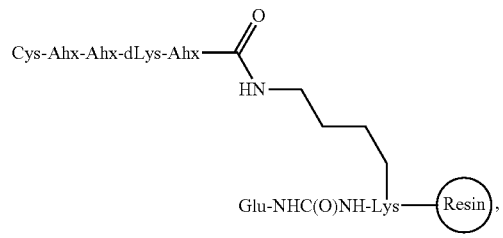

wherein one or more amino acid side chain groups or termini are optionally protected with a suitable protecting group.

In another aspect, the invention is directed to a compound:

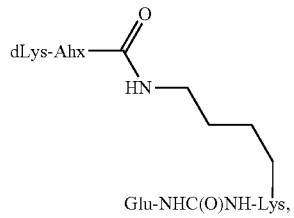

wherein one or more amino acid side chain groups or termini are optionally protected with a suitable protecting group, and wherein one amino acid is optionally attached to a resin.

In another aspect, the invention is directed to a compound:

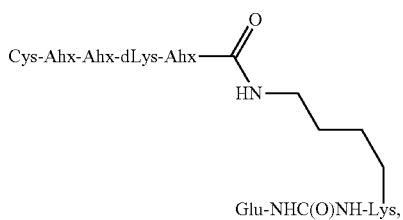

wherein one or more amino acid side chain groups or termini are optionally protected with a suitable protecting group, and wherein one amino acid is optionally attached to a resin.

In another aspect, the invention is directed to a compound selected from:

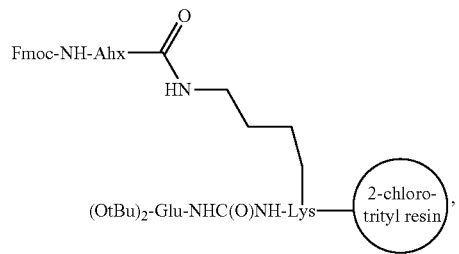

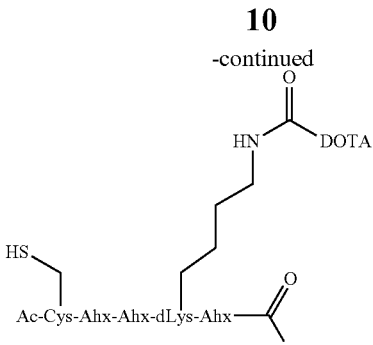

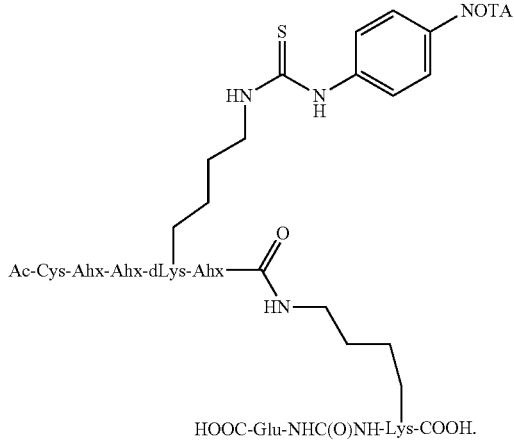

In another aspect, the invention is directed to a compound selected from:

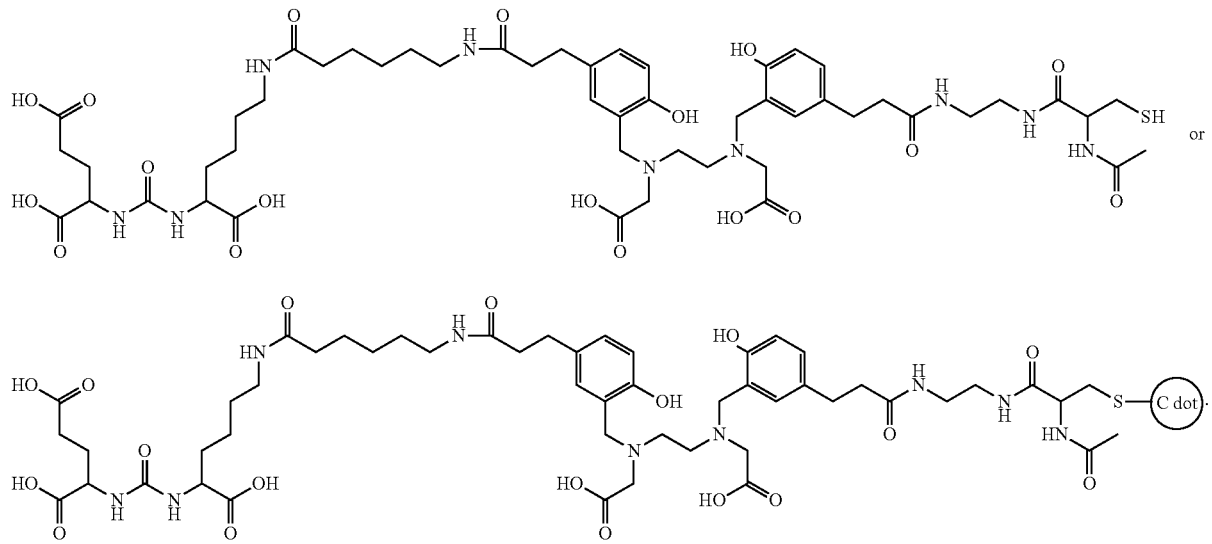

In another aspect, the invention is directed to a method of treating a disease or condition, the method comprising: administering to a subject a pharmaceutical composition comprising the composition of any one of claims 1 to 24 (e.g., to target a particular type of tissue (e.g., cancer tissue) (e.g., prostate cancer tissue).

In certain embodiments, the pharmaceutical composition further comprises a carrier.

In another aspect, the invention is directed to a method of in vivo imaging (e.g., intraoperative imaging), the method comprising: administering to a subject the composition of any one of claims 1 to 24 (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a prostate specific membrane antigen inhibitor (PSMAi)/chelator construct covalently attached to a macromolecule (e.g., nanoparticle, e.g., polymer, e.g., protein) for use in a method of treating cancer (e.g., prostate cancer) in a subject, wherein the treating comprises delivering the composition to the subject.

In another aspect, the invention is directed to a composition (e.g., a pharmaceutical composition) comprising a prostate specific membrane antigen inhibitor (PSMAi)/chelator construct covalently attached to a macromolecule (e.g., nanoparticle, e.g., polymer, e.g., protein) for use in a method of in vivo diagnosis of cancer (e.g., prostate cancer) in a subject, the in vivo diagnosis comprises: delivering the composition to the subject (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a prostate specific membrane antigen inhibitor (PSMAi)/chelator construct covalently attached to a macromolecule (e.g., nanoparticle, e.g., polymer, e.g., protein) for use in (a) a method of treating cancer in a subject or (b) a method of in vivo diagnosis of cancer in a subject, wherein the method comprises: delivering the composition to the subject (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a prostate specific membrane antigen inhibitor (PSMAi)/chelator construct covalently attached to a macromolecule (e.g., nanoparticle, e.g., polymer, e.g., protein) for use in therapy.

In another aspect, the invention is directed to a composition (e.g., a pharmaceutical composition) comprising a prostate specific membrane antigen inhibitor (PSMAi)/chelator construct covalently attached to a macromolecule (e.g., nanoparticle, e.g., polymer, e.g., protein) for use in in vivo diagnosis.

In certain embodiments, the macromolecule is a nanoparticle (e.g., an ultrasmall nanoparticle, e.g., a C-dot, e.g., a C'-dot). In certain embodiments, the macromolecule has a diameter no greater than 20 nm (e.g., has a diameter no greater than 15 nm, e.g., has a diameter no greater than 10 nm). In certain embodiments, the macromolecule comprises: a fluorescent silica-based nanoparticle comprising: a silica-based core; a fluorescent compound within the core; a silica shell surrounding a portion of the core; an organic polymer attached to the nanoparticle, thereby coating the nanoparticle, wherein the nanoparticle has a diameter no greater than 20 nm.

In certain embodiments, from 1 to 20 PSMAi ligands are attached to the macromolecule.

In certain embodiments, the composition comprises a radiolabel (e.g., $^{89}$Zr, $^{64}$Cu, $^{68}$Ga, $^{86}$Y, $^{124}$I, $^{177}$Lu, $^{225}$Ac, $^{212}$Pb, and $^{211}$At).

In certain embodiments, the chelator comprises a member selected from the group consisting of N,N'-Di(2-hydroxybenzyl)ethylenediamine-N,N'-diacetic acid monohydrochloride (HBED-CC), 1,4,7,10-tetraazacyclododecane-1,4,7,10-tetraacetic acid (DOTA), diethylenetriaminepentaacetic (DTPA), desferrioxamine (DFO), and triethylenetetramine (TETA).

In certain embodiments, the composition comprises:

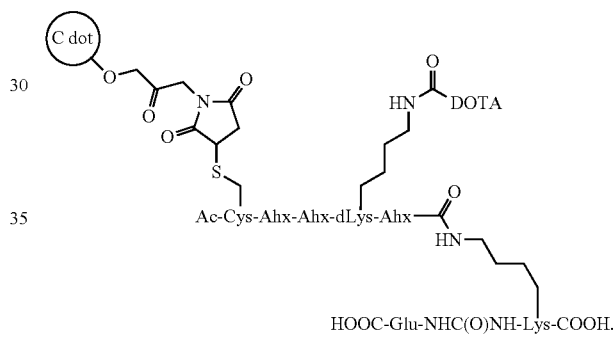

In certain embodiments, the composition comprises:

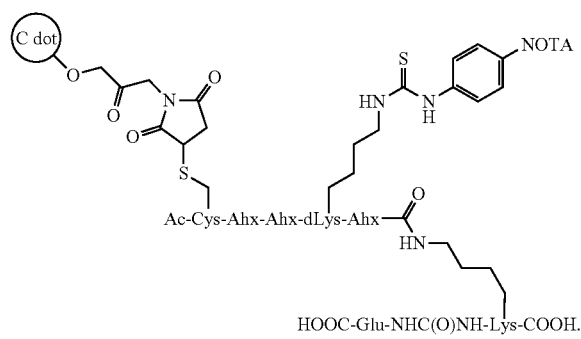

In another aspect, the invention is directed to a composition (e.g., a conjugate) comprising a bombesin/gastrin-releasing peptide receptor ligand (GRP)/chelator construct covalently attached to a macromolecule (e.g., nanoparticle, e.g., polymer, e.g., protein).

In certain embodiments, the bombesin/gastrin-releasing peptide receptor ligand (GRP)/chelator construct comprises a peptide of the sequence:

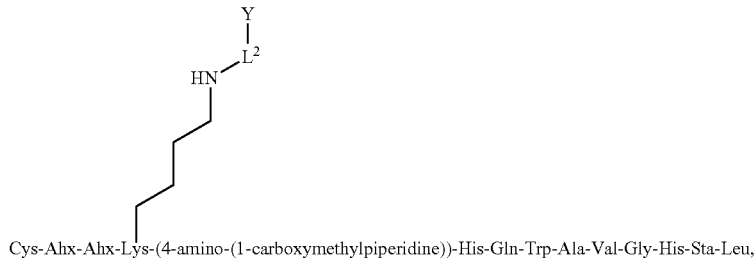

Cys-Ahx-Ahx-Lys-(4-amino-(1-carboxymethylpiperidine))-His-Gln-Trp-Ala-Val-Gly-His-Sta-Leu, wherein: $L^2$ is an optionally substituted, bivalent, $C_{1-10}$ saturated or unsaturated, straight or branched, hydrocarbon chain, wherein one or more methylene units of the hydrocarbon chain are optionally and independently replaced by -Cy-, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—; each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur; Y is a chelator moiety; and R is hydrogen, $C_{1-6}$ alkyl, or a nitrogen protecting group; wherein each amino acid residue, unless otherwise indicated, may be protected or unprotected on its terminus and/or side chain group.

In certain embodiments, the bombesin/gastrin-releasing peptide receptor ligand (GRP)/chelator construct is covalently attached via the depicted cysteine residue to the macromolecule through $L^3$, wherein, $L^3$ is a covalent bond or a crosslinker derived from a bifunctional crosslinking reagent capable of conjugating a reactive moiety of the bombesin/gastrin-releasing peptide receptor ligand (GRP)/chelator construct with a reactive moiety of the macromolecule.

In certain embodiments, the bombesin/gastrin-releasing peptide receptor ligand (GRP)/chelator construct has the structure:

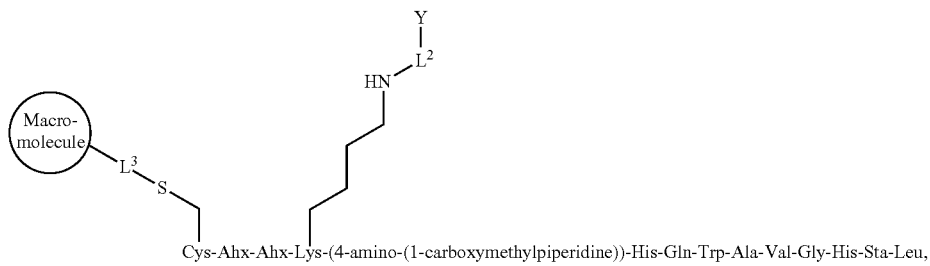

Cys-Ahx-Ahx-Lys-(4-amino-(1-carboxymethylpiperidine))-His-Gln-Trp-Ala-Val-Gly-His-Sta-Leu, wherein each of $L^2$, $L^3$, Y is as defined above and described in classes and subclasses herein, both singly and in combination.

In certain embodiments, $L^3$ is derived from a bifunctional crosslinking reagent capable of conjugating a sulfhydryl on the bombesin/gastrin-releasing peptide receptor ligand (GRP)/chelator construct with a moiety of the macromolecule. In certain embodiments, the bifunctional crosslinking reagent is a maleimide or haloacetyl. In certain embodiments, the bifunctional crosslinking reagent is a maleimide.

In certain embodiments, $L_2$ is a covalent bond.

In certain embodiments, the chelator is DOTA. In certain embodiments, the chelator is NOTA.

In certain embodiments, the macromolecule is a nanoparticle (e.g., an ultrasmall nanoparticle, e.g., a C-dot, e.g., a C'-dot). In certain embodiments, the macromolecule has a diameter no greater than 20 nm (e.g., has a diameter no greater than 15 nm, e.g., has a diameter no greater than 10 nm). In certain embodiments, the macromolecule comprises: a fluorescent silica-based nanoparticle comprising: a silica-based core; a fluorescent compound within the core; a silica shell surrounding a portion of the core; an organic polymer attached to the nanoparticle, thereby coating the nanoparticle, wherein the nanoparticle has a diameter no greater than 20 nm.

In certain embodiments, from 1 to 100 (e.g., from 1 to 60, e.g., from 1 to 50 e.g., from 1 to 30, e.g., from 1 to 20) bombesin/gastrin-releasing peptide receptor ligand are attached to the macromolecule.

In certain embodiments, the composition further comprises a radiolabel (e.g., $^{89}$Zr, $^{64}$Cu, $^{68}$Ga, $^{86}$Y, $^{124}$I, $^{177}$Lu, $^{225}$Ac, $^{212}$Pb, $^{67}$Cu and $^{211}$At).

In certain embodiments, the chelator comprises a member selected from the group consisting of N,N'-Bis(2-hydroxy-5-(carboxyethyl)-benzyl)ethylenediamine-N,N'-diacetic acid (HBED-CC) (HBED-CC), 1,4,7,10-tetraazacyclododecane-1,4,7,10-tetraacetic acid (DOTA), diethylenetriaminepentaacetic (DTPA), desferrioxamine (DFO), and triethylenetetramine (TETA).

In certain embodiments, the composition comprises:

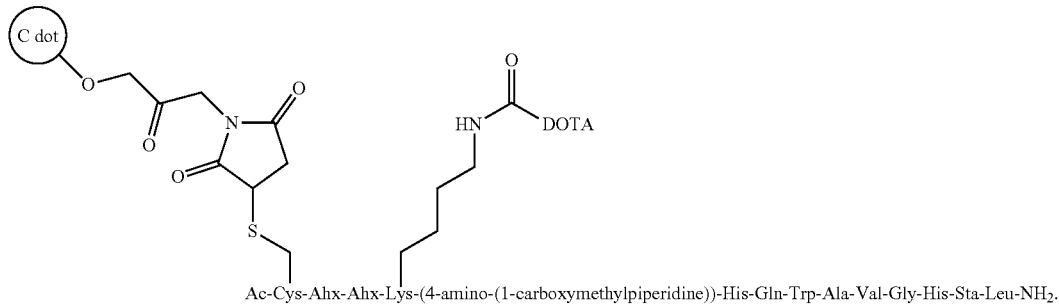

Ac-Cys-Ahx-Ahx-Lys-(4-amino-(1-carboxymethylpiperidine))-His-Gln-Trp-Ala-Val-Gly-His-Sta-Leu-NH$_2$.

In certain embodiments, the composition comprises:

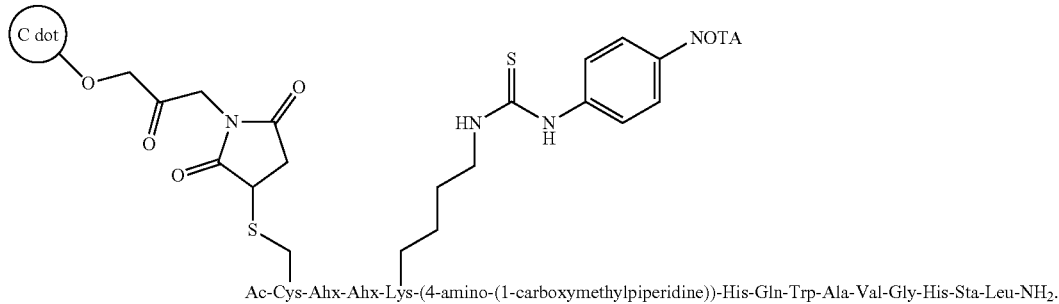

Ac-Cys-Ahx-Ahx-Lys-(4-amino-(1-carboxymethylpiperidine))-His-Gln-Trp-Ala-Val-Gly-His-Sta-Leu-NH$_2$.

In another aspect, the invention is directed to a method of treating a disease or condition, the method comprising: administering to a subject a pharmaceutical composition comprising the composition of as described herein (e.g., to target a particular type of tissue (e.g., cancer tissue) (e.g., prostate cancer tissue).

In certain embodiments, the pharmaceutical composition further comprises a carrier.

In another aspect, the invention is directed to a method of in vivo imaging (e. g., intraoperative imaging), the method comprising: administering to a subject the composition as described herein (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a bombesin/gastrin-releasing peptide receptor ligand (GRP)/chelator construct covalently attached to a macromolecule (e.g., nanoparticle, e.g., polymer, e.g., protein) for use in a method of treating cancer (e.g., prostate cancer) in a subject, wherein the treating comprises delivering the composition to the subject.

In another aspect, the invention is directed to a composition (e.g., a pharmaceutical composition) comprising a bombesin/gastrin-releasing peptide receptor ligand (GRP)/chelator construct covalently attached to a macromolecule (e.g., nanoparticle, e.g., polymer, e.g., protein) for use in a method of in vivo diagnosis of cancer (e.g., prostate cancer) in a subject, the in vivo diagnosis comprises: delivering the composition to the subject (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a bombesin/gastrin-releasing peptide receptor ligand (GRP)/chelator construct covalently attached to a macromolecule (e.g., nanoparticle, e.g., polymer, e.g., protein) for use in (a) a method of treating cancer in a subject or (b) a method of in vivo diagnosis of cancer in a subject, wherein the method comprises: delivering the composition to the subject (e.g., such that the composition preferably collects in a particular region (e.g., near or within a particular tissue type, e.g., cancer tissue, e.g., prostate cancer tissue), wherein the composition comprises an imaging agent; and detecting (e.g., via PET, X-ray, MRI, CT) the imaging agent.

In another aspect, the invention is directed to a composition (e.g., a pharmaceutical composition) comprising a bombesin/gastrin-releasing peptide receptor ligand (GRP)/chelator construct covalently attached to a macromolecule (e.g., nanoparticle, e.g., polymer, e.g., protein) for use in therapy.

In another aspect, the invention is directed to a composition (e.g., a pharmaceutical composition) comprising a bombesin/gastrin-releasing peptide receptor ligand (GRP)/chelator construct covalently attached to a macromolecule (e.g., nanoparticle, e.g., polymer, e.g., protein) for use in in vivo diagnosis.

In certain embodiments, the macromolecule is a nanoparticle (e.g., an ultrasmall nanoparticle, e.g., a C-dot, e.g., a C'-dot). In certain embodiments, the macromolecule has a diameter no greater than 20 nm (e.g., has a diameter no greater than 15 nm, e.g., has a diameter no greater than 10 nm). In certain embodiments, the macromolecule comprises: a fluorescent silica-based nanoparticle comprising: a silica-based core; a fluorescent compound within the core; a silica shell surrounding a portion of the core; an organic polymer attached to the nanoparticle, thereby coating the nanoparticle, wherein the nanoparticle has a diameter no greater than 20 nm.

In certain embodiments, from 1 to 20 bombesin/gastrin-releasing peptide receptor ligand ligands are attached to the macromolecule.

In certain embodiments, the composition further comprises a radiolabel (e.g., $^{89}$Zr, $^{64}$Cu, $^{68}$Ga, $^{86}$Y, $^{124}$I, $^{177}$Lu, $^{225}$Ac, $^{212}$Pb and $^{211}$At).

In certain embodiments, the chelator comprises a member selected from the group consisting of N,N'-Di(2-hydroxybenzyl)ethylenediamine-N,N-diacetic acid monohydrochloride (HBED-CC), 1,4,7,10-tetraazacyclododecane-1,4,7,10-tetraacetic acid (DOTA), diethylenetriaminepentaacetic (DTPA), desferrioxamine (DFO), and triethylenetetramine (TETA).

In certain embodiments, the composition comprises:

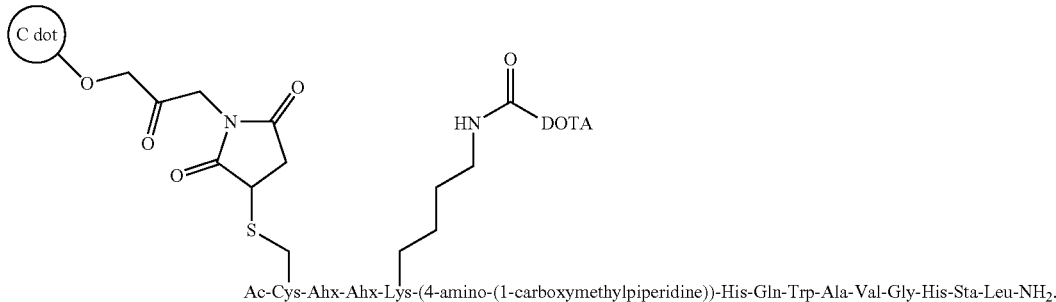

Ac-Cys-Ahx-Ahx-Lys-(4-amino-(1-carboxymethylpiperidine))-His-Gln-Trp-Ala-Val-Gly-His-Sta-Leu-NH$_2$.

In certain embodiments, the composition comprises:

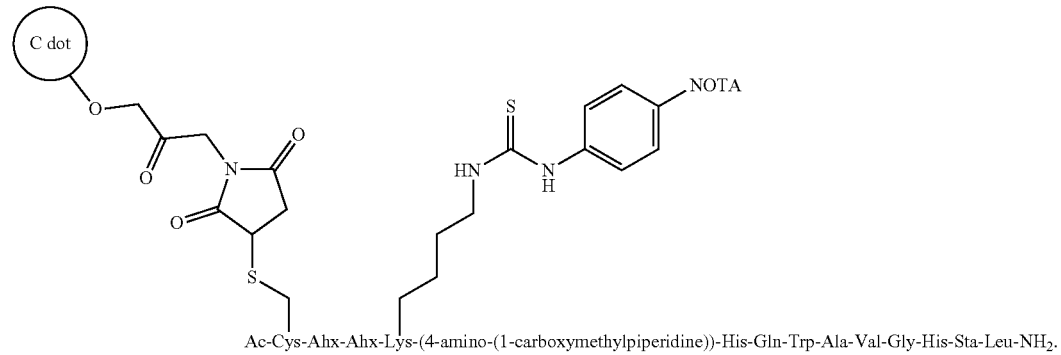

Ac-Cys-Ahx-Ahx-Lys-(4-amino-(1-carboxymethylpiperidine))-His-Gln-Trp-Ala-Val-Gly-His-Sta-Leu-NH$_2$.

Elements of embodiments involving one aspect of the invention (e.g., methods) can be applied in embodiments involving other aspects of the invention, and vice versa.

Definitions

In order for the present disclosure to be more readily understood, certain terms are first defined below. Additional definitions for the following terms and other terms are set forth throughout the specification.

In this application, the use of "or" means "and/or" unless stated otherwise. As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": The term "administration" refers to introducing a substance into a subject. In general, any route of administration may be utilized including, for example, parenteral (e.g., intravenous), oral, topical, subcutaneous, peritoneal, intraarterial, inhalation, vaginal, rectal, nasal, introduction into the cerebrospinal fluid, or instillation into body compartments. In certain embodiments, administration is oral. Additionally or alternatively, in certain embodiments, administration is parenteral. In certain embodiments, administration is intravenous.

"Aliphatic": The term "aliphatic" or "aliphatic group", as used herein, means a straight-chain (e.g., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocyclyl," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocyclyl" or "cycloalkyl") refers to a monocyclic $C_3$-$C_7$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl, or (cycloalkyl)alkenyl.

"Alkylene": The term "alkylene" refers to a bivalent alkyl group. An "alkylene chain" is a polymethylene group, e.g., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent.

"Alkenylene": The term "alkenylene" refers to a bivalent alkenyl group. A substituted alkenylene chain is a polymethylene group containing at least one double bond in which one or more hydrogen atoms are replaced with a substituent.

"Alkynylene": The term "alkynylene" refers to a bivalent alkynyl group. A substituted alkynylene chain is a polymethylene group containing at least one triple bond in which one or more hydrogen atoms are replaced with a substituent.

"Aryl": The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

"Biocompatible": The term "biocompatible", as used herein is intended to describe materials that do not elicit a substantial detrimental response in vivo. In certain embodiments, the materials are "biocompatible" if they are not toxic to cells. In certain embodiments, materials are "biocompatible" if their addition to cells in vitro results in less than or equal to 20% cell death, and/or their administration in vivo does not induce inflammation or other such adverse effects. In certain embodiments, materials are biodegradable.

"Biodegradable": As used herein, "biodegradable" materials are those that, when introduced into cells, are broken down by cellular machinery (e.g., enzymatic degradation) or by hydrolysis into components that cells can either reuse or dispose of without significant toxic effects on the cells. In certain embodiments, components generated by breakdown of a biodegradable material do not induce inflammation and/or other adverse effects in vivo. In certain embodiments, biodegradable materials are enzymatically broken down. Alternatively or additionally, in certain embodiments, biodegradable materials are broken down by hydrolysis. In certain embodiments, biodegradable polymeric materials break down into their component polymers. In certain embodiments, breakdown of biodegradable materials (including, for example, biodegradable polymeric materials) includes hydrolysis of ester bonds. In certain embodiments, breakdown of materials (including, for example, biodegradable polymeric materials) includes cleavage of urethane linkages.

"Bivalent chains": As used herein, the term "bivalent, $C_{1-20}$ (or $C_{1-10}$, $C_{1-6}$, $C_{1-3}$, etc.) saturated or unsaturated, straight or branched, hydrocarbon chain", refers to bivalent alkylene, alkenylene, and alkynylene chains that are straight or branched as defined herein.

"Cancer": As used herein, the term "cancer" refers to a malignant neoplasm or tumor (Stedman's Medical Dictionary, 25th ed.; Hensly ed.; Williams & Wilkins: Philadelphia, 1990). Exemplary cancers include, but are not limited to prostate cancers.

"Carrier": As used herein, "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Halogen": The term "halogen" means F, Cl, Br, or I.

"Heteroaryl": The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

"Heteroatom": The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

"Heterocyclic": As used herein, the terms "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in this context in reference to a ring atom, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

"Natural amino acid": As used herein, the phrase "natural amino acid" refers to any of the 20 amino acids naturally occurring in proteins. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged sidechains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

"Optionally substituted": As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —O$(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —OC(O)$(CH_2)_{0-4}SR^\circ$; —SC(S)$SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —SC(S)$SR^\circ$; —$(CH_2)_{0-4}OC(O)NR^\circ_2$; —C(O)N(OR$^\circ$)R$^\circ$; —C(O)C(O)R$^\circ$; —C(O)$CH_2$C(O)R$^\circ$; —C(NOR$^\circ$)R$^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —N(R$^\circ$)S(O)$_2$NR$^\circ_2$; —N(R$^\circ$)S(O)$_2$R$^\circ$; —N(OR$^\circ$)R$^\circ$; —C(NH)NR$^\circ_2$; —P(O)$_2$R$^\circ$; —P(O)R$^\circ_2$; —OP(O)R$^\circ_2$; —OP(O)(OR$^\circ$)$_2$; SiR$^\circ_3$; —(C$_{1-4}$ straight or branched)alkylene)O—N(R$^\circ$)$_2$; or —(C$_{1-4}$ straight or branched)alkylene)C(O)O—N(R$^\circ$)$_2$, wherein each $R^\circ$ may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●{}_2$, —NO$_2$, —SiR$^●{}_3$, —OSiR$^●{}_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●{}_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†{}_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†{}_2$, —C(S)NR$^†{}_2$, —C(NH)NR$^†{}_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●{}_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

"Oxo": The term "oxo," as used herein, means an oxygen that is double bonded to a carbon atom, thereby forming a carbonyl.

"Partially unsaturated": As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

"Peptide" or "Polypeptide": The term "peptide" or "polypeptide" refers to a string of at least two (e.g., at least three) amino acids linked together by peptide bonds. In certain embodiments, a polypeptide comprises naturally-occurring amino acids; alternatively or additionally, in certain embodiments, a polypeptide comprises one or more non-natural amino acids (e.g., compounds that do not occur in nature but that can be incorporated into a polypeptide chain; see, for example, http://www.cco.caltech.edu/~dadgrp/Unnatstruct-.gif, which displays structures of non-natural amino acids that have been successfully incorporated into functional ion channels) and/or amino acid analogs as are known in the art may alternatively be employed). In certain embodiments, one or more of the amino acids in a protein may be modified, for example, by the addition of a chemical entity such as a carbohydrate group, a phosphate group, a farnesyl group, an isofarnesyl group, a fatty acid group, a linker for conjugation, functionalization, or other modification, etc.

"Protecting group": One of ordinary skill in the art will appreciate that compound and synthetic methods, as described herein, may utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. Amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido) propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo) benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl) ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino) acetamide, 3-(p-hydroxyphenyl)propanamide, 3-(o-nitrophenyl)propanamide, 2-methyl-2-(o-nitrophenoxy) propanamide, 2-methyl-2-(o-phenylazophenoxy) propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fern), N-2-picolylamino N'-oxide, N-1,1-dimethylthiomethyleneamine, N-benzylideneamine, N-p-methoxybenzylideneamine, N-diphenylmethyleneamine, N-[(2-pyridyl) mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide. Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups, including protecting groups for carboxyl groups, are described by Greene and Wuts (supra).

"Radiolabel": As used herein, "radiolabel" refers to a moiety comprising a radioactive isotope of at least one element. Exemplary suitable radiolabels include but are not limited to those described herein. In certain embodiments, a radiolabel is one used in positron emission tomography (PET). In certain embodiments, a radiolabel is one used in single-photon emission computed tomography (SPECT). In some embodiments, a non-limiting list of radionuclides includes $^{99m}$Tc, $^{111}$In, $^{64}$Cu, $^{67}$Ga, $^{68}$Ga, $^{186}$Re, $^{188}$Re, $^{153}$Sm, $^{177}$Lu, $^{67}$Cu, $^{123}$I, $^{124}$I, $^{125}$I, $^{126}$I, $^{131}$I, $^{11}$C, $^{13}$N, $^{15}$O, $^{18}$F, $^{153}$Sm, $^{166}$Ho, $^{177}$Lu, $^{149}$Pm, $^{90}$Y, $^{213}$Bi, $^{103}$Pd, $^{109}$Pd, $^{159}$Gd, $^{140}$La, $^{198}$Au, $^{199}$Au, $^{169}$Yb, $^{175}$Yb, $^{165}$Dy, $^{166}$Dy, $^{105}$Rh, $^{111}$Ag, $^{89}$Zr, $^{225}$Ac, $^{82}$Rb, $^{75}$Br, $^{76}$Br, $^{77}$Br, $^{80}$Br, $^{80m}$Br, $^{82}$Br, $^{83}$Br, $^{211}$At and $^{192}$Ir.

"Subject": As used herein, the term "subject" includes humans and mammals (e.g., mice, rats, pigs, cats, dogs, and horses). In many embodiments, subjects are mammals, particularly primates, especially humans. In certain embodiments, subjects are livestock such as cattle, sheep, goats, cows, swine, and the like; poultry such as chickens, ducks, geese, turkeys, and the like; and domesticated animals particularly pets such as dogs and cats. In certain embodiments (e.g., particularly in research contexts) subject mammals will be, for example, rodents (e.g., mice, rats, hamsters), rabbits, primates, or swine such as inbred pigs and the like.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Therapeutic agent": As used herein, the phrase "therapeutic agent" refers to any agent that has a therapeutic effect and/or elicits a desired biological and/or pharmacological effect, when administered to a subject.

"Treatment": As used herein, the term "treatment" (also "treat" or "treating") refers to any administration of a substance that partially or completely alleviates, ameliorates, relives, inhibits, delays onset of, reduces severity of, and/or reduces incidence of one or more symptoms, features, and/or causes of a particular disease, disorder, and/or condition. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In certain embodiments, treatment may be of a subject who has been diagnosed as suffering from the relevant disease, disorder, and/or condition. In certain embodiments, treatment may be of a subject known to have one or more susceptibility factors that are statistically correlated with increased risk of development of the relevant disease, disorder, and/or condition. In certain embodiments, treatment comprises delivery of therapeutics, including but not limited to, small molecule delivery, radiotherapy, immunotherapy, intrinsic therapeutic properties (e.g., ferroptosis), and particle-driven regulation of the tumor microenvironment. In certain embodiments, therapeutics are attached to particles, such as those described herein.

"Unnatural amino acid": As used herein, the phrase "unnatural amino acid" refers to amino acids not included in the list of 20 amino acids naturally occurring in proteins, as described above. Such amino acids include the D-isomer of any of the 20 naturally occurring amino acids. Unnatural amino acids also include 6-aminohexanoic acid, homoserine, ornithine, norleucine, and thyroxine. Other unnatural amino acids are well known to one of ordinary skill in the art and include unnatural aliphatic side chains. Other unnatural amino acids include modified amino acids, including those that are N-alkylated, cyclized, phosphorylated, acetylated, amidated, azidylated, labelled, and the like. In some embodiments, an unnatural amino acid is a D-isomer. In some embodiments, an unnatural amino acid is a L-isomer.

"Unsaturated": The term "unsaturated," as used herein, means that a moiety has one or more units of unsaturation.

Drawings are presented herein for illustration purposes, not for limitation.

BRIEF DESCRIPTION OF DRAWINGS

The foregoing and other objects, aspects, features, and advantages of the present disclosure will become more apparent and better understood by referring to the following description taken in conduction with the accompanying drawings, in which:

FIG. 5 shows an exemplary minimal structure, according to an illustrative embodiment of the invention. From the structure shown in FIG. 5, any number of chelators on the dLys and linkers to the C dot (or other macromolecule) can be added. For example, NOTA and/or DOTA analogs can be made from this intermediate structure. Furthermore, a PEG spacer instead of a (Ahx)2 spacer can be attached. In certain embodiments, the appropriately protected dLys is selected to update the spacer.

FIGS. 8A and 8B show administration of 0.5 mCi $^{67}$Ga-NOTA-PSMAi-C dot (FIG. 8A) or co-injection of 0.5 mCi $^{67}$Ga-NOTA-PSMAi-C and 2-(phosphonomethyl)pentanedioic acid (PMPA) (160 µg/20 g) (FIG. 8B) in a mouse model. PMPA is a black that shows a reduction in uptake of $^{67}$Ga-NOTA-PSMAi-C dot, demonstrating specificity and confirming the results presenting in the in vitro data presented in FIG. 6A.

FIG. 9A shows an illustration of C' dots functionalized with different NIR fluorescent dyes (Cy5.5 and CW800) and targeting peptide (GRP-DOTA). Different NIR fluorescent dyes can also be used with PSMAi-NOTA targeting peptide according to certain embodiments described herein.

FIGS. 9B-9D show FCS correlation, curve and fit (FIG. 1B), UV-vis absorbance spectra (FIG. 1C) and GPC elugram with Gaussian fit (FIG. 9D) of PSMAi-NOTA-PEG-Cy5.5-C' dots. TEM of the samples is show in in the inset of FIG. 9B.

FIG. 16A shows multiplexed detection of nodal metastases, using spectrally-distinct particle probes. Figure discloses "cRGDY" as SEQ ID NO: 1.

FIGS. 16B-16C show specific binding/accumulation of αMSH-Cy5.5- and cRGDY-CW800-C'dots ("cRGDY" disclosed as SEQ ID NO: 1) in a representative high tumor burden lymph node (FIG. 16A; row 3) with correlative histopathology, including (FIG. 16B) H&E staining, fluorescence microscopy, and (FIG. 16C) immunohistochemistry (IHC) for melanoma markers (αv-integrins and MiTF) in nodal and tumor tissue.

FIG. 23A shows an autoradiogram.
FIG. 23B shows H&E staining.
FIGS. 23C and 23D show PSMA MC (other sample).
FIG. 24A shows a GPRr autoradiography.
FIG. 24B shows H&E staining of the same sample.

DETAILED DESCRIPTION

Figure 1A:
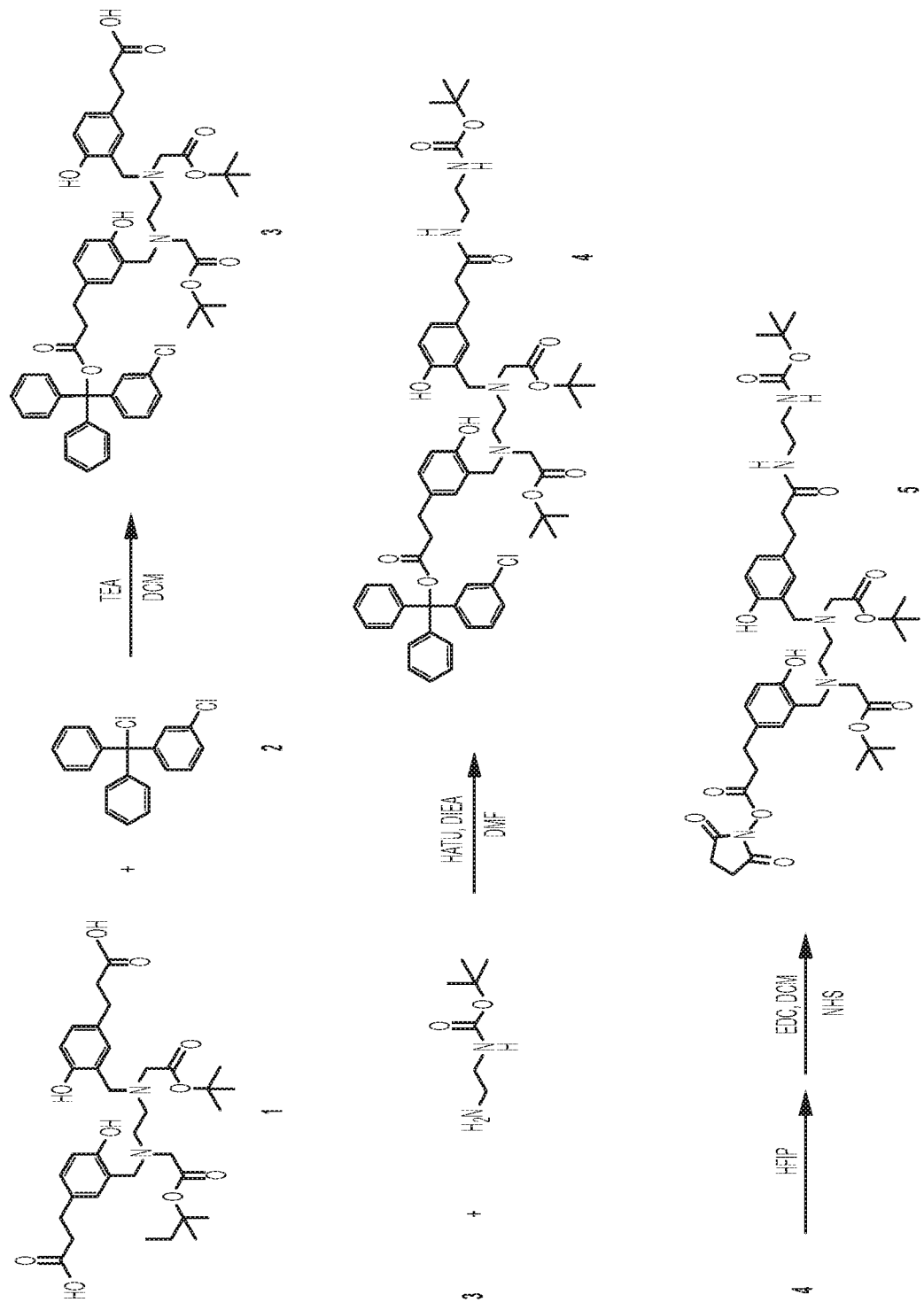
FIGS. 1A-1B is a schematic of a synthetic route used to obtain a modified form of PSMAi-HBED-CC, which was successfully conjugated onto a nanoparticle, according to an illustrative embodiment of the invention.

Throughout the description, where compositions are described as having, including, or comprising specific components, or where methods are described as having, including, or comprising specific steps, it is contemplated that, additionally, there are compositions of the present invention that consist essentially of, or consist of, the recited components, and that there are methods according to the present invention that consist essentially of, or consist of, the recited processing steps.

It should be understood that the order of steps or order for performing certain action is immaterial so long as the invention remains operable. Moreover, two or more steps or actions may be conducted simultaneously.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein is the development of conjugates where constructs containing a PSMA inhibitor and metal chelator are covalently attached to a macromolecule (e.g., a nanoparticle, a polymer, a protein). Such conjugates may exhibit enhancements in binding and cell uptake properties (e.g., due to multivalency) and pharmacokinetics (e.g., due to increased molecular weight or size) over the free, unbound PSMA inhibitor/chelator construct. For example, PSMA inhibitor displayed on a macromolecule (e.g., nanoparticle) surface has reduced kidney uptake compared with free, unbound PSMA inhibitor constructs.

Details of various embodiments applicable to the systems and methods described herein are also provided in, for example, PCT/US14/30401 (WO 2014/145606) by Bradbury et al., PCT/US16/26434 ("Nanoparticle Immunoconjugates", filed Apr. 7, 2016) by Bradbury et al., PCT/US14/73053 (WO2015/103420) by Bradbury et al., PCT/US15/65816 (WO 2016/100340) by Bradbury et al., PCT/US16/34351 ("Methods and Treatment Using Ultrasmall Nanoparticles to Induce Cell Death of Nutrient-Deprived Cancer Cells via Ferroptosis", filed May 26, 2016) by Bradbury et al., U.S. 62/267,676 ("Compositions Comprising Cyclic Peptides, and Use of Same for Visual Differentiation of Nerve Tissue During Surgical Procedures" filed Dec. 15, 2015) by Bradbury et al., U.S. 62/330,029 ("Compositions and Methods for Targeted Particle Penetration, Distribution, and Response in Malignant Brain Tumors," filed Apr. 29, 2016) by Bradbury et al., U.S. Ser. No. 14/588,066 "Systems, methods, and apparatus for multi-channel imaging of fluorescent sources in real time" by Bradbury et al., and U.S. 62/349,538 ("Imaging Systems and Methods for Lymph Node Differentiation and/or Nerve Differentiation, e.g., for Intraoperative Visualization," filed Jun. 13, 2016) by Bradbury et al., the contents of which are hereby incorporated by reference in their entireties. In certain embodiments, conjugates of the invention are a composition comprising a targeting peptide/chelator construct covalently attached to a macromolecule. In certain embodiments, the targeting peptide comprises a prostate specific membrane antigen inhibitor (PSMAi). In certain embodiments, the targeting peptide comprises a bombesin/gastrin-releasing peptide receptor ligand (GRP).

In certain embodiments, PSMAi conjugates of the invention are of the formula:

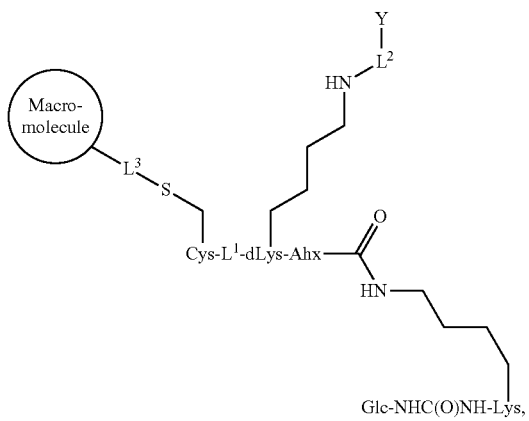

wherein:
$L^1$ is a peptidic fragment comprising from 1 to about 10 natural or unnatural amino acid residues, or an optionally substituted, bivalent, $C_{1-20}$ saturated or unsaturated, straight or branched, hydrocarbon chain, wherein one or more methylene units of the hydrocarbon chain are optionally and independently replaced by —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;
$L^2$ is an optionally substituted, bivalent, $C_{1-10}$ saturated or unsaturated, straight or branched, hydrocarbon chain, wherein one or more methylene units of the hydrocarbon chain are optionally and independently replaced by -Cy-, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;
$L^3$ is a covalent bond or a crosslinker derived from a bifunctional crosslinking reagent capable of conjugating a reactive moiety on the (PSMAi)/chelator construct with a moiety of the macromolecule;
each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
Y is a chelator moiety; and
R is hydrogen, $C_{1-6}$ alkyl, or a nitrogen protecting group;
wherein each amino acid residue, unless otherwise indicated, may be protected or unprotected on its terminus and/or side chain group.

It will be appreciated that throughout this disclosure, where a macromolecule (either generically or specifically) is drawn schematically as part of a conjugate, e.g.

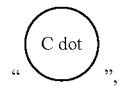

such schematic encompasses a suitable linking moiety between the macromolecule and its depicted attachment to the remainder of the conjugate.

In certain embodiments, a bombesin/gastrin-releasing peptide receptor ligand (GRP)/chelator construct comprises a peptide of the sequence:

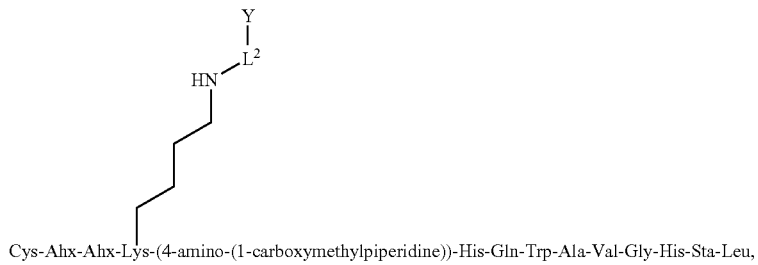

wherein,
$L^2$ is an optionally substituted, bivalent, $C_{1-10}$ saturated or unsaturated, straight or branched, hydrocarbon chain, wherein one or more methylene units of the hydrocarbon chain are optionally and independently replaced by -Cy-, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;
each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
Y is a chelator moiety; and
R is hydrogen, $C_{1-6}$ alkyl, or a nitrogen protecting group;
wherein each amino acid residue, unless otherwise indicated, may be protected or unprotected on its terminus and/or side chain group.

In some embodiments, a bombesin/gastrin-releasing peptide receptor ligand (GRP)/chelator construct is covalently attached via the depicted cysteine residue to a macromolecule through a crosslinker, $L^3$, wherein $L^3$ is a covalent bond or a crosslinker derived from a bifunctional crosslinking reagent capable of conjugating a reactive moiety on the bombesin/gastrin-releasing peptide receptor ligand (GRP)/chelator construct with a reactive moiety of the macromolecule.

It will be appreciated that throughout this disclosure, unless otherwise specified, amino acid side chain groups or termini are optionally protected with a suitable protecting group.

In some embodiments, $L^1$ is a peptidic fragment comprising 1, 2, 3, 4, 5, 6, 7, 8, 9, or 10 natural or unnatural amino acid residues. In some embodiments, $L^1$ is a peptidic fragment comprising 1, 2, 3, 4, or 5 natural or unnatural amino acid residues. In some embodiments, $L^1$ is a peptidic fragment comprising 1, 2, or 3 natural or unnatural amino acid residues. In some embodiments, $L^1$ is a peptidic fragment comprising 2 unnatural amino acid residues. In some embodiments, $L^1$ comprises one or two units of 6-aminohexanoic acid (Ahx). In some embodiments, $L^1$ is -Ahx-Ahx-.

In some embodiments, $L^1$ is an optionally substituted $C_{1-10}$ saturated or unsaturated, straight or branched, hydrocarbon chain, wherein one or more methylene units of the hydrocarbon chain are optionally and independently replaced by —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—. In some embodiments, $L^1$ is a $C_{1-10}$ saturated or unsaturated, straight or branched, hydrocarbon chain, wherein one or more methylene units of the hydrocarbon chain are optionally and independently replaced by —NR—, —O—, or —C(O)—. In some embodiments, $L^1$ comprises one or more units of ethylene glycol. In certain embodiments, L' comprises one or more units of —(CH/CH$_2$)— or —(OCH$_2$CH$_2$)—.

In certain embodiments, $L^2$ is a $C_{1-6}$ saturated or unsaturated, straight or branched, hydrocarbon chain, wherein one or more methylene units of the hydrocarbon chain are optionally and independently replaced by -Cy-, —NR—, —N(R)C(O)—, —C(O)N(R)—, —O—, —C(O)—, —OC(O)—, or —C(O)O—. In certain embodiments, $L^2$ is a $C_{1-3}$ saturated or unsaturated, straight or branched, hydrocarbon chain, wherein one or more methylene units of the hydrocarbon chain are optionally and independently replaced by -Cy-, —NR—, —N(R)C(O)—, —C(O)N(R)—, —O—, —C(O)—, —OC(O)—, or —C(O)O—. In certain embodiments, $L^2$ is a $C_{1-3}$ saturated or unsaturated, straight or branched, hydrocarbon chain, wherein one, two, or three, methylene units of the hydrocarbon chain are optionally and independently replaced by -Cy-, —NR—, or —C(O)—. In some embodiments, $L^2$ is —C(O)— or —C(O)NH-Cy-.

One of ordinary skill in the art will be familiar with a multitude of suitable crosslinking reagents for use in accordance with the provided methods. Such suitable crosslinking reagents are described in Hermanson, G. T. (2008). Bioconjugate Techniques. 2nd edition, Academic Press, New York. In certain embodiments, a crosslinking reagent is a heterobifunctional reagent. In certain embodiments, a crosslinking reagent is a homobifunctional reagent. In some embodiments, a bifunctional crosslinking reagent is selected from
  i) maleimides (Bis-Maleimidoethane, 1,4-bismaleimidobutane, bismaleimidohexane, Tris[2-maleimidoethyl]amine, 1,8-bis-Maleimidodiethyleneglycol, 1,11-bis-Maleimidodiethyleneglycol, 1,4 bismaleimidyl-2,3-dihydroxybutane, Dithio-bismaleimidoethane),
  ii) pyridyldithiols (1,4-Di-[3'-(2'-pyridyldithio)-propionamido]butane),
  iii) aryl azides (Bis-[b-(4-Azidosalicylamido)ethyl]disulfide),
  iv) NHS ester/maleimides (N-(a-Maleimidoacetoxy) succinimide ester, N-[β-Maleimidopropyloxy]succinimide ester, N-[g-Maleimidobutyryloxy]succinimide ester, N-[g-Maleimidobutyryloxy]sulfosuccinimide ester, m-Maleimidobenzoyl-N-hydroxysuccinimide ester, m-Maleimidobenzoyl-N-hydroxysulfosuccinimide ester, Succinimidyl 4[N-maleimidomethyl]cyclohexane-1-carboxylate, Sulfosuccinimidyl 4[N-maleimidomethyl]cyclohexane-1-carboxylate, [N-e-Maleimidocaproyloxy]succinimide ester, [N-e-Maleimidocaproyloxy]sulfosuccinimide ester Succinimidyl 4-[p-maleimidophenyl]butyrate, Sulfosuccinimidyl 4-[p-maleimidophenyl]butyrate, Succinimidyl-6-[β-maleimidopropionamido]hexanoate, Succinimidyl-4-[N-Maleimidomethyl]cyclohexane-1-carboxy-[6-amidocaproate], N-[k-Maleimidoundecanoyloxy]sulfosuccinimide ester, succinimidyl-([N-maleimidopropionamido]-#ethyleneglycol) ester),
  v) NHS ester/pyridyldithiols (4-Succinimidyloxycarbonyl-methyl-a-[2-pyridyldithio]toluene, 4-Sulfosuccinimidyl-6-methyl-α-(2-pyridyldithio)toluamidohexanoate),
  vi) NHS ester/haloacetyls (N-Succinimidyl iodoacetate, Succinimidyl 3-[bromoacetamido]propionate, N-Succinimidyl[4-iodoacetyl]aminobenzoate, N-Sulfosuccinimidyl[4-iodoacetyl]aminobenzoate),
  vii) pyridyldithiol/aryl azides (N-[4-(p-Azidosalicylamido) butyl]-3'-(2'-pyridyldithio)propionamide),
  viii) maleimide/hydrazides (N-[β-Maleimidopropionic acid] hydrazide, trifluoroacetic acid salt, [N-e-Maleimidocaproic acid] hydrazide, trifluoroacetic acid salt, 4-(4-N-Maleimidophenyl)butyric acid hydrazide hydrochloride, N-[k-Maleimidoundecanoic acid]hydrazide),
  ix) pyridyldithiol/hydrazides (3-(2-Pyridyldithio)propionyl hydrazide),
  x) isocyanate/maleimides (N-[p-Maleimidophenyl]isocyanate), and 1,6-Hexane-bis-vinylsulfone, to name but a few.

In certain embodiments of the methods, peptides, and conjugates described above, a crosslinker is a moiety derived from a bifunctional crosslinking reagent as described above. In some embodiments, a crosslinker is a moiety derived from a bifunctional crosslinking reagent capable of conjugating a surface amine of a macromolecule and a sulfhydryl of a targeting peptide. In certain embodiments, a crosslinker is a moiety derived from a bifunctional crosslinking reagent capable of conjugating a surface hydroxyl of a macromolecule and a sulfhydryl of a targeting peptide. In some embodiments, a crosslinker is a moiety derived from a bifunctional crosslinking reagent capable of conjugating a surface sulfhydryl of a macromolecule and a thiol of a targeting peptide. In some embodiments, a crosslinker is a moiety derived from a bifunctional crosslinking reagent capable of conjugating a surface carboxyl of a macromolecule and a sulfhydryl of a targeting peptide. In some embodiments, a crosslinker is a moiety having the structure:

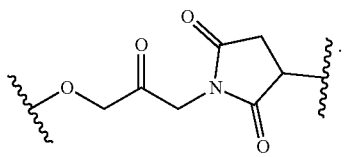 [SMILES: *OCC(=O)CN1C(=O)CC(*)C1=O]

In certain embodiments, $L^3$ is a covalent bond. In certain embodiments, $L^3$ is a crosslinker derived from a bifunctional crosslinking reagent capable of conjugating a reactive moiety of the (PSMAi)/chelator construct with a reactive moiety of the macromolecule. In certain embodiments, $L^3$ is a crosslinker derived from a bifunctional crosslinking reagent capable of conjugating a reactive moiety of the bombesin/gastrin-releasing peptide receptor ligand (GRP)/chelator construct with a reactive moiety of the macromolecule. In certain embodiments, $L^3$ is a crosslinker derived from a bifunctional crosslinking reagent capable of conjugating a sulfhydryl of the bombesin/gastrin-releasing peptide receptor ligand (GRP)/chelator construct with a reactive moiety of the macromolecule. In certain embodiments, the bifunctional crosslinking reagent is a maleimide or haloacetyl. In certain embodiments, the bifunctional crosslinking reagent is a maleimide.

In some embodiments, each -Cy- is independently an optionally substituted 5-8 membered bivalent, saturated, partially unsaturated, or aryl ring having 0-4 heteroatoms independently selected from nitrogen, oxygen, or sulfur. In some embodiments, each -Cy- is independently an optionally substituted 6-membered bivalent, saturated, partially unsaturated, or aryl ring having 0-4 heteroatoms independently selected from nitrogen, oxygen, or sulfur. In some embodiments, -Cy- is phenylene.

In certain embodiments, the nanoparticle comprises silica, polymer (e.g., poly(lactic-co-glycolic acid) (PLGA)), biologics (e.g., protein carriers), and/or metal (e.g., gold, iron). In certain embodiments, the nanoparticle is a "C dot" or "C' dot" as described in U.S. Publication No. 2013/0039848 A1 by Bradbury et al. (see Appendix A), which is hereby incorporated by reference herein in its entirety.

In certain embodiments, the nanoparticle is spherical. In certain embodiments, the nanoparticle is non-spherical. In certain embodiments, the nanoparticle is or comprises a material selected from the group consisting of metal/semi-metal/non-metals, metal/semi-metal/non-metal-oxides, -sulfides, -carbides, -nitrides, liposomes, semiconductors, and/or combinations thereof. In certain embodiments, the metal is selected from the group consisting of gold, silver, copper, and/or combinations thereof.

The nanoparticle may comprise metal/semi-metal/non-metal oxides including silica ($SiO_2$), titania ($TiO_2$), alumina ($Al_2O_3$), zirconia ($Z_rO2$), germania ($GeO_2$), tantalum pentoxide ($Ta_2O_5$), $NbO_2$, etc., and/or non-oxides including metal/semi-metal/non-metal borides, carbides, sulfide and nitrides, such as titanium and its combinations (Ti, $TiB_2$, TiC, TiN, etc.).

The nanoparticle may comprise one or more polymers, e.g., one or more polymers that have been approved for use in humans by the U.S. Food and Drug Administration (FDA) under 21 C.F.R. § 177.2600, including, but not limited to, polyesters (e.g., polylactic acid, poly(lactic-co-glycolic acid), polycaprolactone, polyvalerolactone, poly(1,3-dioxan-2-one)); polyanhydrides (e.g., poly(sebacic anhydride)); polyethers (e.g., polyethylene glycol); polyurethanes; polymethacrylates; polyacrylates; polycyanoacrylates; copolymers of PEG and poly(ethylene oxide) (PEO).

The nanoparticle may comprise one or more degradable polymers, for example, certain polyesters, polyanhydrides, polyorthoesters, polyphosphazenes, polyphosphoesters, certain polyhydroxyacids, polypropylfumerates, polycaprolactones, polyamides, poly(amino acids), polyacetals, polyethers, biodegradable polycyanoacrylates, biodegradable polyurethanes and polysaccharides. For example, specific biodegradable polymers that may be used include but are not limited to polylysine, poly(lactic acid) (PLA), poly (glycolic acid) (PGA), poly(caprolactone) (PCL), poly(lactide-co-glycolide) (PLG), poly(lactide-co-caprolactone) (PLC), and poly(glycolide-co-caprolactone) (PGC). Another exemplary degradable polymer is poly (beta-amino esters), which may be suitable for use in accordance with the present application.

In certain embodiments, a nanoparticle can have or be modified to have one or more functional groups. Such functional groups (within or on the surface of a nanoparticle) can be used for association with any agents (e.g., detectable entities, targeting entities, therapeutic entities, or PEG). In addition to changing the surface charge by introducing or modifying surface functionality, the introduction of different functional groups allows the conjugation of linkers (e.g., (cleavable or (bio-)degradable) polymers such as, but not limited to, polyethylene glycol, polypropylene glycol, PLGA, etc.), targeting/homing agents, and/or combinations thereof.

The number of ligands attached to the nanoparticle may range from about 1 to about 20, from about 2 to about 15, from about 3 to about 10, from about 1 to about 10, or from about 1 to about 6. The small number of the ligands attached to the nanoparticle helps maintain the hydrodynamic diameter of the present nanoparticle which meet the renal clearance cutoff size range. Hilderbrand et al., Near-infrared fluorescence: application to in vivo molecular imaging, Curr. Opin. Chem. Biol., 14:71-9, 2010.

In certain embodiments, therapeutic agents other than PSMAi may be attached to the nanoparticle. The therapeutic agents include antibiotics, antimicrobials, antiproliferatives, antineoplastics, antioxidants, endothelial cell growth factors, thrombin inhibitors, immunosuppressants, anti-platelet aggregation agents, collagen synthesis inhibitors, therapeutic antibodies, nitric oxide donors, antisense oligonucleotides, wound healing agents, therapeutic gene transfer constructs, extracellular matrix components, vasodialators, thrombolytics, anti-metabolites, growth factor agonists, antimitotics, statin, steroids, steroidal and non-steroidal anti-inflammatory agents, angiotensin converting enzyme (ACE) inhibitors, free radical scavengers, PPAR-gamma agonists, small interfering RNA (siRNA), microRNA, and anti-cancer chemotherapeutic agents. The therapeutic agents encompassed by the present embodiment also include radionuclides, for example, $^{90}Y$, $^{131}I$ and $^{177}Lu$. The therapeutic agent may be radiolabeled, such as labeled by binding to radiofluorine $^{18}F$.

Cancers that may be treated include, for example, any cancer. In certain embodiments, the cancers are prostate cancers.

In certain embodiments, a contrast agent may be attached to the present nanoparticle for medical or biological imaging. In certain embodiments may include positron emission tomography (PET), single photon emission computed tomography (SPECT), computerized tomography (CT), magnetic resonance imaging (MRI), optical bioluminescence imaging, optical fluorescence imaging, and combinations thereof. In certain embodiments, the contrast agent can be any molecule, substance or compound known in the art for PET, SPECT, CT, MRI, and optical imaging. The contrast agent may be radionuclides, radiometals, positron emitters, beta emitters, gamma emitters, alpha emitters, paramagnetic metal ions, and supraparamagnetic metal ions. The contrast agents include, but are not limited to, iodine, fluorine, Cu, Zr, Lu, At, Yt, Ga, In, Tc, Gd, Dy, Fe, Mn, Ba and $BaSO_4$. The radionuclides that may be used as the contrast agent attached to the nanoparticle of the present embodiment include, but are not limited to, $^{89}Zr$, $^{64}Cu$, $^{68}Ga$, $^{86}Y$, $^{124}I$, $^{177}Lu$, $^{225}Ac$, $^{212}Pb$, and $^{211}At$. Alternatively, a contrast agent may be indirectly conjugated to the nanoparticle, by attaching to linkers or chelators. The chelators may be adapted to bind a radionuclide. The chelators that can be attached to the present nanoparticle may include, but are not limited to, N,N'-Bis(2-hydroxy-5-(carboxyethyl)-benzyl) ethylenediamine-N,N'-diacetic acid (HBED-CC), 1,4,7,10-tetraazacyclododecane-1,4,7,10-tetraacetic acid (DOTA), diethylenetriaminepentaacetic (DTPA), desferrioxamine (DFO), 1,4,7-triazacyclononane-N,N',N"-triacetic acid (NOTA), and triethylenetetramine (TETA).

In certain embodiments, conjugates of the invention are of the formula:

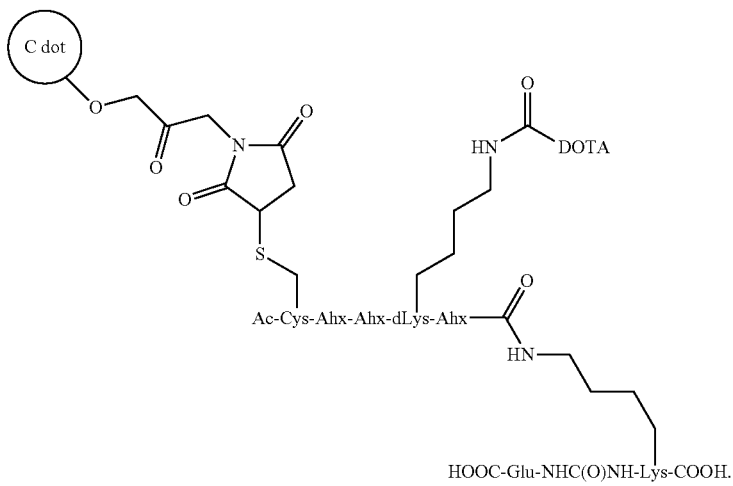

In certain embodiments, conjugates of the invention are of the formula:

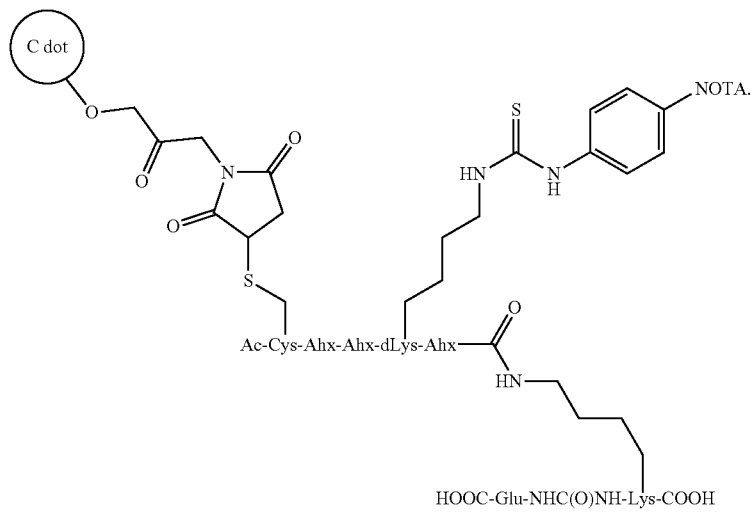

In certain embodiments, conjugates of the invention are of the formula:

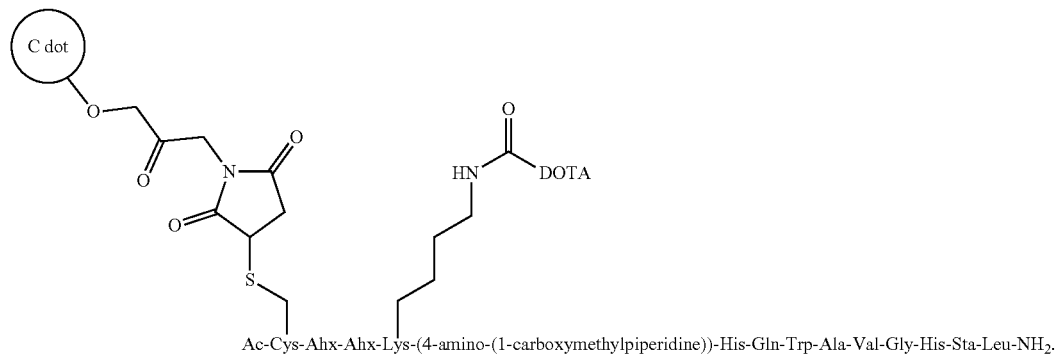

Ac-Cys-Ahx-Ahx-Lys-(4-amino-(1-carboxymethylpiperidine))-His-Gln-Trp-Ala-Val-Gly-His-Sta-Leu-NH$_2$.

In certain embodiments, conjugates of the invention are of the formula:

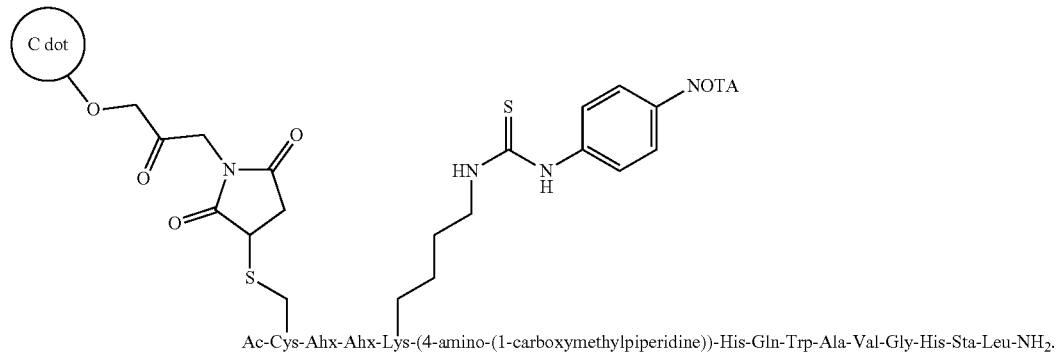

Ac-Cys-Ahx-Ahx-Lys-(4-amino-(1-carboxymethylpiperidine))-His-Gln-Trp-Ala-Val-Gly-His-Sta-Leu-NH$_2$.

In certain embodiments, a probe species comprises nanoparticles. In certain embodiments, the nanoparticles have a silica architecture and dye-rich core. In certain embodiments, the dye rich core comprises a fluorescent reporter. In certain embodiments, the fluorescent reporter is a near infrared or far red dye. In certain embodiments, the fluorescent reporter is selected from the group consisting of a fluorophore, fluorochrome, dye, pigment, fluorescent transition metal, and fluorescent protein. In certain embodiments, the fluorescent reporter is selected from the group consisting of Cy5, Cy5.5, Cy2, FITC, TRITC, Cy7, FAM, Cy3, Cy3.5, Texas Red, ROX, HEX, JA133, AlexaFluor 488, AlexaFluor 546, AlexaFluor 633, AlexaFluor 555, AlexaFluor 647, DAPI, TMR, R6G, GFP, enhanced GFP, CFP, ECFP, YFP, Citrine, Venus, YPet, CyPet, AMCA, Spectrum Green, Spectrum Orange, Spectrum Aqua, Lissamine and Europium. In certain embodiments, imaging is performed in normal lighting settings. In certain embodiments, imaging is performed with some to zero levels of ambient lighting settings.

The imaging methods herein can be used with a number of different fluorescent probe species (or, as in embodiments using a tandem bioluminescent reporter/fluorescent probe, the fluorescent species thereof), for example, (1) probes that become activated after target contact (e.g., binding or interaction) (Weissleder et al., *Nature Biotech.*, 17:375-378, 1999; Bremer et al., *Nature Med.*, 7:743-748, 2001; Campo et al., *Photochem. Photobiol.* 83:958-965, 2007); (2) wavelength shifting beacons (Tyagi et al., *Nat. Biotechnol.*, 18:1191-1196, 2000); (3) multicolor (e.g., fluorescent) probes (Tyagi et al., *Nat. Biotechnol.*, 16:49-53, 1998); (4) probes that have high binding affinity to targets, e.g., that remain within a target region while non-specific probes are cleared from the body (Achilefu et al., *Invest. Radiol.*, 35:479-485, 2000; Becker et al., *Nature Biotech.* 19:327-331, 2001; Bujai et al., *J. Biomed. Opt.* 6:122-133, 2001; Ballou et al. *Biotechnol. Prog.* 13:649-658, 1997; and Neri et al., *Nature Biotech* 15:1271-1275, 1997); (5) quantum dot or nanoparticle-based imaging probes, including multivalent imaging probes, and fluorescent quantum dots such as amine T2 MP EviTags® (Evident Technologies) or Qdot® Nanocrystals (Invitrogen™); (6) non-specific imaging probes e.g., indocyanine green, AngioSense® (VisEn Medical); (7) labeled cells (e.g., such as cells labeled using exogenous fluorophores such as VivoTag™ 680, nanoparticles, or quantum dots, or by genetically manipulating cells to express fluorescent or luminescent proteins such as green or red fluorescent protein; and/or (8) X-ray, MR, ultrasound, PET or SPECT contrast agents such as gadolinium, metal oxide nanoparticles, X-ray contrast agents including iodine based imaging agents, or radioisotopic form of metals such as copper, gallium, indium, technetium, yttrium, and lutetium including, without limitation, 99m-Tc, 111-In, 64-Cu, 67-Ga, 186-Re, 188-Re, 153-Sm, 177-Lu, and 67-Cu. The relevant text of the above-referenced documents are incorporated by reference herein. Another group of suitable imaging probes are lanthanide metal-ligand probes. Fluorescent lanthanide metals include europium and terbium. Fluorescence properties of lanthanides are described in Lackowicz, 1999, Principles of Fluorescence Spectroscopy, $2^{nd}$ Ed., Kluwar Academic, New York, the relevant text incorporated by reference herein. In the methods of this embodiment, the imaging probes can be administered systemically or locally by injecting an imaging probe or by topical or other local administration routes, such as "spraying". Furthermore, imaging probes used in the embodiment of this invention can be conjugated to molecules capable of eliciting photodynamic therapy. These include, but are not limited to, Photofrin, Lutrin, Antrin, aminolevulinic acid, hypericin, benzoporphyrin derivative, and select porphyrins. In certain embodiments, two or more probe species are graphically distinguished, e.g., are displayed with different colors (e.g., green and red, e.g., green and blue), to separately represent the two lymphatic drainage pathways and/or nodes. In certain embodiments, the representations of two or more probe species are superimposed on a graphical display, or the overlapping portion is represented with a different (e.g., a third) color (e.g., yellow). For example, for a lymphatic drainage pathway that both drains the extremity and leads to the tumor site, the pathway may contain both first and second probe species (corresponding, respectively, to a first and second color on the display), and the region of overlap on the display is assigned a new color different from the first and second color. The color may indicate that the associated node should not be removed, to avoid lymphedema.

In general, fluorescent quantum dots used in the practice of the elements of this invention are nanocrystals containing several atoms of a semiconductor material (including but not limited to those containing cadmium and selenium, sulfide, or tellurium; zinc sulfide, indium-antimony, lead selenide, gallium arsenide, and silica or ormosil), which have been coated with zinc sulfide to improve the properties of the fluorescent agents.

In particular, fluorescent probe species are a preferred type of imaging probe. A fluorescent probe species is a fluorescent probe that is targeted to a biomarker, molecular structure or biomolecule, such as a cell-surface receptor or antigen, an enzyme within a cell, or a specific nucleic acid, e.g., DNA, to which the probe hybridizes. Biomolecules that can be targeted by fluorescent imaging probes include, for example, antibodies, proteins, glycoproteins, cell receptors, neurotransmitters, integrins, growth factors, cytokines, lymphokines, lectins, selectins, toxins, carbohydrates, internalizing receptors, enzyme, proteases, viruses, microorganisms, and bacteria.

In certain embodiments, probe species have excitation and emission wavelengths in the red and near infrared spectrum, e.g., in the range 550-1300 or 400-1300 nm or from about 440 to about 1100 nm, from about 550 to about 800 nm, or from about 600 to about 900 nm. Use of this portion of the electromagnetic spectrum maximizes tissue penetration and minimizes absorption by physiologically abundant absorbers such as hemoglobin (<650 nm) and water (>1200 nm). Probe species with excitation and emission wavelengths in other spectrums, such as the visible and ultraviolet light spectrum, can also be employed in the methods of the embodiments of the present invention. In particular, fluorophores such as certain carbocyanine or polymethine fluorescent fluorochromes or dyes can be used to construct optical imaging agents, e.g. U.S. Pat. No. 6,747,159 to Caputo et al. (2004); U.S. Pat. No. 6,448,008 to Caputo et al. (2002); U.S. Pat. No. 6,136,612 to Della Ciana et al. (2000); U.S. Pat. No. 4,981,977 to Southwick, et al. (1991); U.S. Pat. No. 5,268,486 to Waggoner et al. (1993); U.S. Pat. No. 5,569,587 to Waggoner (1996); U.S. Pat. No. 5,569,766 to Waggoner et al. (1996); U.S. Pat. No. 5,486,616 to Waggoner et al. (1996); U.S. Pat. No. 5,627,027 to Waggoner (1997); U.S. Pat. No. 5,808,044 to Brush, et al. (1998); U.S. Pat. No. 5,877,310 to Reddington, et al. (1999); U.S. Pat. No. 6,002,003 to Shen, et al. (1999); U.S. Pat. No. 6,004,536 to Leung et al. (1999); U.S. Pat. No. 6,008,373 to Waggoner, et al. (1999); U.S. Pat. No. 6,043,025 to Minden, et al. (2000); U.S. Pat. No. 6,127,134 to Minden, et al. (2000); U.S. Pat. No. 6,130,094 to Waggoner, et al. (2000); U.S. Pat. No. 6,133,445 to Waggoner, et al. (2000); U.S. Pat. No. 7,445,767 to Licha, et al. (2008); U.S. Pat. No. 6,534,041 to Licha et al. (2003); U.S. Pat. No. 7,547,721 to Miwa et al. (2009); U.S. Pat. No. 7,488,468 to Miwa et al. (2009); U.S. Pat. No. 7,473,415 to Kawakami et al. (2003); also WO 96/17628, EP 0 796 111 B1, EP 1 181 940 B1, EP 0 988 060 B1, WO 98/47538, WO 00/16810, EP 1 113 822 B1, WO 01/43781, EP 1 237 583 A1, WO 03/074091, EP 1 480 683 B1, WO 06/072580, EP 1 833 513 A1, EP 1 679 082 A1, WO 97/40104, WO 99/51702, WO 01/21624, and EP 1 065 250 A1; and Tetrahedron Letters 41, 9185-88 (2000).

Exemplary fluorochromes for probe species include, for example, the following: Cy5.5, Cy5, Cy7.5 and Cy7 (GE® Healthcare); AlexaFluor660, AlexaFluor680, AlexaFluor790, and AlexaFluor750 (Invitrogen); VivoTag™680, VivoTag™-S680, VivoTag™-S750 (VISEN Medical); Dy677, Dy682, Dy752 and Dy780 (Dyomics®); DyLight® 547, and/or DyLight® 647 (Pierce); HiLyte Fluor™ 647, HiLyte Fluor™ 680, and HiLyte Fluor™ 750 (AnaSpec®); IRDye® 800CW, 1RDye® 800RS, and IRDye® 700DX (Li-Cor®); ADS780WS, ADS830WS, and ADS832WS (American Dye Source); XenoLight CF™ 680, XenoLight CF™ 750, XenoLight CF™ 770, and XenoLight DiR (Caliper® Life Sciences); and Kodak® X-SIGHT® 650, Kodak® X-SIGHT 691, Kodak® X-SIGHT 751 (Carestream® Health).

Suitable means for imaging, detecting, recording or measuring the present nanoparticles may also include, for example, a flow cytometer, a laser scanning cytometer, a fluorescence micro-plate reader, a fluorescence microscope, a confocal microscope, a bright-field microscope, a high content scanning system, and like devices. More than one imaging techniques may be used at the same time or consecutively to detect the present nanoparticles. In one embodiment, optical imaging is used as a sensitive, high-throughput screening tool to acquire multiple time points in the same subject, permitting semi-quantitative evaluations of tumor marker levels. This offsets the relatively decreased temporal resolution obtained with PET, although PET is needed to achieve adequate depth penetration for acquiring volumetric data, and to detect, quantitate, and monitor changes in receptor and/or other cellular marker levels as a means of assessing disease progression or improvement, as well as stratifying patients to suitable treatment protocols.

The systems and methods described herein can be used with other imaging approaches such as the use of devices including but not limited to various scopes (microscopes, endoscopes), catheters and optical imaging equipment, for example computer based hardware for tomographic presentations. The successful surgical management of prostate cancer (PC) depends upon the accuracy with which disease can be detected perioperatively. Improvements in overall survival and long-term morbidity rely on the ability of the surgeon to obtain negative surgical margins and completely resect regionally metastatic lymph nodes (LNs). Intraoperative imaging guidance, however, is principally based on human visual cues and tactile information without the ability to identify molecular determinants on the cancer itself. One approach, intraoperative fluorescence imaging, has emerged as a highly reliable tool to improve visualization, and can be seamlessly integrated into the surgical workflow.

As described in the Examples, the modular C' dot platform containing core-containing and surface-bearing silica nanoparticle functionalities were improved. Encapsulation of spectrally-distinct NIR reactive dyes (e.g., Cy5.5, e.g., CW800) into the core of C' dots differentiate between surface-bound targeting moieties.

Peptides optimized for targeting prostate-specific membrane antigen (PSMA) and gastrin-releasing peptide receptor (GRPr), or other prostate cancer targets can be used. For example, PSMA-targeting C' dots and GRPr-targeting C' dots can incorporate dyes and surface radiometals. Biological properties of PSMA- and GRPr-targeting peptides and particles functionalized with PSMA inhibitor (PSMAi) and GRP ligands were screened in conventional cell lines, metastatic subclones of PC lines, and patient-derived human prostate organoid cultures expressing PSMA or GRPr transcripts by RNA-seq. Lead candidates were then assessed in xenograft and/or orthotopically-injected PC models by PET-optical imaging methods. An investigational drug (IND) study can be conducted for the lead PSMA-targeting product for use in an early stage image-guided surgical trial designed to detect PSMA-expressing metastatic nodes and/or positive tumor margins. In parallel, spectrally-distinct particle probes and multiplexing strategies can accurately detect PSMA- and GRPr-expressing metastatic nodes for next-stage clinical trial designs and are examined.

The present disclosure provides for determining and optimizing tunable surface chemistries for NIR dye-encapsulating PSMA- and GRPr-targeted C' dots to achieve favorable binding kinetics/uptake in prostate cancer (PC) cell lines. Moreover, the present disclosure provides for synthesizing and characterizing prototype fluorescent PSMAi-PEG- and GRP-PEG-C' dots. Moreover, the present disclosure provides for improving photophysical properties to enhance detection sensitivity and tissue contrast. Moreover, the present disclosure provides for assessing particle probes in PSMA and GRPr-expressing conventional (e.g., LNCaP, PC3) prostate cancer cell lines for binding affinity, internalization, specificity, and cytotoxicity. Moreover, the present disclosure provides for variations in PSMA and/or GRPr target expression levels in human prostate organoid cultures and metastatic subclones of PC lines (LAPC4, VCaP) to select lead candidates for in vivo studies.

The present disclosure also provides for assessing tumor-selective accumulation and PK profiles of optimized hybrid C' dots in PSMA- and GRPr-expressing models to identify probes with favorable targeting kinetic and clearance profiles. For example, in certain embodiments, the present disclosure provides for optimizing surface radiolabeling conditions for PSMAi- and GRP-conjugated-C' dots with $^{64}$Cu, $^{67}$Ga, or $^{89}$Zr. Moreover, in certain embodiments, the present disclosure provides for performing screening PK and imaging studies with lead PSMAi and GRP-conjugated dots in orthotopic and xenograft models derived from conventional/metastatic cell lines and human prostate organoid models maximally expressing one/both targets, to identify probes with favorable targeting/clearance kinetics. Moreover, in certain embodiments, the present disclosure provides for developing spectrally distinct NIR dye-containing products from lead C' dot candidates to permit accurate and sensitive detection of multiple markers expressed on nodal and/or distant metastases in preclinical models using MRI-PET imaging and fluorescence-based multiplexing strategies with correlative histology.

The present disclosure also provides for performing IND-enabling studies for the clinical trial of PSMAi-C' dots, determining an efficacious dose range (microdose) and exposure (PK and clearance/dosimetry) for the lead candidate product in mice to inform IND enabling nonclinical safety studies, conducting single-dose acute toxicology evaluation as a microdosing study using a single rodent model, and conducting a pilot clinical trial to evaluate safety and radiation dosimetry of a lead PSMA-targeting C' dot, as well as obtain pilot data on the detection of PC, residual tumor along surgical margins, and locoregional lymph nodes using intraoperative optical and preoperative PET/MR imaging.

In certain embodiments, PET-NIR optical imaging probe capabilities can be used to enable higher-resolution concurrent visualization of multiple molecular targets on tumor cell surfaces in PC. For example, two NIR particles (e.g., C' dots) can be adapted with two different PC-targeting ligands. Radiometals can also be attached to enable pre-operative PET imaging for screening metastases. These developments, in aggregate, should ultimately improve surgical staging and management of PC patients. Surgeons are able to more precisely assess the exact location of PC and metastatic disease, facilitating more complete resections of cancerous foci, reducing the likelihood of tumor recurrence, and improving locoregional control and oncologic outcomes.

Cross-sectional imaging options are scarce for perioperative detection of metastatic nodes and/or residual disease along surgical margins. Although a large number of radiolabeled peptido-based agents have been advanced for pre-/clinical imaging studies, which show specific targeted uptake at sites of disease, limitations have included (i) paucity of available NIR optically-active surgical probes for visualization of cancerous foci; (ii) high non-specific probe accumulations in radiosensitive organs/tissues with associated adverse therapeutic consequences; (iii) inability to assay different PC markers controlling distinct biological events; and (iv) loss of bioactivity resulting from direct attachment of hydrophobic $N_1R$ dyes to PSMAi-based agents. Overcoming such limitations requires innovation at every level of product development, including the synthesis of newer-generation C' dots in water-based environments to achieve better surface chemical control, dye encapsulation to prevent loss of bioactivity; utilization of one-pot synthesis methods for efficient surface functionalization, and the tailoring of linker and peptide designs facilitating particle attachment. As FDA-IND clearance has been received for two integrin-targeting, NIR dye-encapsulating silica particle products—one for mapping metastatic nodes in melanoma and the other for mapping particle distributions in malignant brain tumors, additional IND-enabling technologies—Cy5.5-dye incorporated PSMAi-PEG-C' dots and CW800 dye-incorporated GRP-PEG-C' dots, for improved image-guided localization of cancerous nodes and residual disease in PC were generated. Moreover, the combined use of these products for real-time tumor phenotyping in PC models, in conjunction with a high sensitivity handheld multispectral fluorescence camera system (Quest Spectrum™, Quest Medical Imaging, Netherlands) tuned to simultaneously detect spectrally-distinct optical signals with emissions around 700 nm Cy5.5) and 800 nm (CW800), helps to improve understanding of biological processes targeted by these particle probes. This portable camera system, adapted for both open and laparoscopic imaging applications, overcomes limitations associated with existing "black box" small animal imaging technologies, while achieving much higher spatial and wavelength resolutions.

Intermediates

The present invention also includes intermediates useful in the synthesis of provided conjugates. Accordingly, in some embodiments the present invention provides a compound of formula:

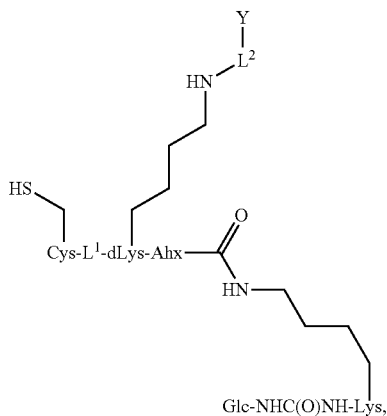

wherein each of $L^1$, $L^2$, and Y is as defined above and described in classes and subclasses herein, both singly and in combination.

In some embodiments, the present invention provides a compound of formula:

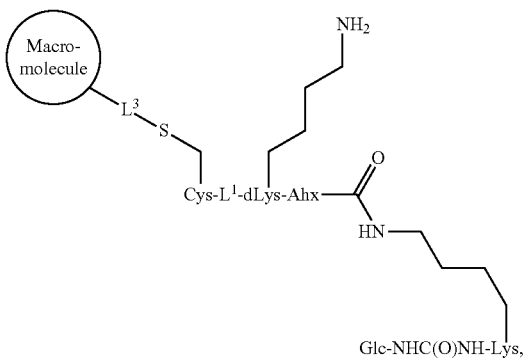

wherein each of $L^1$, $L^3$, and a macromolecule is as defined above and described in classes and subclasses herein, both singly and in combination. In some embodiments, the present invention provides a compound of formula:

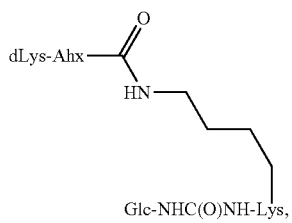

wherein one or more amino acid side chain groups or termini are optionally protected with a suitable protecting group, and wherein one amino acid is optionally attached to a resin.

In some embodiments, the present invention provides a compound of formula:

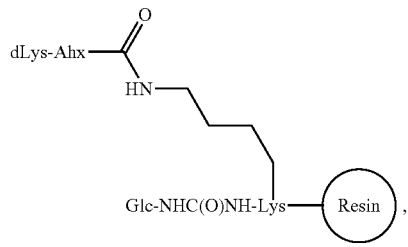

wherein one or more amino acid side chain groups or termini are optionally protected with a suitable protecting group.

In some embodiments, the present invention provides a compound:

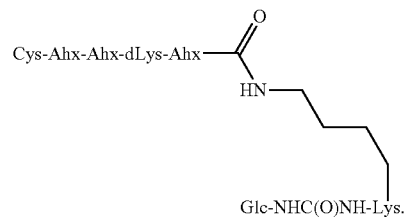

wherein one or more amino acid side chain groups or termini are optionally protected with a suitable protecting group, and wherein one amino acid is optionally attached to a resin.

In some embodiments, the present invention provides a compound of formula:

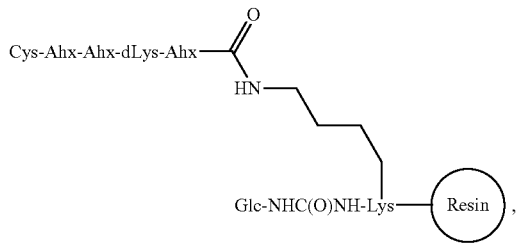

wherein one or more amino acid side chain groups or termini are optionally protected with a suitable protecting group.

In certain embodiments, the present invention provides a compound selected from:

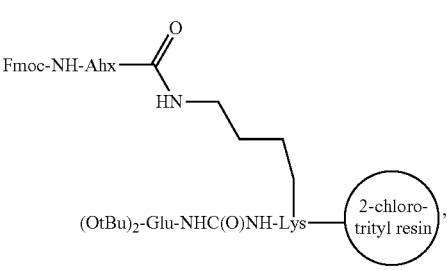

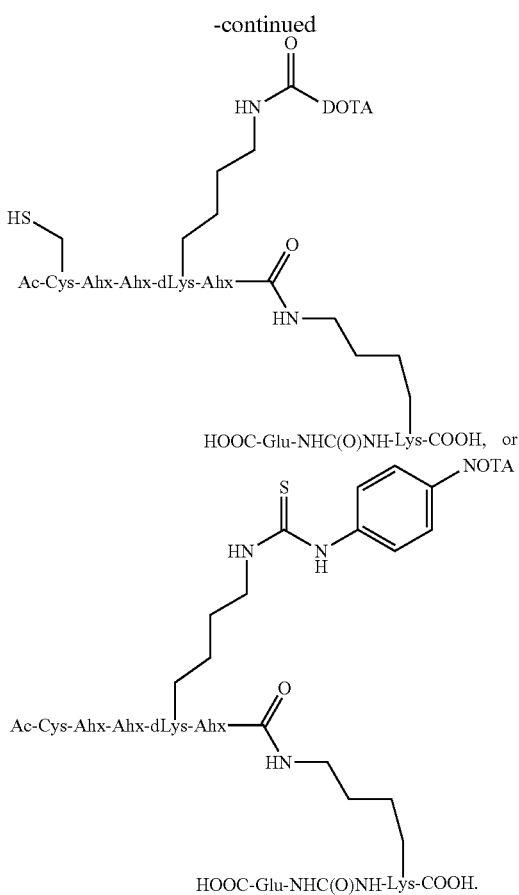

EXAMPLES

Figure 3:
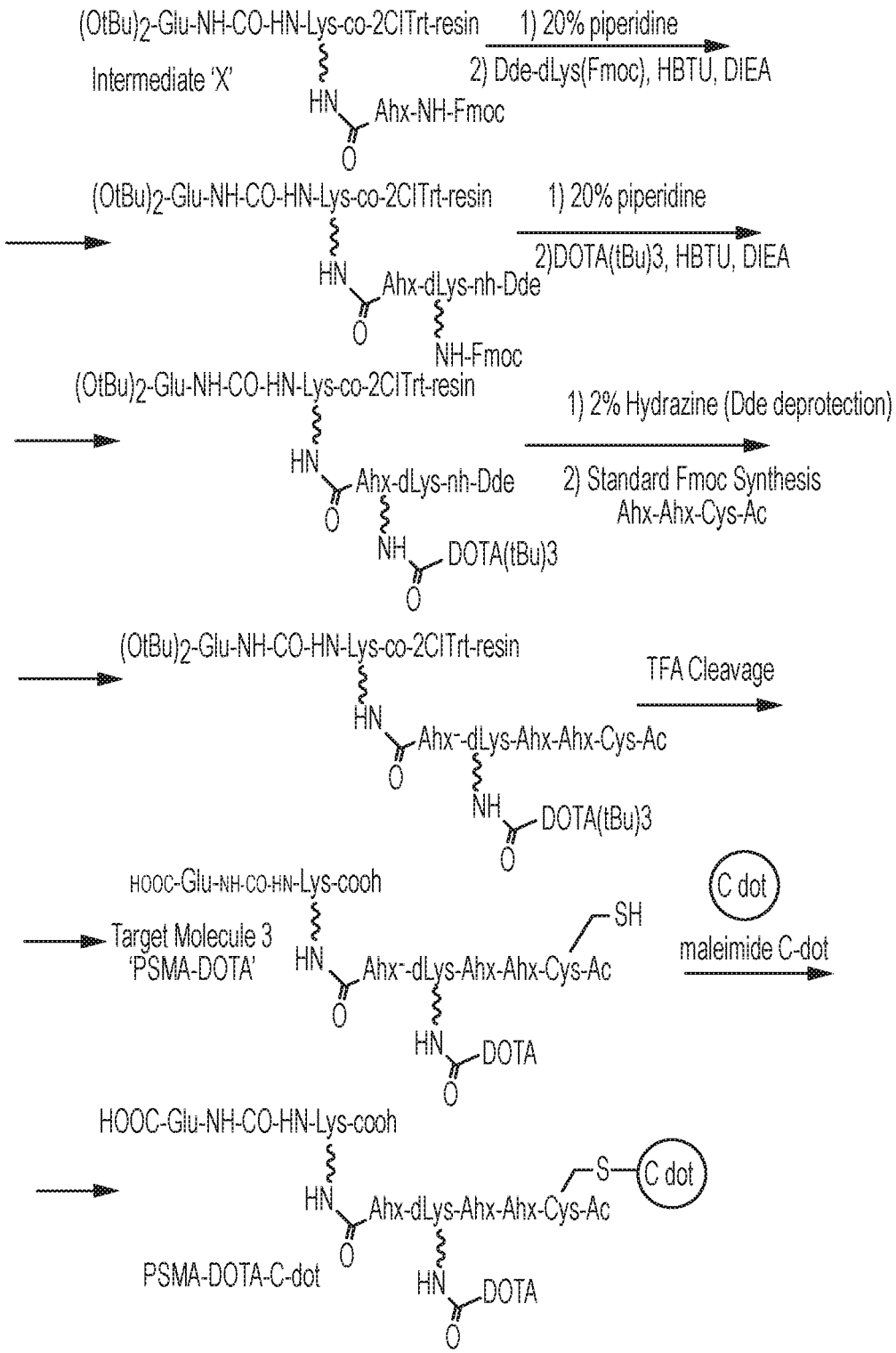
FIG. 3 is a schematic of the synthesis of PSMAi conjugate attached to a nanoparticle with a DOTA, starting with PSMAi Intermediate "X" (FIG. 2), to generate PSMAi-DOTA-C'dot, according to an illustrative embodiment of the invention. Note that this strategy can be expanded to include any protected chelator monomer, such as protected NOTA (tBu)2, NODA-GA(tBu)3, DTPA(tBu)4.
Figure 4:
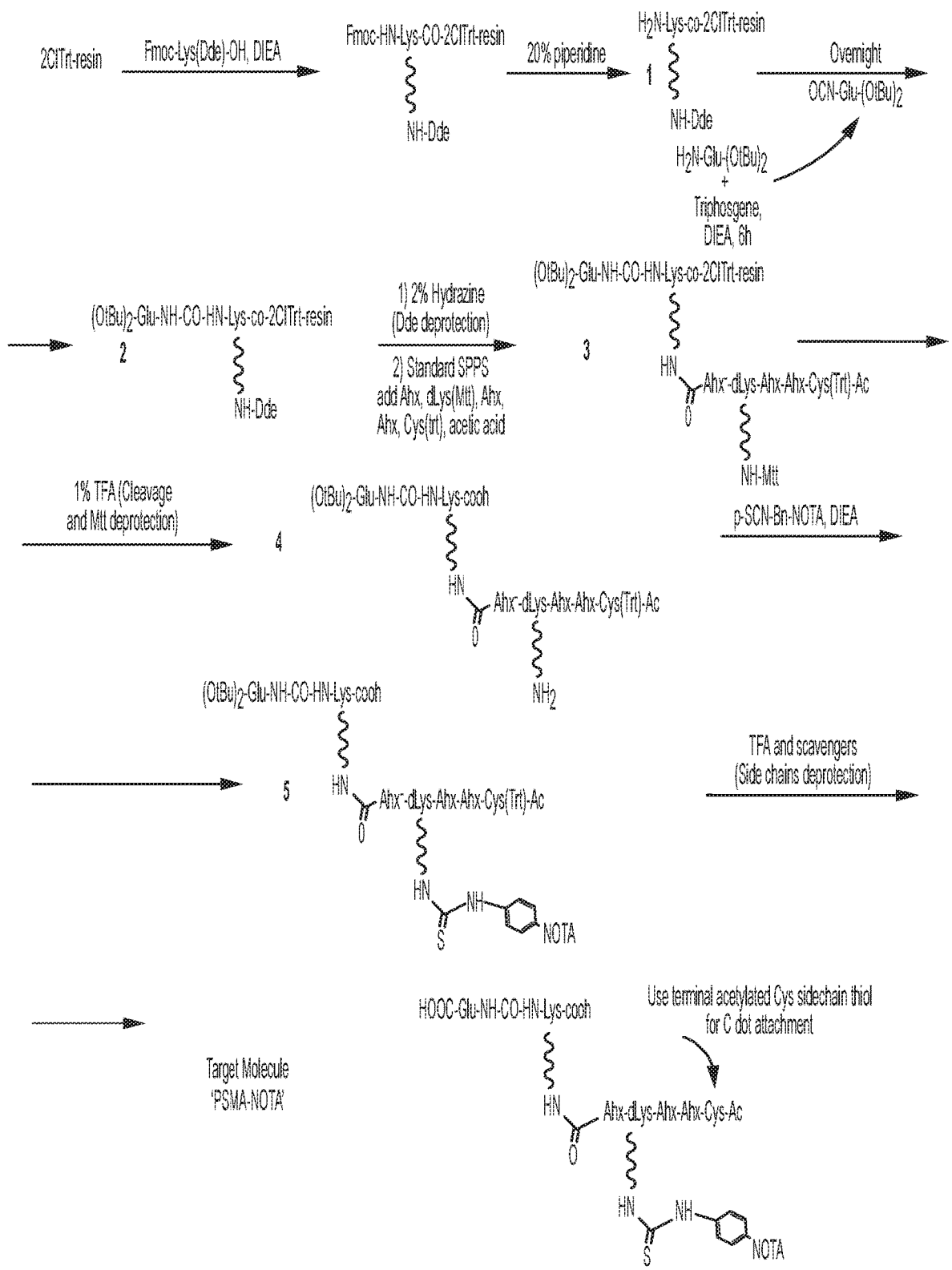
FIG. 4 is a schematic of synthesis of SCN-Bn-PSMAi-Bn-NOTA, according to an illustrative embodiment of the invention. Note that this strategy can be expanded to include any non-protected chelator.

The present Examples provides for the development of conjugates where constructs containing a PSMA inhibitor ("PSMAi") and metal chelator are covalently attached to a macromolecule. Various macromolecules and chelators can be used. In preferred embodiments, the macromolecules include ultrasmall silica-based nanoparticles (e.g., nanoparticles having a diameter no greater than 20 nm, e.g., C-dot, e.g., C'-dot). In certain embodiments, the metal chelator includes HBED-CC. In other certain embodiments, the metal chelator includes NOTA. In other preferred embodiments, the metal chelator includes DOTA. In certain embodiments, the disclosed chelators can be protected and can be added to the described conjugates as shown in FIG. 3. In certain embodiments, the disclosed chelators can be un-protected and can be added to the described conjugates as shown in FIG. 4.

The compositions that result from these conjugation chemistries generate branched structure targeting molecules and macromolecule structures (e.g., nanoparticle structures (e.g., C-dot structures)) that provide properties not exhibited by PSMAi targeting molecules that are free and unbound. For example, a macromolecule (e.g., a nanoparticle) serves as a scaffold for the PSMAi-chelator constructs. In certain embodiments, multiple PSMAi-chelator constructs can be attached to the surface of a macromolecule (e.g., an ultrasmall nanoparticle, e.g., a C-dot), thereby enabling multivalent or polyvalent interactions between the particle and the PSMA positive tissue. In certain embodiments, from 2 to 30 PSMAi-chelator constructs can be attached to the surface of the macromolecule. In certain embodiments, from 2 to 25 PSMAi-chelator constructs can be attached to the surface of the macromolecule. In certain embodiments, from 2 to 20 PSMAi-chelator constructs can be attached to the surface of the macromolecule. In certain embodiments, from 5 to 10 PSMAi-chelator constructs can be attached to the surface of the macromolecule.

Delivery and consequent binding of the PSMAi-chelator-nanoparticle composition to a target tissue can be enhanced exponentially as compared to delivery and binding of multiple individual free PSMAi-HBED-CC/chelator molecules to the target tissue. For example, PSMAi-chelator constructs may be more effectively delivered to and bound with target tissue by administration of constructs in the form of a PSMAi-chelator-nanoparticle composition rather than administration of free PSMAi-chelator.

Example 1

Figure 1B:
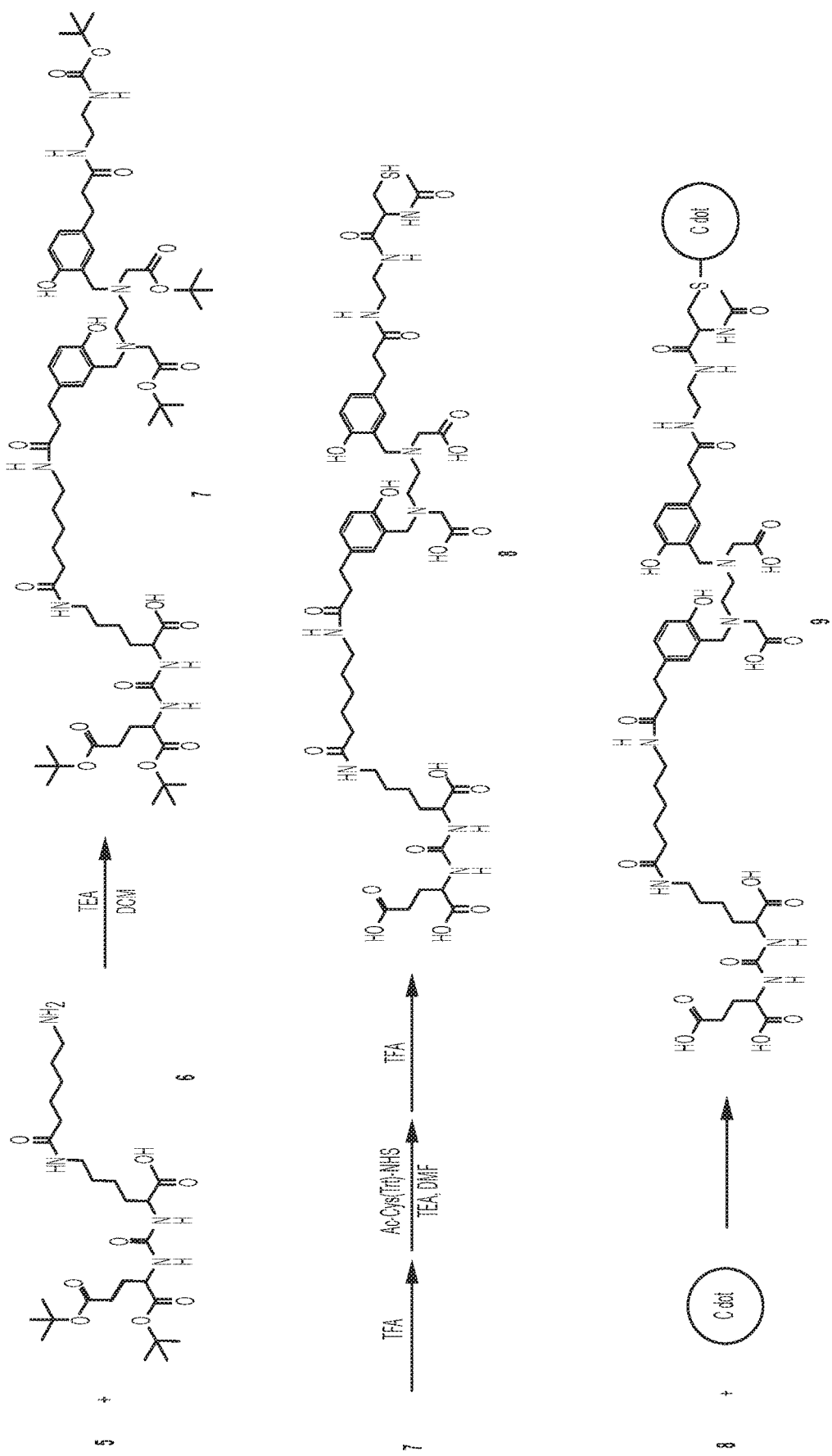

Synthetic Protocol for Target Molecule PSMAi-HBED-CC as Shown in FIG. 1

FIG. 1 shows a schematic of a synthetic route used to obtain a modified form of PSMAi-HBED-CC, which was successfully conjugated onto a nanoparticle. A synthesis protocol is provided below.

Reagents

Solvents and reagents purchased from commercial sources were used without further purification. HBED-CC-di(tBu)ester (1) was purchased from ABX. Acetonitrile, diethyl ether, dimethylformamide (DMF), ethyl acetate, hexanes, hexafluoroisopropanol (HFIP), methanol, methylene chloride (DCM), and trifluoroacetic acid (TFA) were obtained from Fisher. Dimethylsulfoxide (DMSO), diisopropylethylamine (DIEA), 1-Ethyl-3-(3-dimethylaminopropyl)carbodiimide (EDC), N-hydroxysuccinimide (NHS) and triethylamine (TEA) were purchased from Sigma-Aldrich. 2-(7-Aza-1H-benzotriazole-1-yl)-1,1,3,3-tetramethyluronium hexafluorophosphate (HATU) was purchased from Genescript.

Flash Chromatography

Normal phase (silica gel) purifications were conducted on a Teledyne ISCO CombiFlash Rf using 4 g, 12 g, 24 g, and 40 g cartridges using hexanes, ethyl acetate, methylene chloride and/or methanol.

Analytical HPLC

Samples were run on a Waters Alliance HPLC System or Autopure LCMS System (2767 Sample Manager, 2996 Photodiode Array Detector, 2420 ELS Detector, Micromass ZQ, 2525 Binary Gradient Module, Column Fluidics Organizer, 515 HPLC Pump, Pump Control Module II) using a linear gradient of 5-95% acetonitrile in water (0.5% TFA) for 10 minutes at 1.2 mL/min, on either a C4 or C18 4.6×50 mm reversed phase XBridge analytical column (Waters). Samples were analyzed at either 348 nm or 650 nm.

Preparative HPLC

Samples were purified on either a Waters Preparative System (2996 Photodiode Array Detector, 2545 Binary Gradient Module) or Autopure LCMS System using a linear gradient of 5-95% acetonitrile in water (0.5% TFA) for 30 minutes at 20 mL/min on a C18 19×150 mm reversed phase XBridge preparative column (Waters). Samples were analyzed at either 220 nm or 348 nm.

Synthesis Protocol for Target Molecule PSMAi-HBED-CC

HBED-CC-di(tBu)ester (1) was dissolved in DCM and TEA (3 eq) in a rbf and allowed to stir. Chlorotrityl chloride (2) was added (1.2 eq) and monitored by TLC and LCMS.

After 3 hrs, the solution was concentrated in vacuo and then purification by flash chromatography. The off-white solid 3 was isolated then dissolved in DMF and DIEA (4 eq). tert-Butyloxycarbonyl-diaminoethane was added (1.5 eq) followed by HATU (2 eq). The reaction was completed in 30 min (as determined by LCMS), and then concentrated in vacuo. 4 was isolated as an oil and resuspended in DCM then purified by flash chromatography. The white solid was dissolved in a solution of 50% HFIP in DCM and incubated for 2 hrs. The solution was concentrated in vacuo, and then washed with diethyl ether. The deprotected product was confirmed by LCMS. The residue was resuspended in DCM, cooled in an ice bath. EDC was added (5 eq), stirred for 30 min, and then NHS (3 eq) was added. The reaction was monitored by TLC. After 4 hours, the reaction was concentrated in vacuo, and then purified by flash chromatography. The white solid 5 was isolated, dissolved in DCM and TEA (5 eq), to which 6 was added and the reaction was allowed to proceed overnight. The solvent was removed in vacuo, and the resulting oil was resuspended in ACN and purified by reversed phase HPLC (RP-HPLC), where the lyophilized resulting in a white solid 7 (confirmed by LCMS). TFA (5% water) was added to the solid and stirred for 30 min. The solution was concentrated in vacuo, then washed with cold ether, dissolved in water/ACN (1:1), and lyophilized. DMF and TEA (5 eq) was added to the white solid, stirred, then the activated cysteine ester (Ac-Cys(Trt)-NHS, 3 eq) was added. After 4 hrs, the reaction was concentrated in vacuo, and then purified by RP-HPLC and lyophilized. The white solid was treated with a solution of TFA:TIS:water (ratio 90:0.5:0.5) for 2 hrs, evaporated, and purified by RP-HPLC. After lyophilization, white solid 8 was incorporated into the nanoparticle as previously described.

Synthesis for Protected Chelator-PSMAi Conjugates as Shown in FIG. 3

Figure 2:
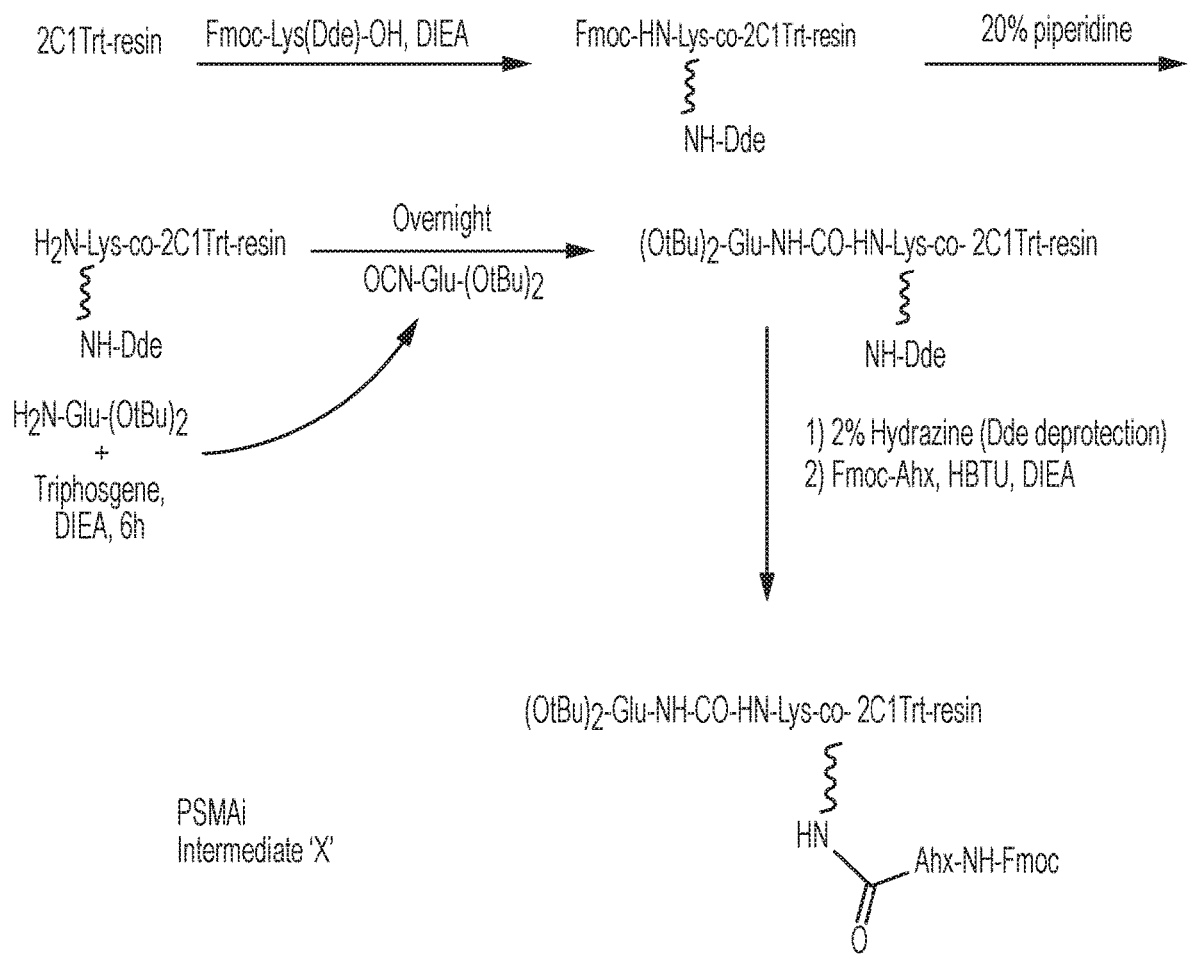
FIG. 2 is a schematic of generation of an intermediate composition "PSMAi Intermediate 'X'" that is subsequently used for attachment of metal chelator (e.g., DOTA, e.g., HBED, e.g., wherein the chelator is any protected chelator) and nanoparticle, according to an illustrative embodiment of the invention.

FIG. 3 is a schematic of the synthesis of PSMAi conjugate attached to a nanoparticle with a DOTA, starting with Intermediate "X" (FIG. 2), to generate PSMAi-DOTA-C'dot, according to an illustrative embodiment of the invention. FIG. 2 shows a schematic of generation of an intermediate composition "PSMAi Intermediate 'X'" that is subsequently used for attachment of a metal chelator (e.g., DOTA, e.g., HBED, e.g., NOTA) and a macromolecule (e.g., nanoparticle).

The strategy in FIG. 3 (PSMAi-DOTA) is used for the addition of chelators that are protected. For example, NCS-DFO can be added the same way as NCS-NOTA. As another example, this strategy can be expanded to include any protected chelator monomer, such as protected NOTA(tBu)2, NODA-GA(tBu)3, DTPA9tBu)4.

In certain embodiments, a chelator typically has to be added at the last or penultimate step of synthesis.

Synthetic Protocol for Target Molecule SCN-Bn-PSMAi-Bn- NOTA as Shown in FIG. 4

FIG. 4 is a schematic of synthesis of SCN-Bn-PSMAi-Bn- NOTA, according to an illustrative embodiment of the invention. Synthesis of PSMAi-NOTA-C-dot is described below. The synthesis scheme shown in FIG. 4 is used to attach NCS-DFO to the PSMAi construct.

A difference between the PSMAi-DOTA constructs and PSMAi-NOTA constructs is that a DOTA is attached while the peptide construct is still attached to the resin. This is possible since a fully protected DOTA can be purchased and activated using SPPS methods. In contrast, for PSMAi-NOTA synthesis the SCN-Bn-NOTA is added after the peptide construct is cleaved from the resin. In certain preferred embodiments, a NOTA derivative is used that causes the linker to come off of the backbone of the chelator. In certain embodiments, p-SCN-Bn-NOTA is used to construct the PSMAi-NOTA construct. The NOTA chelator can be easily and stably radiolabeled with Ga and Cu radioisotopes. In certain embodiments, NOTA has a better labeling efficiency and stability using $^{64}$Cu than DOTA. Note that SCN-Bn-NOTA can only be purchased as an unprotected chelator.

However, there are a number of protected NOTA chelators available for purchase. If a protected NOTA(tBu)2 is used, it can be added in a similar matter that protected DOTA (tBu)3 was added to the constructs. In general, any protected chelator addition would likely use the strategy in FIG. 3 and any non-protected chelator would us the strategy in FIG. 4.

Figure 5:
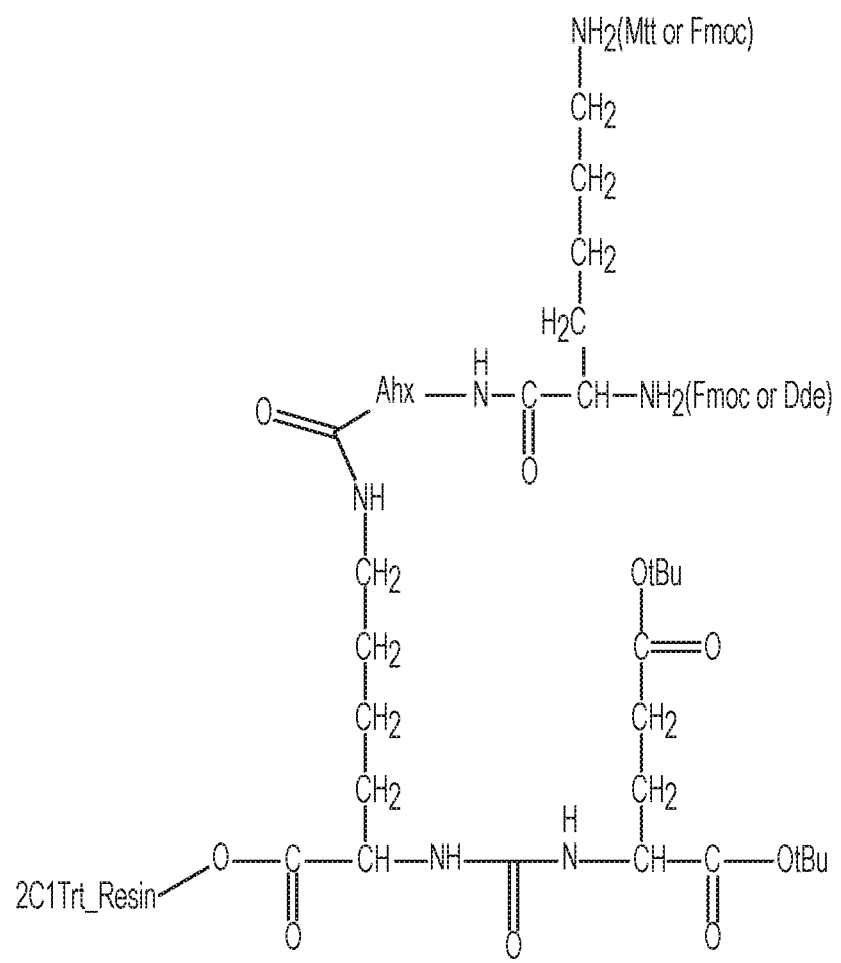
FIG. 5 shows a molecule for pendent NOTA or DOTA constructs, according to an illustrative embodiment of the invention.

A linker with a pendent NOTA was attached for conjugation to the particle. For this to work with the C dots, for example, a linker sequence with a terminal Cys was used to join the Lys-urea-linkage-Glu pharmacophore to the particle. FIG. 5 shows a molecule for generating the pendent NOTA or DOTA constructs. Depending on which orthogonal protection scheme was used it would allow the ability to put any number of linkers, with a terminal acetylated Cys, to connect to the C dot, including the (Ahx)2-Cys-Ac or a PEG-Cys-Ac or a linker composed of natural or non-natural amino acids-Cys-Ac. It also allows any number of chelators or fluorescent dyes to be attached to the side chain of the D-Lys.

Abbreviations

Ac-: acetyl; Ahx: 6-AminoHexanoic Acid; Dde: 1-(4,4-dimethyl-2,6-dioxacyclohexylidene)ethyl; DIEA: N,N-diisopropylethylamine; EDT: 1,2-Ethanedithiol; Fmoc: 9-fluorenylmethyloxycarbonyl; HBTU: 2-(1H-benzotriazole-1-yl)-1,1,3,3-tetranethyluronium hexafluorophosphate; HOBt: 1-hydroxybenzotriazole; HPLC: high pressure liquid chromatography; —NCO: Isocyanate; LC-ESI-MS: liquid chromatography-Electro Spray Ionization-mass spectrometry; Mtt: 4-Methyltrityl; p-SCN: para-isothiocyanate; Sta: statine (4-amino-3-hydroxy-6-methylheptanoic acid); tBu: tert-butyl; SPPS: Solid Phase Peptide; TA: Thioanisole Synthesis; TFA: trifluoroacetic acid; Trt: Trityl; TIS: Triisopropylsilane.

Materials

All reagents were HPLC grade or peptide synthesis grade. TFA, HBTU, HOBt were obtained from Oakwood Product INC, Estill, S.C.; All the Fmoc-Amino-acid derivatives and 2ClTrt resin were obtained from Chem-Impex International, SC Wood Dale, Ill. All solvents (Piperidine, DIEA, Phenol, and TIS) were purchased by Aldrich, St Louis, Mo. p-SCN-NOTA was purchased from Macrocyclics, Plano, Tex.

Synthetic Protocol for Target Molecule PSMAi-NOTA

The orthogonally protected building block Fmoc-Lys (Dde)-OH was first loaded on 2-ClTrt resin in a manual reaction vessel (Chemglass, Vineland, N.J.) and the Fmoc protection group removed to give compound 1.

At the same time the Glutamic isocyanate building block [OCN-Glu-(OtBu)$_2$] was prepared by reacting the di-tBu protected Glutamic acid with triphosgene and DIEA for 6 h at 0° C.

Overnight reaction at room temperature between the isocyanate building block [OCN-Glu-(OtBu)2] and the free α amino group of compound 1 yielded the fully protected Urea 2 on the resin.

The Dde protection group on Lys 2 was removed by 2% hydrazine, and compound 3 was obtained by building the peptide sequence Ac-Cys-Ahx-Ahx-dLys-Ahx- on the r-amino group of the Lys of compound 2 using an AAPPTEC 396 omega multiple peptide synthesizer (AAPPTEC, Louisville, Ky.) employing standard Fmoc chemistry and standard SPPS. The permanent protection groups chosen for the amino acid side chains were: Trt for Cys and Mtt for Lys. Trt and Mtt protection groups were selected based on an orthogonal protection scheme. The Mtt protecting group was selected to protect Lys so that the Mtt could be removed without removing other protecting groups. For example, the Trt on Cys will not come off in 1% TFA but the Mtt on Lys can be removed in 1% TFA. In certain embodiments, other orthogonal protection schemes can be used. The Fmoc protecting groups were removed at every subsequent cycle by treatments with 20% Piperidine for 10 min. The peptide chain was assembled by sequential acylation (20 min for coupling) with "in situ" activated Fmoc-amino acids. Recoupling was automatically performed at every cycle.

The "in situ" activations of Fmoc-amino acids (3 eq. compared to the resin amount) were carried out using uronium salts (HBTU, 2.7 eq., HOBT 3 eq.) and DIEA (6 eq.).

Mtt protecting group on the dLys was removed and in the same reaction compound 3 was cleaved from the resin in the otherwise protected form by treatment with 1% TFA. The obtained compound 4 was reacted overnight in DMF with p-SCN-Bn-NOTA in presence of DIEA to obtain the NOTA labeled compound 5.

Side chain protecting groups were finally removed from compound 5 by treating it with TFA, in the presence of the following scavengers, at a 2.5% concentration each: Phenol, water, TIS, TA and EDT.

The target molecule (TM), PSMAi-NOTA, was characterized by LC-MS and finally purified by MS aided semi-preparative HPLC, using in house optimized gradients.

Analysis and Purification

HPLC analysis and semi-preparative purification were performed on a Beckmann Coulter System Gold HPLC equipped with a 168 diode array detector, a 507e auto-injector and the 32 KARAT software package (Beckmann Coulter, Fullerton, Calif.).

The analytical column used for HPLC was purchased from Thermo Fisher, Waltham, Mass. (BetaBasic C18, 150 Å, 0.46 cm×15 cm, 5 µm). For preparative HPLC, the column used was purchased from Waters, Milford, Mass. (Prep NovaPak, HR-C18, 7.8×300 mm, 6 µM, 60 Å).

Flow rate was maintained at 1 mL/min for analytical runs and at 10 ml/min for semi-preparative purification.

The wavelengths used to monitor this gradient were 214/280 nm in the analytical and 225/235 for the semi-preparative run.

Mobile phase eluents used in all runs were water (A), and acetonitrile (B) each containing 0.1% TFA. The gradient used to analyze the crude preparation was: linear from 10% to 50% B in 30 min. For preparative purification a minimal part of the flow (0.5 mL/min) can be diverted to the MS ion trap, so exploiting the possibility of seeing in real time the m/z profile of whatever was eluting.

This 'MS aided Preparative HPLC technique' greatly facilitated the purification of otherwise very complex mixture. The gradient used in preparative purification was: linear from 15% to 35% B in 40 min. ESI-MS: All LC-MS analyses and MS assisted Preparative purifications were performed with an LCQ Fleet from Thermo Fisher, Waltham, Mass.

Figure 6A:
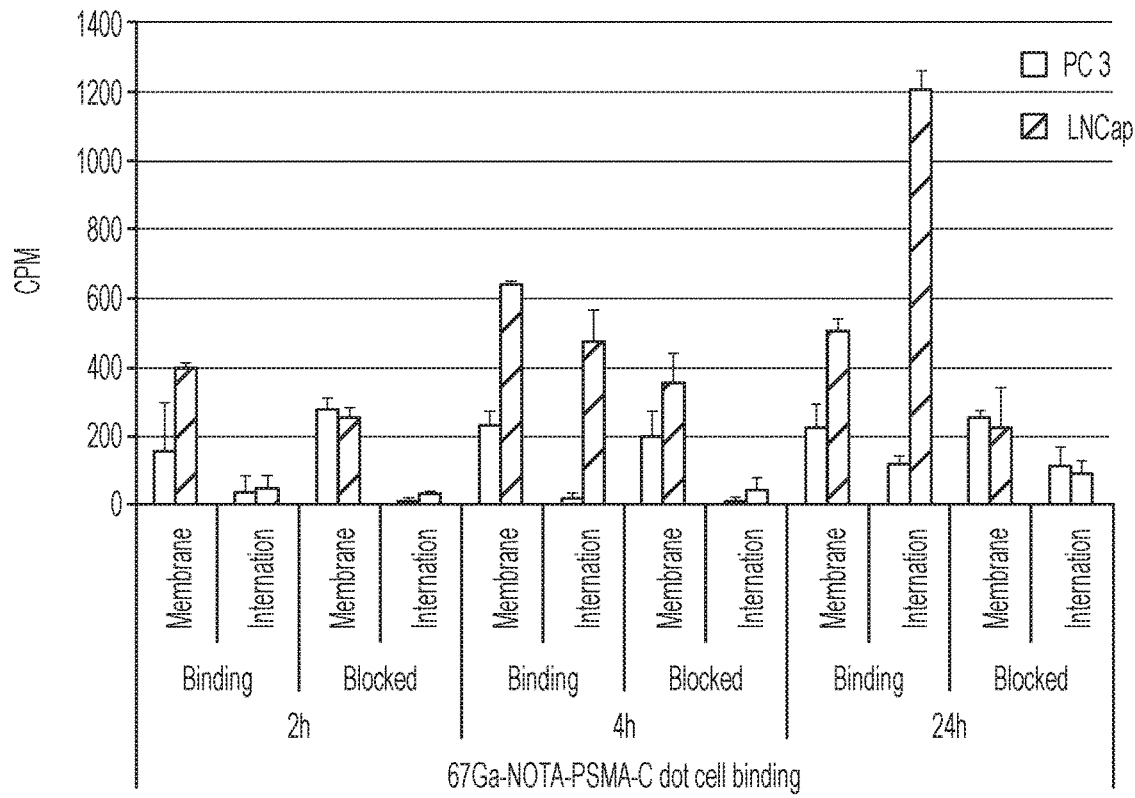
FIGS. 6A and 6B shows in vitro cell binding data at three time points for $^{67}$Ga-NOTA-PSMAi-C'dot (FIG. 6A) and $^{64}$Cu-NOTA-PSMAi-C'dot (FIG. 6B). Each PSMAi/chelator construct attached to a nanoparticle exhibited good uptake and internalization in LNCaP cell, which are high in PSMA expression, and lower uptake in PC3 cells, which are low in PSMA expression. Blocking studies using 2-(phosphonomethyl)pentanedioic acid (PMPA) show specific uptake. The data also shows that there is a steady increase in uptake of the radiolabeled PSMAi-C'dots with time.
Figure 6B:
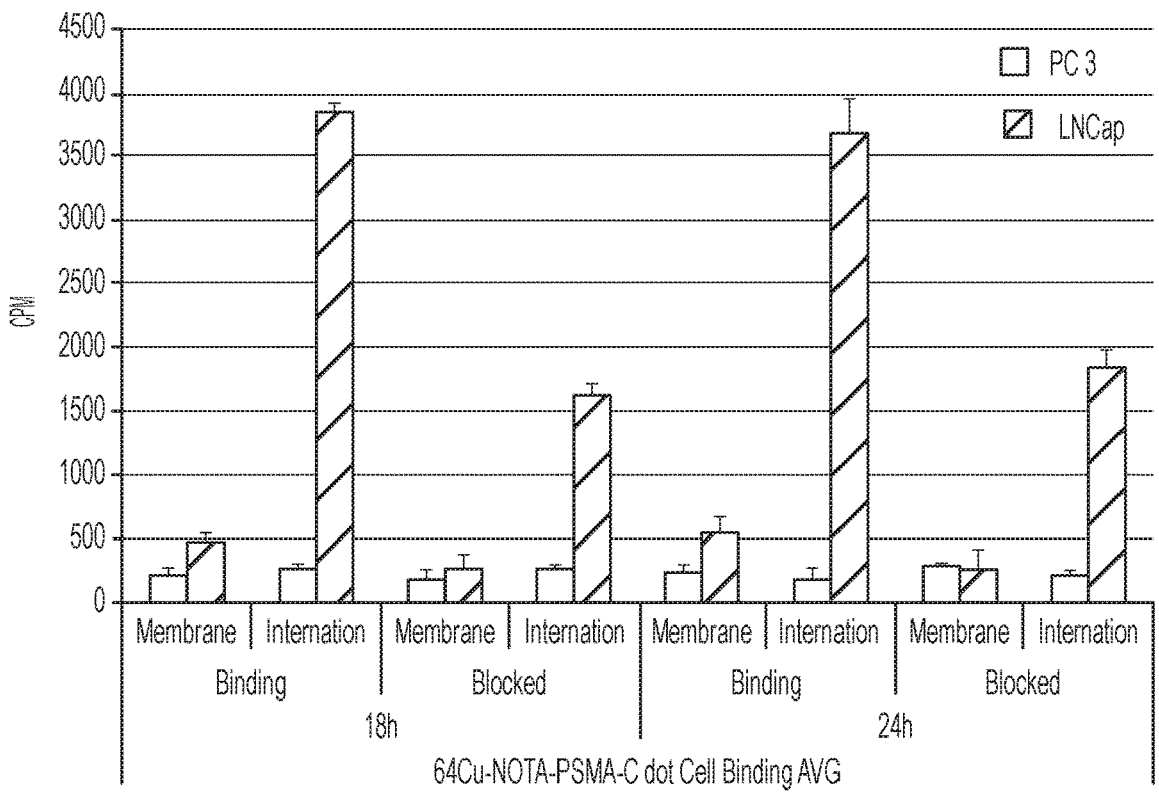

Dramatically Less Kidney Uptake Using PSMAi-Chelator Conjugates Attached to a Macromolecule Compared to Radiolabeled PSMAi Ligand Alone FIGS. 6A and 6B shows in vitro cell binding data at three time points for $^{67}$Ga-NOTA-PSMAi-C'dot (FIG. 6A) and $^{64}$Cu-NOTA-PSMAi-C'dot (FIG. 6B). Each PSMAi/chelator construct attached to a nanoparticle exhibited good uptake and internalization in LNCaP cell, which are high in PSMA expression, and lower uptake in PC3 cells, which are low in PSMA expression. Blocking studies show specific uptake. The data also shows that there is a steady increase in uptake of the radiolabeled PSMAi-C'dots with time.

Surprisingly, there appears to be a difference in uptake based on the choice of radionuclide. For example, the uptake of the 67Ga-labelled composition compared to the uptake of the 64Cu composition exhibited differences in uptake. Without wishing to be bound to any theory, this unexpected variance may be due to variable blocking.

Figure 7A:
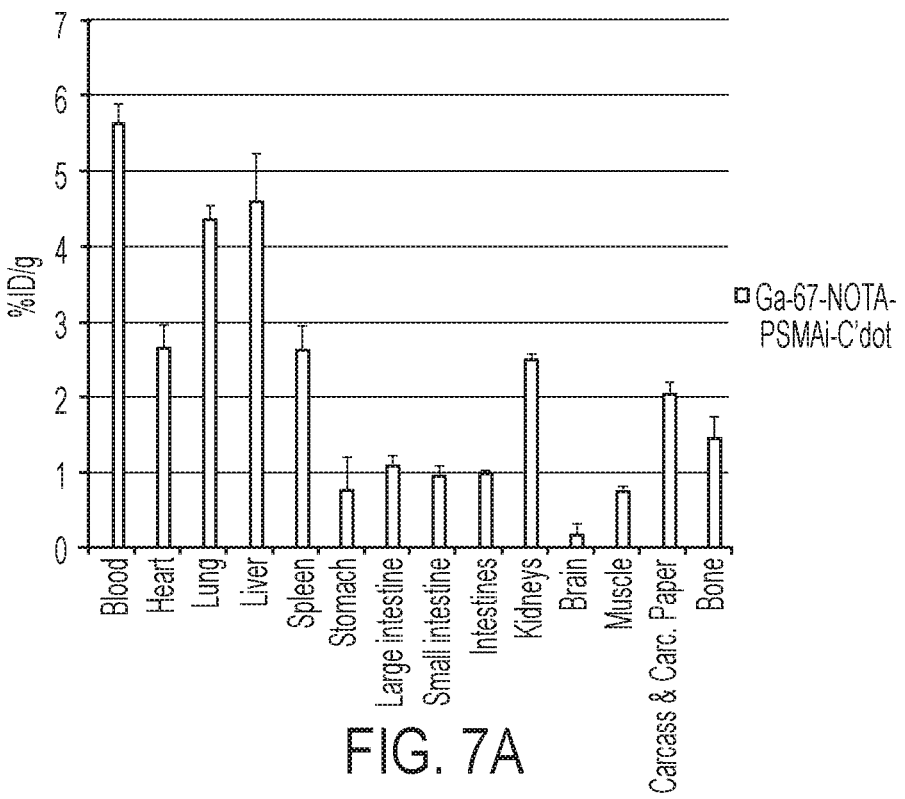
FIG. 7A shows $^{67}$Ga-NOTA-PSMAi-C'dot biodistribution in nude mice (FIG. 7A) and in LNCaP tumor bearing mice (FIG. 7B) at 24 h post injection. Surprisingly, the $^{67}$Ga-NOTA-PSMAi-C'dot exhibited low kidney uptake.
Figure 7B:
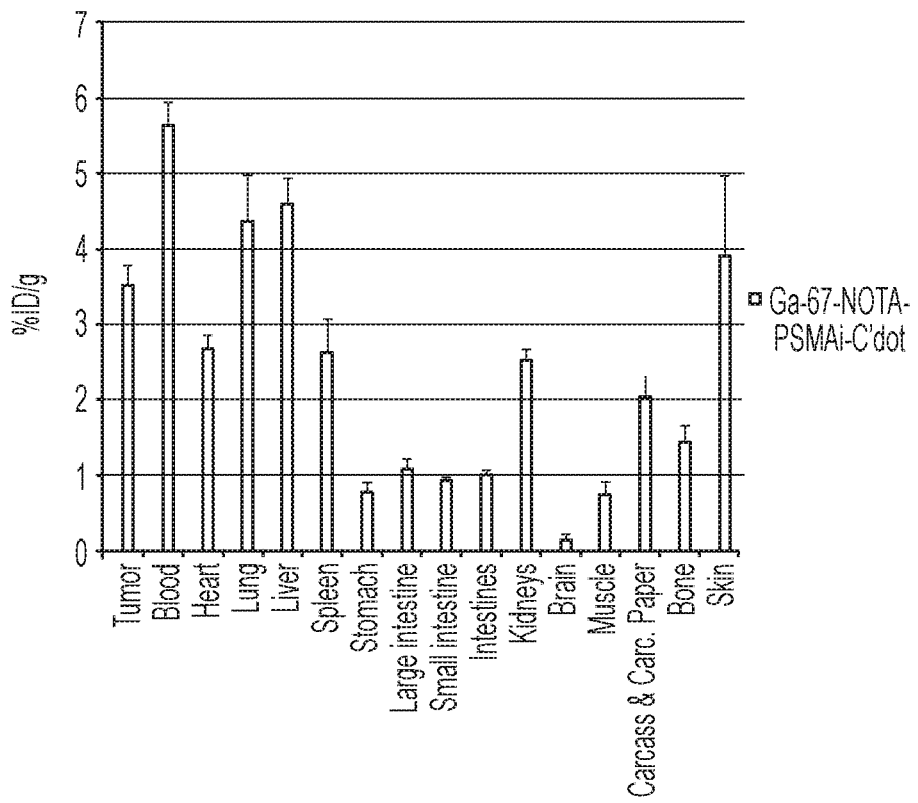

FIG. 7A shows $^{67}$Ga-NOTA-PSMAi-C'dot biodistribution in nude mice (FIG. 7A) and in LNCaP tumor bearing mice (FIG. 7B) at 24 h post injection. Surprisingly, the $^{67}$Ga-NOTA-PSMAi-C'dot exhibited low kidney uptake.

Low kidney uptake of $^{67}$Ga-NOTA-PSMAi-C'dot was unexpected as other PSMAi/chelator constructs have demonstrated high uptake in the kidney (see Weineisen et al., *J Nucl Med* 2015; 56:1169-1179) (see Banerjee et al., *J. Med. Chem.* 2010, 53, 5333-5341). Therefore, attaching PSMAi/chelator constructs to macromolecules (e.g., nanoparticles (e.g., C'dots)) provide at least this benefit compared to free PSMAi/chelator constructs.

Figure 8A:
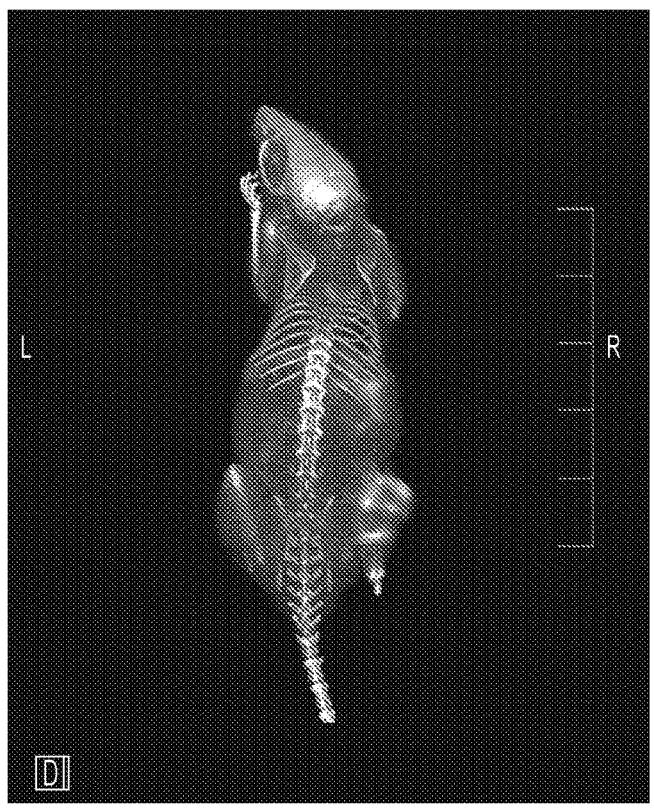
FIGS. 8A and 8B show $^{67}$Ga-NOTA-PSMAi-C dot SPECT imaging LNCaP tumors 24 h post injection.
Figure 8B:
Figure 9A:
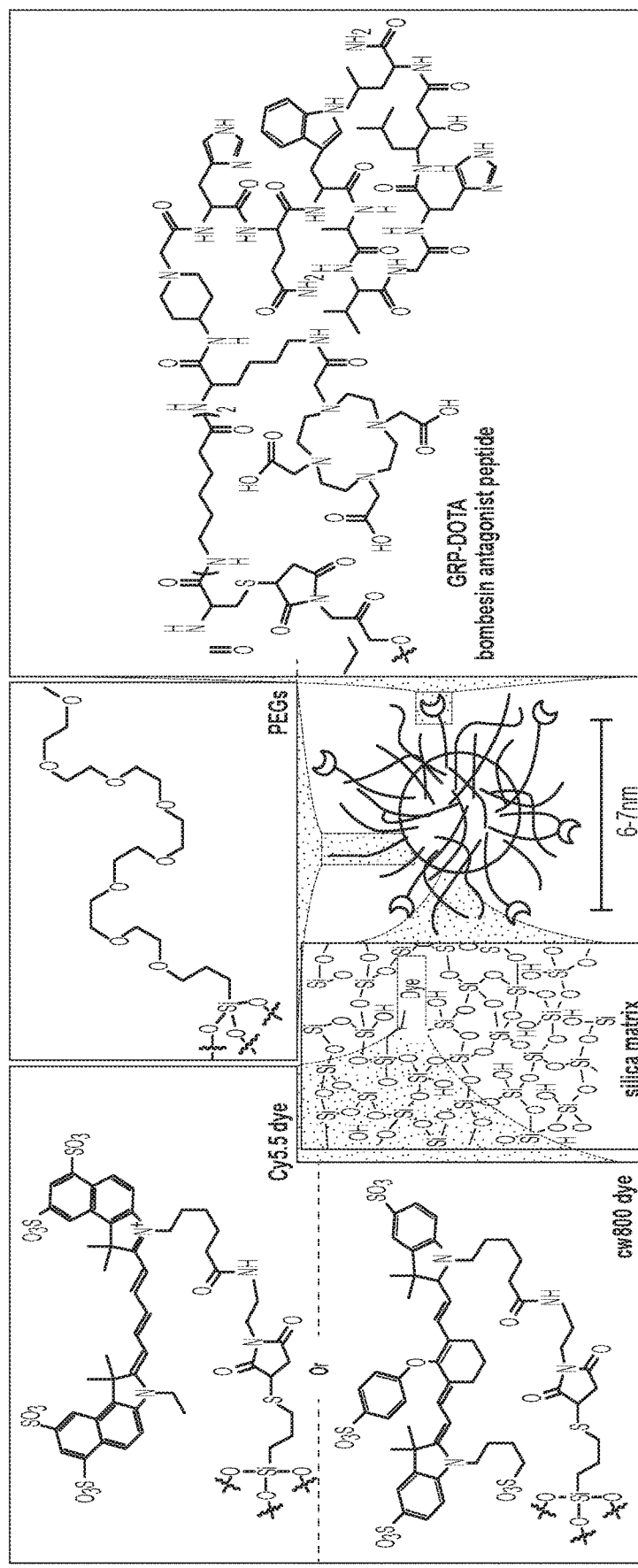
FIGS. 9A-9D show preliminary data of C' dot synthesis.
Figure 9B:
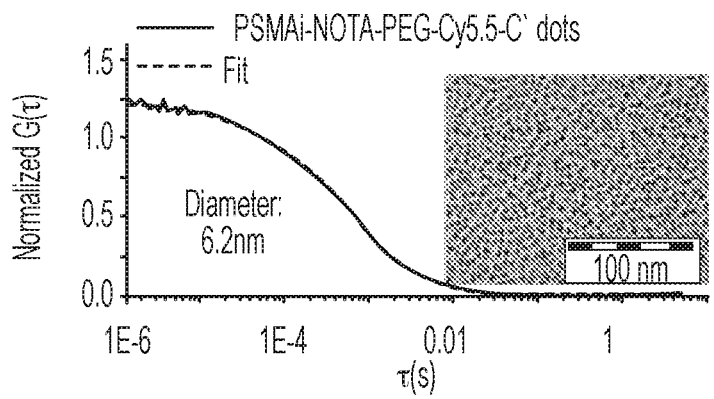
Figure 9C:
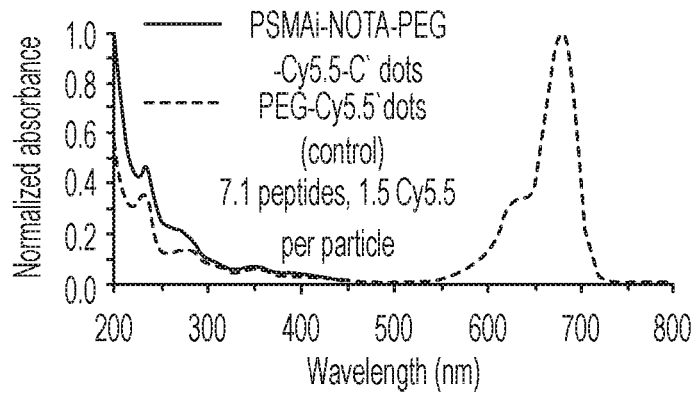
Figure 9D:
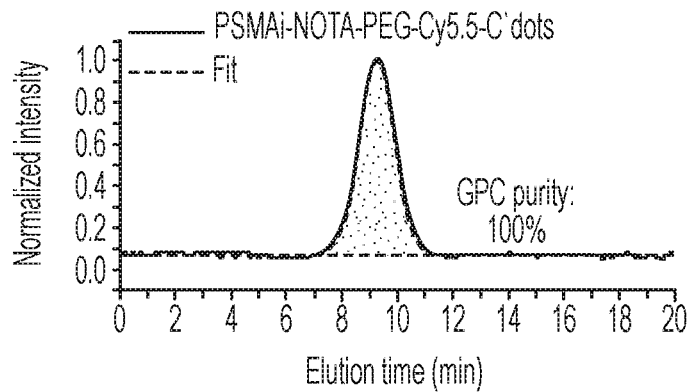

FIGS. 8A and 8B show $^{67}$Ga-NOTA-PSMAi-C dot SPECT imaging LNCaP tumors 24 h post injection. FIGS. 8A and 8B show administration of 0.5 mCi $^{67}$Ga-NOTA-PSMAi-C dot (FIG. 8A) or co-injection of 0.5 mCi $^{67}$Ga-NOTA-PSMAi-C and 2-(phosphonomethyl)pentanedioic acid (PMPA) (160 µg/20 g) (FIG. 8B) in a mouse model. PMPA is a black that shows a reduction in uptake of $^{67}$Ga-NOTA-PSMAi-C dot, demonstrating specificity and confirming the results presenting in the in vitro data presented in FIG. 6A.

Constructive Example 2

Determine and Optimize Tunable Surface Chemistries for NIR Dye-Encapsulating PSMA- and GRPr-Targeted C' Dots to Achieve Favorable Binding Kinetics/Uptake in Prostate Cancer (PC) Cell Lines Prostate Targeting C' Dot Peptides Analogs of the Glu-urea-Lys PSMAi inhibitor and bombesin/gastrin releasing peptide (GRP) antagonist were designed to contain functionality for radiolabeling and for attachment to ultrasmall (sub-10 nm) fluorescent core-shell silica nanoparticles (FIG. 3, FIGS. 9A-9D). Peptides were synthesized using standard solid phase peptide synthesis. PSMAi was synthesized by reacting a glutamic isocyanate building block with 2-ClTrt resin loaded with $NH_2$-Lys (Dde)-OH to yield the fully protected Glu-urea-Lys resin. The peptide sequence Ac-Cys(Trt)-Ahx-Ahx-dLys(Mtt)-Ahx was added to the Lys ε-amino group of resin-bound Glu-urea-Lys after the removal of the Dde protection. Finally, the Mtt group was removed from the dLys ε-amino group and reacted with pSCN-Bn-NOTA. Side chain protecting groups were removed by TFA treatment.

A GRP antagonist (Ac-Cys-Ahx-Ahx-Lys(DOTA)-4-amino-1-carboxy-methyl-piperidine-His-Gln-Trp-Ala-Val-Gly-His-Sta-Leu-$NH_2$) (SEQ ID NO: 2) was synthesized by solid phase peptide synthesis (SPPS), based on the RM2 sequence. The Lys-DOTA was attached via a positively-charged 4-amino-1-carboxymethyl-piperidine linker.

The deprotected PSMAi and GRP peptides were characterized by LC-MS and purified by MS aided semi-preparative HPLC. Purified peptides were conjugated via their N-terminal Cys-thiols to maleimide-PEG-silane. PSMAi- NOTA and GRP-DOTA PEG-silane conjugates were added with mono-functional PEG-silane into the particle synthesis solution for surface attachment to C' dots. Conjugated C' dots were separated from free peptide by size exclusion chromatography. The number of peptides attached per particle was estimated by the reaction concentration ratio of peptide ligand-PEG-silane to particles, and confirmed using the peptide absorbance spectrum. Particle reconstitution was confirmed by fluorescence correlation spectroscopy (FCS) analyses.

A PSMA-HBED-CC-amido ethyl thiol analog was synthesized and incorporated onto C' dots. Starting with di-tert-butyl protected HBED-CC (ABX Chemicals), one free carboxylic acid was protected with a trityl group. The remaining free carboxylic acid was coupled to PSMAi, as above. The trityl group was removed, and the carboxylic acid modified with an S-trityl amino ethyl thiol. Global deprotection was achieved under acidic conditions to yield the desired PSMAi-HBED-CC-amido ethyl thiol. The compound was then conjugated to C' dots using thiol-maleimide chemistry.

Competitive Cell Binding ($IC_{50}$)

Figure 10:
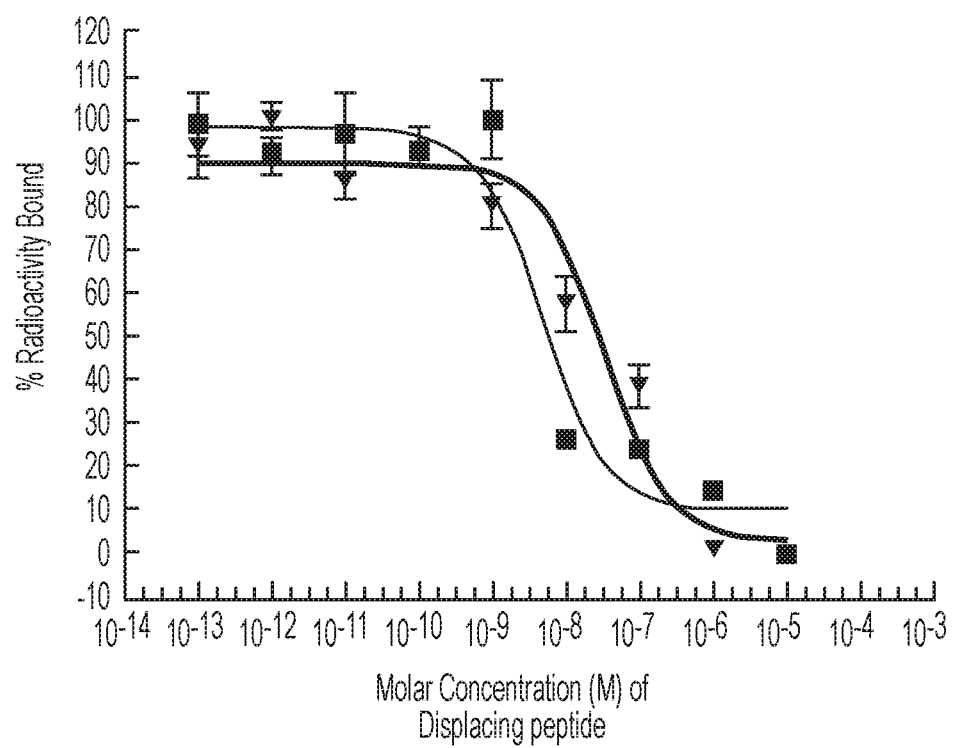
FIG. 10 shows peptide IC50 determination: competitive binding curves of PSMAi-NOTA-(●) and GRP-DOTA peptides (⑤) with their $^{67}$Ga radiolabeled counterparts in LNCaP and PC3 cells, respectively.

PSMAi-NOTA-C'dot and GRP-DOTA-C' dot peptides using the corresponding $^{67}$Ga labeled peptides were examined in competitive prostate cancer cell binding studies with LNCaP and PC3 prostate cancer cells, respectively (FIG. 10). Apparent $K_d$ values for PSMAi-NOTA-C' dot and GRP-DOTA-C' dot peptides were $4.92 \times 10^{-9}$ and $3.38 \times 10^{-8}$, respectively.

Methods

Table 5 shows a variety of peptide constructs for improved affinity and particle linkage according to embodiments of the present disclosure. For example, PSMA-targeting and GRPr-targeting peptide sequences can be chemically adapted to preserve pharmacophore activity when conjugated to maleimide-functionalized PEG chains, and then to C' dots synthesized in water-based environments. The number of peptide ligands per particle can be estimated by absorption spectroscopy. C' dot core size can be adjusted to optimize numbers of reactive NIR dyes to maximize particle brightness. Table 5 shows examples of approximately 8 C' dots constructs with various linker chemistries and a number of PSMAi and GRP ligands per particle can be tuned to maximize biological properties. Competitive binding studies can be used to select optimal particle probes for PK analysis.

TABLE 5

Peptide constructs for improved affinity and particle linkage

| | |
|---|---|
| PEG-NOTA-Ahx-PSMAi | Ac-Cys-(PEG)$_5$-dLys(NOTA)-Ahx-Lys-urea-Glu |
| Ahx$_2$-NOTA-Nal-Tea-PSMAi | Ac-Cys-(Ahx)$_2$-dLys(NOTA)-Nal-Tea-Lys-urea-Glu |
| PEG-NOTA-Nal-Tea-PSMAi | Ac-Cys-(PEG)$_5$-dLys(NOTA)-Nal-Tea-Lys-urea-Glu |
| PEG-dLys(DOTA)-RM2-GRP | Ac-Cys-(PEG)$_5$-dLys(DOTA)-Acp-RM2-GRP |
| PEG-dLys(DOTA)-GRP | Ac-Cys-(PEG)$_5$-dLys(DOTA)-Acp-His-GRP |

Ahx: Amino hexanoic acid;
PEG: polyethylene glycol;
Tea: transexamic acid;
Acp: 4-amino-1-carboxymehtyl-piperidine;
Nal: 2-Naphthylalalanine Develop and Characterize Prototype Fluorescent PSMAi-Conjugated C' Dots and GRP-Conjugated-C' Dots.

The present disclosure provides for design and characterization strategies that can be used to inform attachment of PSMAi and GRP ligands, radiolabels, and the corresponding prototype C' dot targeting platforms. Moreover, the present disclosure provides for synthetic approaches in water-based environments that can be used to enable better surface chemical control of C' dots and radiochemical stability.

Structurally Optimize PSMA-Targeting and GRPr-Targeting Peptides.

Figure 21:
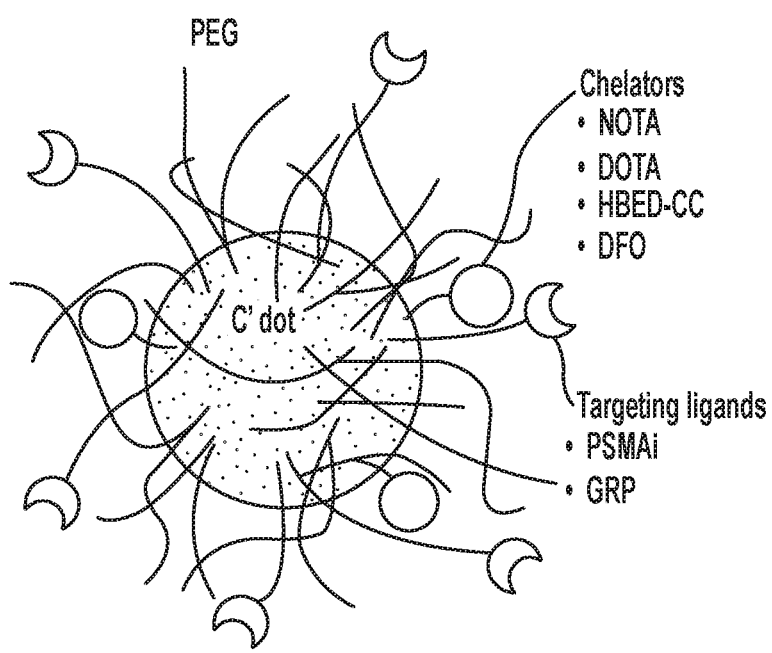
FIG. 21 shows PSMAi NOTA and DFO chelated to C'dots. The PSMA targeting moiety, Glu-urea-Lys, and radiometal chelator are separately attached to C' dots.

The present disclosure also provides for structurally optimizing PSMA-targeting peptides and GRPr- targeting peptides to enhance PC uptake while decreasing non-target tissue uptake. For example, Axh linker moieties between the Glu-urea-Lys pharmacophore and the radiometal chelator and linker, which are used to conjugate peptides to the particle (FIGS. 9A-9D), can be substituted with PEG to add hydrophilicity (Table 5). It is noted that changes in the nature and charge of the chelator conjugated to the PSMA-targeting peptide, as well as the linker, dramatically affect tumor uptake, but also has a more profound result in the clearance properties. For example, improving tumor-to-normal tissue ratios, especially for the kidney and salivary glands, is important for radiotherapeutic applications. Alternatively, direct conjugation of the chelator to the particle surface can be examined to improve receptor binding and uptake of these platforms (FIG. 21).

SPPS chemistry can be employed to synthesize the PSMAi, bombesin GRP, and associated peptide-chelator constructs using an Advanced ChemTech Tetras or AAPPTEC 396 peptide synthesizer. Preparative LC-MS HPLC can be used to identify and purify target compounds using a Beckman Coulter system coupled to a LCQ-Fleet Ion trap mass spectrometer (MS). Purified peptides can be conjugated to maleimide-terminated PEG-silane via N-terminal Cys-thiol prior to particle surface functionalization. Alternatively, free surface amine-containing particles can be conjugated directly with NHS or SCN chelators by post-PEGylation surface modification by insertion (PPSMI, vide infra).

Synthesize and Characterize PSMAi-NOTA-C' Dots, PSMAi-HBED-CC-C' Dots, PSMAi-DFO-C' Dots and GRP-DOTA-C' Dots Bearing Varying Ligand Numbers.

In accordance with certain embodiments, ultrasmall (e.g., sub-10 nm) fluorescent core-shell silica nanoparticles can be functionalized with the following chelated peptides: PSMAi-NOTA, PSMAi-HBED-CC, PSMAi-deferoxamine (DFO), and GRP-DOTA. Such peptides can be synthesized from single-batch reactions in aqueous media, for example.

Figure 14:
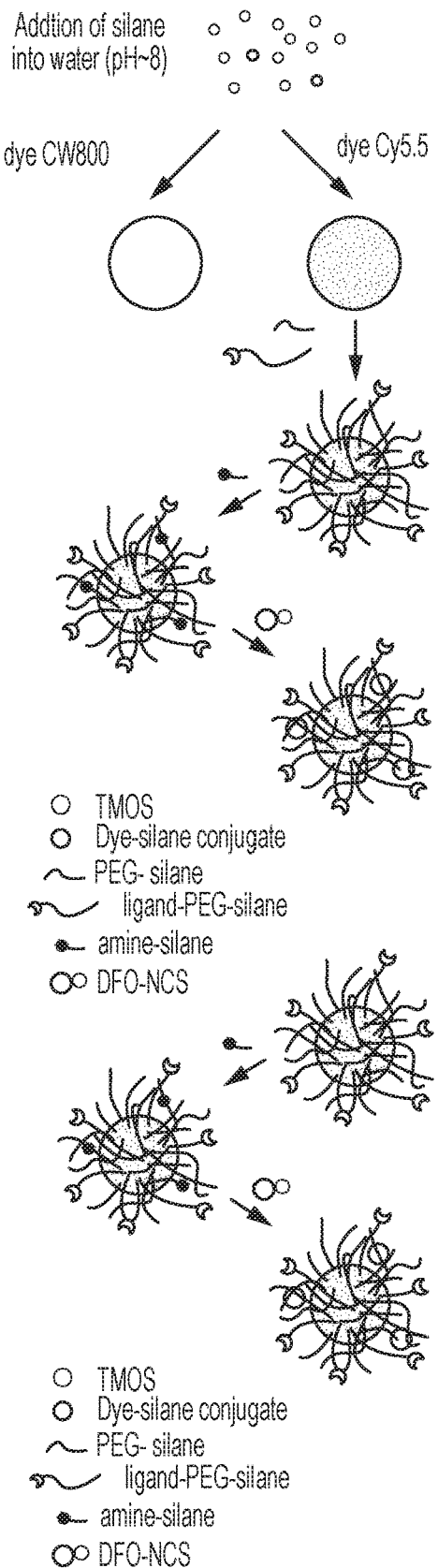
FIG. 14 shows schematic highlighting steps in the C'dot synthesis.

FIG. 14 shows a simplified flow chart of the synthesis steps. In short, together with dye-silane conjugates prepared separately, water-soluble silica precursors (TMOS; tetramethoxy orthosilicate) can be added to water at slightly basic pH-8 to accelerate silane hydrolysis and particle formation. After a well-defined time period, particle growth can be terminated by simultaneous addition of peptide ligand-bearing PEG-silane and PEG-silane. After synthesis, particles can be submitted to a set of purification and characterization steps. For example, purification steps can include gel permeation chromatography (GPC) to separate particles from aggregation products and free dye. Moreover, characterization steps can include FCS to assess hydrodynamic size, concentration, and brightness relative to free dye in water, fluorescence and optical spectroscopy to determine the number of dyes and ligands per particle, zeta-potential measurements to assess particle surface charge, as well as dynamic light scattering (DLS) for comparing size results with FCS.

For the synthesis of PSMAi-DFO for $^{89}$Zr radiolabeling, a method was developed—post-PEGylation surface modification by insertion (PPSMI). After the PEGylation step with plain PEG-silane, as well as PSMAi bearing PEG-silane, small amounts of functional silanes (e.g., Amine-silane) were first introduced to the PEGylated surface, and were subsequently reacted with DFO-NCS thereby inserting the DFO molecules in between the PEG chains (see FIG. 14). DFO molecules were efficiently radiolabeled, resulting in high targeting efficiencies (above 10% ID/g) and tumor to background ratios seen on initial biodistribution studies with PSMA-targeting C' dots (FIG. 13) or integrin-targeting C' dots. After synthesis, particle purification and characterization can be performed as described herein.

Improve Photophysical Properties to Enhance Detection Sensitivity and Tissue Contrast.

The present disclosure provides for improving the described nanoparticle compositions for optimum targeting efficiency and sensitivity. It is noted that for every type of ligand/targeting moiety selected (e.g., PSMAi, e.g., GRPr inhibitor), the particle needs to be re-optimized to achieve optimum results for targeting efficiency and sensitivity. Accordingly, the number of ligands per particle and silica core size as a function of ligand number needs to be optimized, which, in turn, can affect the associated number of dyes per particle, as determined by a combination of FCS and optical spectroscopy. To that end, in addition to varying ligand number for a given nanoparticle size for higher discrete ligand numbers from about 5 to about 100 (e.g., from about 15 to about 20) in number, for which a detectable increase in particle size may occur, experiments can be performed in which the ligand number is kept constant, but the silica core diameter is varied to find optimum results in brightness and targeting efficiency. This can be achieved, e.g., by varying the time of the particle growth step after addition of silane to the aqueous reaction mixture and addition of PEG-silane quenching particle growth. Particle purification and characterization steps remain unchanged.

In Vitro Biological Properties of PSMA-C' Dots and GRPr-Targeting C' Dots.

Using conventional PSMA-expressing cell lines and GRPr-expressing cell lines, binding affinity, potency, and specificity of lead PSMAi-bound and GRP-bound C' dot candidates can be determined for their respective targets, PSMA and GRPr, based on competitive binding assays and optical detection methods. Results of each composition can be compared to those derived using prototype PSMAi-NOTA-C' dots and GRP-DOTA C' dots and native PSMA and GRP peptides. For example, the $IC_{50}$, or C'dot concentrations required to inhibit 50% of standard radiolabeled PSMAi agonist and GRP antagonist binding, can be determined for C' dot constructs over a concentration range from $10^{-13}$ to $10^{-5}$ mol/L. Competitive binding assays with $^{125}$I-[Bolton-Hunter] labeled Glu-urea-Lys (PSMAi) and $^{125}$I-(Tyr$^4$)-bombesin, as well as limited PK studies, can be performed for PSMAi and GRP peptide constructs. Moreover, cell trafficking of C' dots through the endocytic pathway can also be investigated using fluorescent reporters and examined for co-localization with ingested fluorescent particles using time-lapse microscopy.

Screen for Variations in PSMA and/or GRPr Target Expression Levels in Human Prostate Organoid Cultures and Metastatic Subclones of PC Lines to Select Lead Candidates for In Vivo Experiments.

Figure 22:
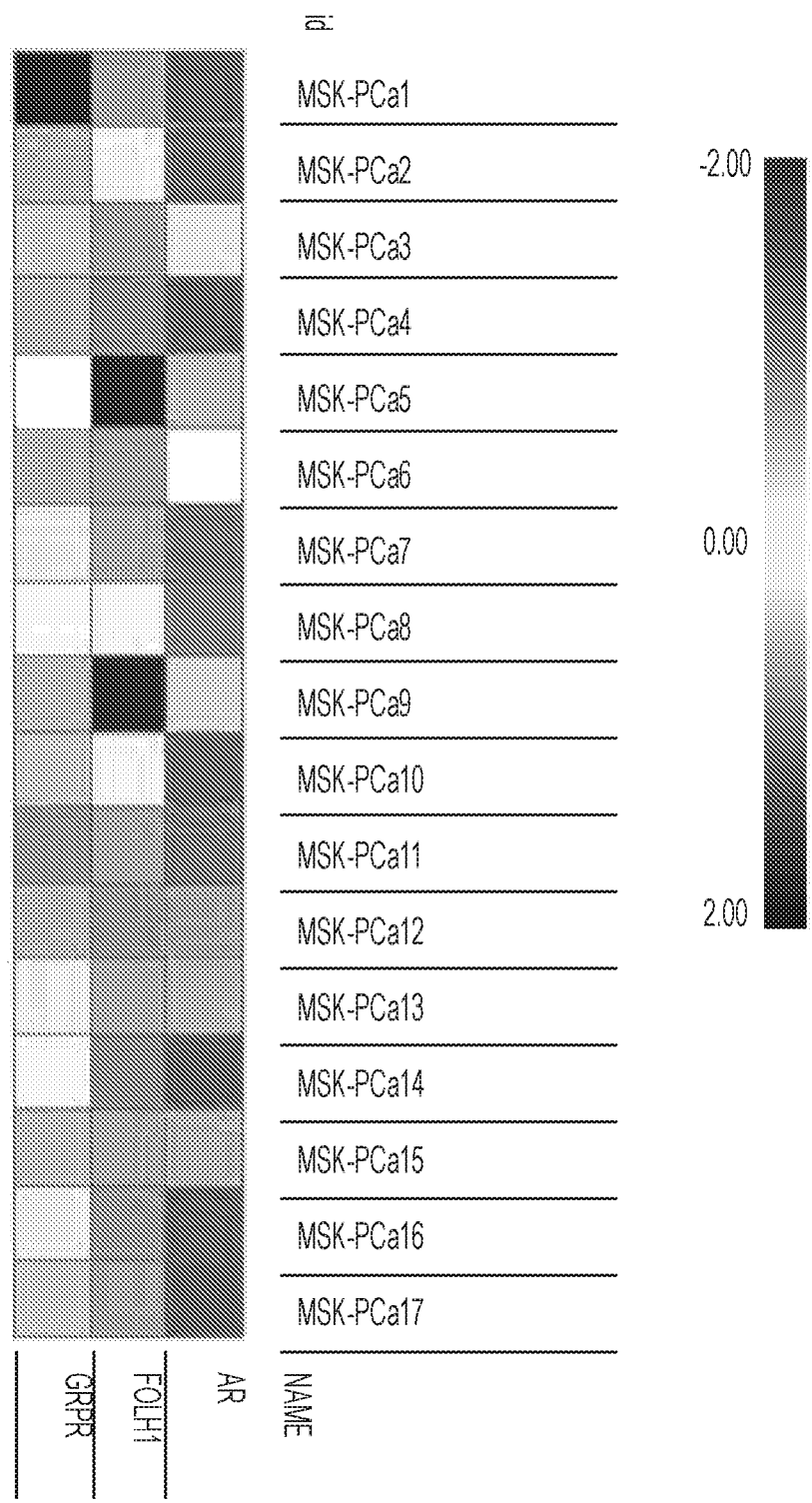
FIG. 22 depicts a heatmap showing Z-scores of gene expression of AR, PSMA, and GRPr.
Figure 23A:
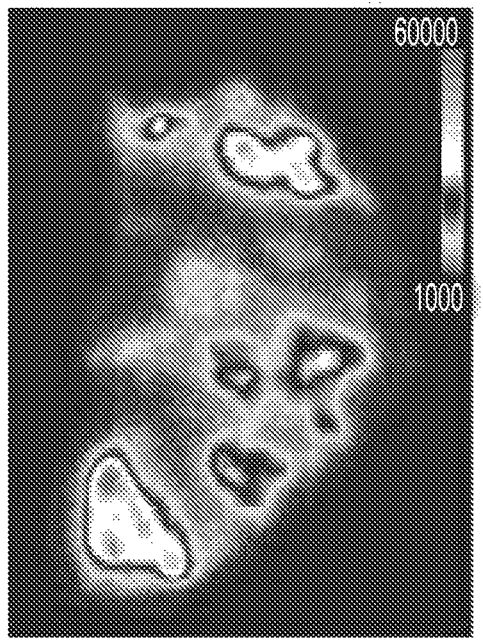
FIGS. 23A-23D show an analysis of PSMA expression in primary human PC.
Figure 23B:
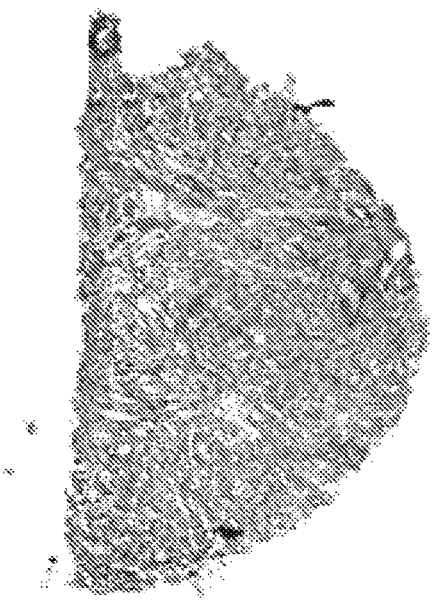
Figure 23C:
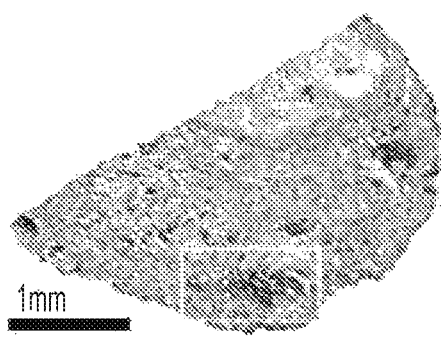
Figure 23D:
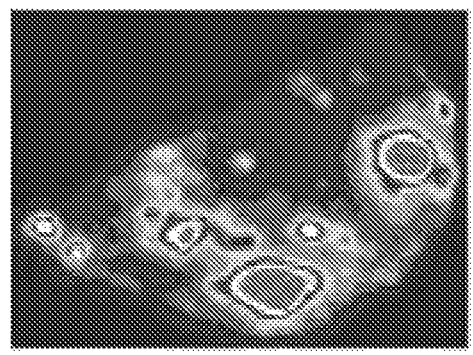
Figure 24A:
FIGS. 24A-24B show an analysis of GRPr expression in primary PC.
Figure 24B:
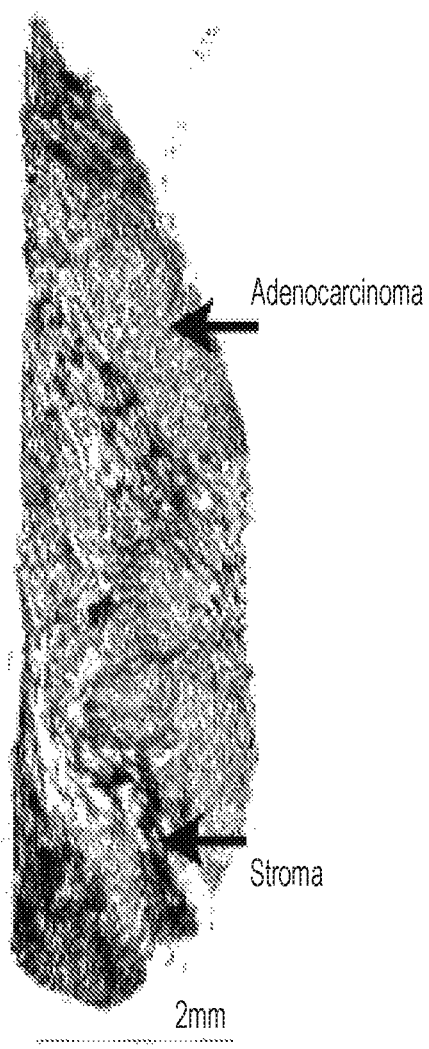

The described compositions can also be tested in human cell lines to select candidates for in vivo use. Antibody-mediated detection can be used to assess PSMA (Dako, M3620, Clone 3E6, 1:100 dilution) and GRPR (Abcam, ab39963; 5 µg/ml) target protein expression levels with IHC in (1) metastatic subclones of PC lines (e.g., LAPC4, VCaP); (2) patient-derived human prostate organoid cultures expressing PSMA (FOLH1) (n=7; e.g., MSK-PCa1, -PCa3, -PCa5, -PCa8, -PCa9, -PCa10, -PCa11) or GRPr transcripts (n=1; MSK-PCa1) by RNA-seq (FIG. 22); and (3) conventional cell lines (e.g., LNCaP, PC3), which serves as controls for their respective targets. For each marker, IHC staining intensity can be assigned a score of 1, 2, or 3 over the percentage intensity range of 1-100%. This, along with the % of PSMA- or GRPr-expressing cells, can be used to define an H score for selecting lead candidates for in vivo studies. Orthotopically-injected organoid cultures may develop cutaneous or metastatic tumors, as well as subclones with high metastatic efficiency, that lead to LN, bone, and other soft tissue metastases; these are highly relevant models as their genotypes/phenotypes recapitulate key features of human prostate biology. Cells that express targets of interests can be used for in vivo experiments.

Moreover, a maximum differential binding/uptake, specificity, $IC_{50}$, and toxicity of C' dots bearing variable numbers of targeting peptides can be used to select lead candidates. Following incubation of cells over a range of particle concentrations and incubation times, percent (%) binding can be determined by optical detection and/or gamma counting methods; % viable cells can be measured with a trypan blue cell viability assay (Vi-Cell Viability Analyzer).

In vitro binding experiments can be used to determine optimal peptide chemistries and targeted C' dot designs in conventional PC cell lines based up on maximum differential uptake and receptor binding parameters ($K_D$, $B_{max}$, $IC_{50}$). Rank tests with exact or permutation reference distributions can be used to compare the parameters across different numbers of ligands. To determine lead candidate cell lines for in vivo use, H scores can be compared using the same statistical methodology.

Constructive Example 3

Assess Tumor-Selective Uptake and PK Profiles of Optimized C' Dot Imaging Probes in PSMA- and GRPr-Positive Models to Identify Candidates with Favorable Targeting Kinetic and Clearance Profiles.
Radionuclides A variety of radionuclides can be used with the described compositions. For example, Copper-64 ($t_{1/2}$=12.7 hours, $\beta^+$=0.65 MeV, ($\beta^-$=0.58 MeV) half-life and decay characteristics are well-matched with the biodistribution of the particle, and are suitable for PET imaging. Alternatively, for example, Gallium-67 ($t_{1/2}$=78 hours, 91, 93, 185, 296 and 388 keV γ-emissions) decays by electron capture, and can be imaged by SPECT. Both Copper and Gallium are efficiently chelated by NOTA. The longer half-life allows imaging at time points later that 24 h. Moreover, Zirconium-89 ($t_{1/2}$=78 hours, $\beta^+_{avg}$=395 keV) is a positron emitting radionuclide that can be used for PET imaging at longer time points consistent with the pharmacokinetics of the C' dots. $^{89}$Zr can be chelated by DFO or directly coordinated to microporous silica nanoparticles via surface silanol groups.
Radiolabeled PSMAi-NOTA- and GRP-DOTA-C' Dots PSMAi-NOTA-C' dots (21 µmol) were radiolabeled with $^{64}$Cu or $^{177}$Lu (210 pmol) in NH$_4$Ac buffer pH 5.5 at 70° C. for 20 min. The average radiolabeling yields were 98.6% and 99.3% radiochemical purities of 98% and 99.9%. Stabilities of the radiolabeled particle complexes were examined in water, saline, and serum (Table 1).

Table 1 shows percent radiolabeled C' dot stability.

TABLE 1

| Particle | PSMAi-($^{64}$Cu)NOTA-C' dots | | | GRP-($^{177}$Lu)DOTA-C'dots | | |
|---|---|---|---|---|---|---|
| Time | 1 h | 4 h | 24 h | 1 h | 4 h | 24 h |
| H$_2$O | 97.4 | 97.1 | 95.3 | 99.9 | 99.8 | 99.9 |
| PBS | 97.5 | 96.2 | 92.9 | 99.9 | 99.9 | 99.9 |
| Mouse S | 98.6 | 97.3 | 95.3 | 99.9 | 99.8 | 98.6 |
| Human S | 99.8 | 99.1 | 97.6 | 99.9 | 99.9 | 99.8 |

Radiolabeled Particle Cell Binding

Figure 11A:
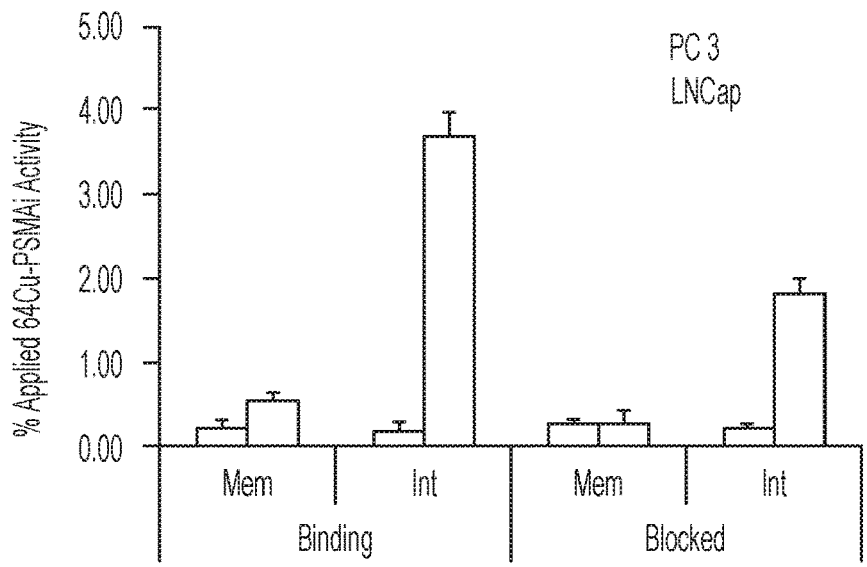
FIGS. 11A-11B show cell binding of (FIG. 11A) PSMAi-($^{64}$Cu)NOTA-C' dots and (FIG. 11B) GRP-($^{177}$Lu)DOTA-C' dots to PC3 and LNCaP PC cell membrane (Mem) and internalized (Int) fractions. Each data point represents the mean ±sd of 3 replicates.
Figure 11B:
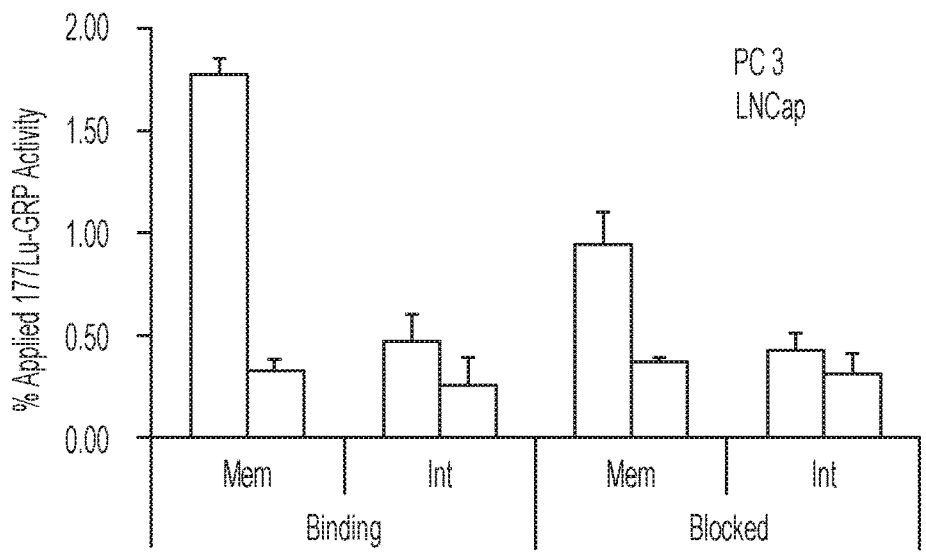
Figure 11C:
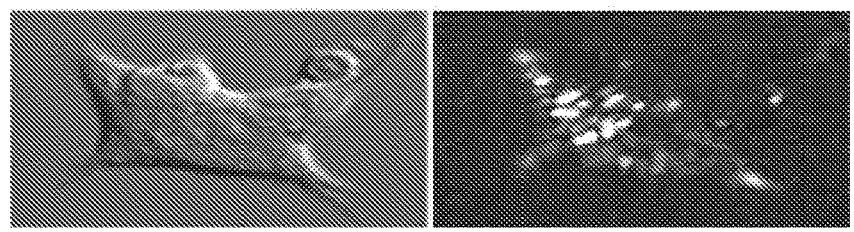
FIG. 11C shows localization of PSMAi-PEG-C' dots (1 μM, pink) in 22RV1 cells 4 h post-incubation.

PSMAi-($^{64}$Cu)NOTA-C' dots and GRP-($^{177}$Lu)DOTA-C' dots were examined for cell binding with LNCaP and PC3 cells (FIGS. 11A-11C). Cells were incubated with 100,000 CPM of PD10 purified radiolabeled C' dots. PMPA and bombesin were used for blocking PSMAi and GRP radiolabeled C' dots. After 3 PBS washes, the membrane surface-bound fraction was removed with 40 mM NaOAc (pH=4.5, 0.9% NaCl, 0.2% BSA), after which the cells were dissolved in NaOH to obtain internalized counts. A time course uptake study at 1 h, 4 h, and 24 h revealed optimal binding was achieved at 24 h. Bound PSMAi-($^{64}$Cu)NOTA-C' dots were internalized into LNCaP cells. Binding and internalization were blocked by the PSMA inhibitor PMPA, demonstrating PSMA specificity. PC3 cells, which do not express PSMA, displayed significantly less binding. Similar results were obtained with PSMAi-($^{67}$Ga)NOTA-C' dots (data not shown). GRP-($^{177}$Lu)DOTA-C' dots bound PC3 cells, but were not efficiently internalized. Binding was blocked by bombesin, demonstrating specificity for GRPr. Only low levels of binding where observed with LNCaP cells, which do not express GRPr.

Figure 12:
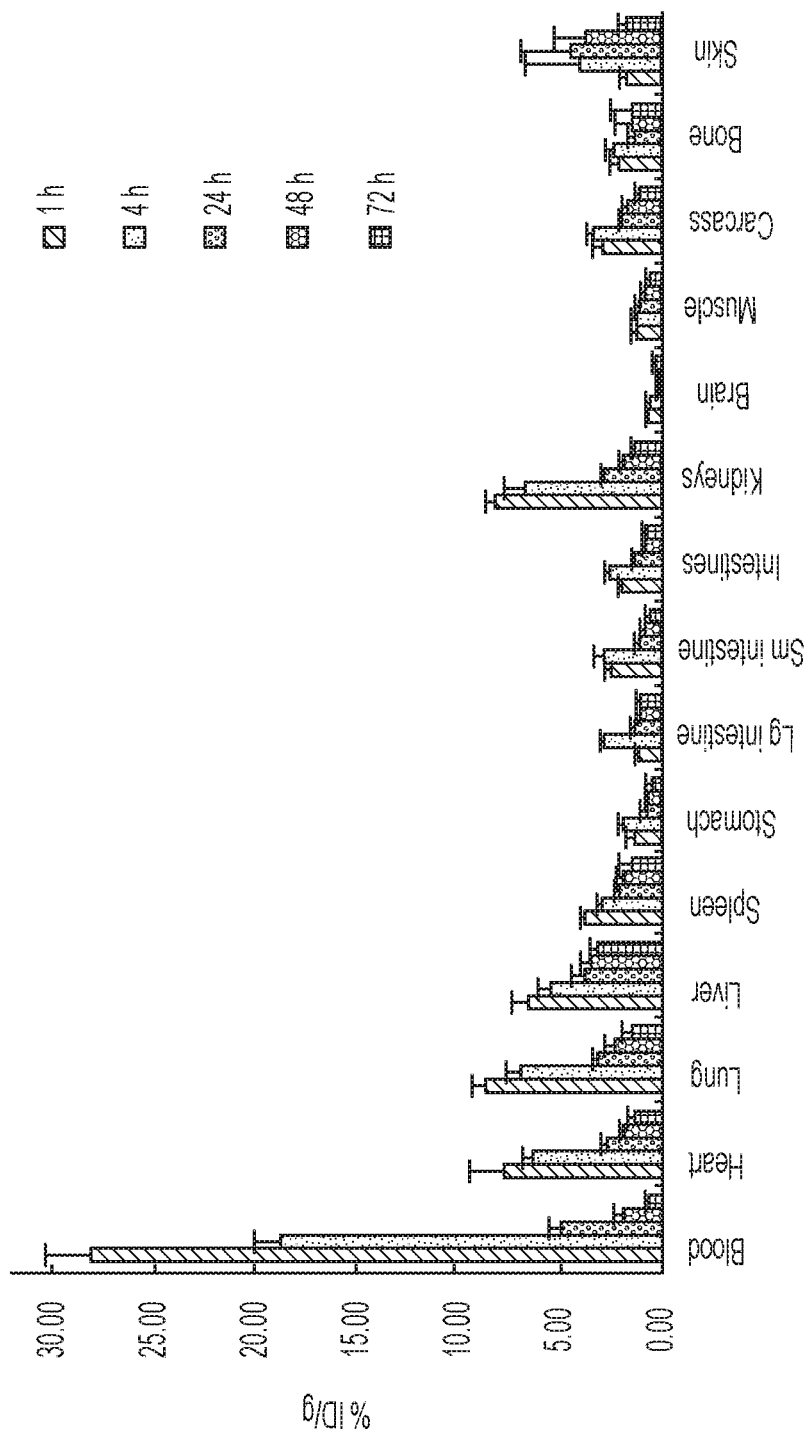
FIG. 12 shows biodistribution of PSMAi-($^{64}$Cu)NOTA-C' dots in normal CD-1 mice at 1 h, 4 h, 24 h, 48 h, 72 h p.i. Data are reported as mean percent injected dose per gram of tissue (n=4 mice/time point).

Biodistribution and Tumor Targeting with $^{64}$Cu- and $^{89}$Zr-Labeled PSMAi-C' Dots PSMAi-NOTA-C' dots, radiolabeled with $^{64}$Cu, and purified on a PD10 column had a RCP of 97.5% and specific activity of 2.46 Ci/μmol. Normal CD-1 mice were injected via the tail vein with 20 μCi of PSMAi-($^{64}$Cu)NOTA-C' dots in 100 μl of saline. Groups of mice were sacrificed at pre-determined time points, tissues dissected and weighed, and radioactivity quantitated. FIG. 12 shows data presented as percent injected dose per gram (% ID/g) of tissue. Disappearance of the PSMAi-($^{64}$Cu)NOTA-C' dots from the blood was rapid with primary excretion via the kidneys. At 24-h p.i., particle uptake in normal tissues was less than 5% ID/g, including liver and spleen. Dosimetry calculations were performed using a standard person (70 Kg) Medical Internal Radiation Dose formalism. PK data in C57 mice were calculated using OLINDA (Table 2). Dosimetry was found to be favorable on a per mCi basis in normal organs, comparable to those of other commonly used diagnostic radiotracers. The data did not raise concerns about excessive normal organ doses.

TABLE 2

| Tissue | Absorbed Dose (rad/mCi) |
|---|---|
| Adrenals | 0.0445 |
| Brain | 0.0123 |
| Breasts | 0.0311 |
| Gall bladder Wall | 0.0483 |
| Low Lg Intestine Wall | 0.145 |
| Small Intestine | 0.178 |
| Stomach Wall | 0.048 |
| Upper Lg Intestine | 0.114 |
| Heart wall | 0.064 |
| Kidneys | 0.547 |
| Liver | 1.25 |
| Lungs | 0.107 |
| Muscle | 0.0158 |
| Ovaries | 0.0460 |
| Pancreas | 0.0443 |
| Red Marrow | 0.0579 |
| Bone | 0.113 |
| Skin | 0.0274 |
| Spleen | 0.0632 |
| Testes | 0.0336 |
| Thymus | 0.0311 |

TABLE 2-continued

| Tissue | Absorbed Dose (rad/mCi) |
|---|---|
| Thyroid | 0.567 |
| Bladder Wall | 0.153 |
| Uterus | 0.0459 |
| Total Body | 0.0838 |
| Effective Dose (rem/mCi) | 0.0835 |

Figure 13:
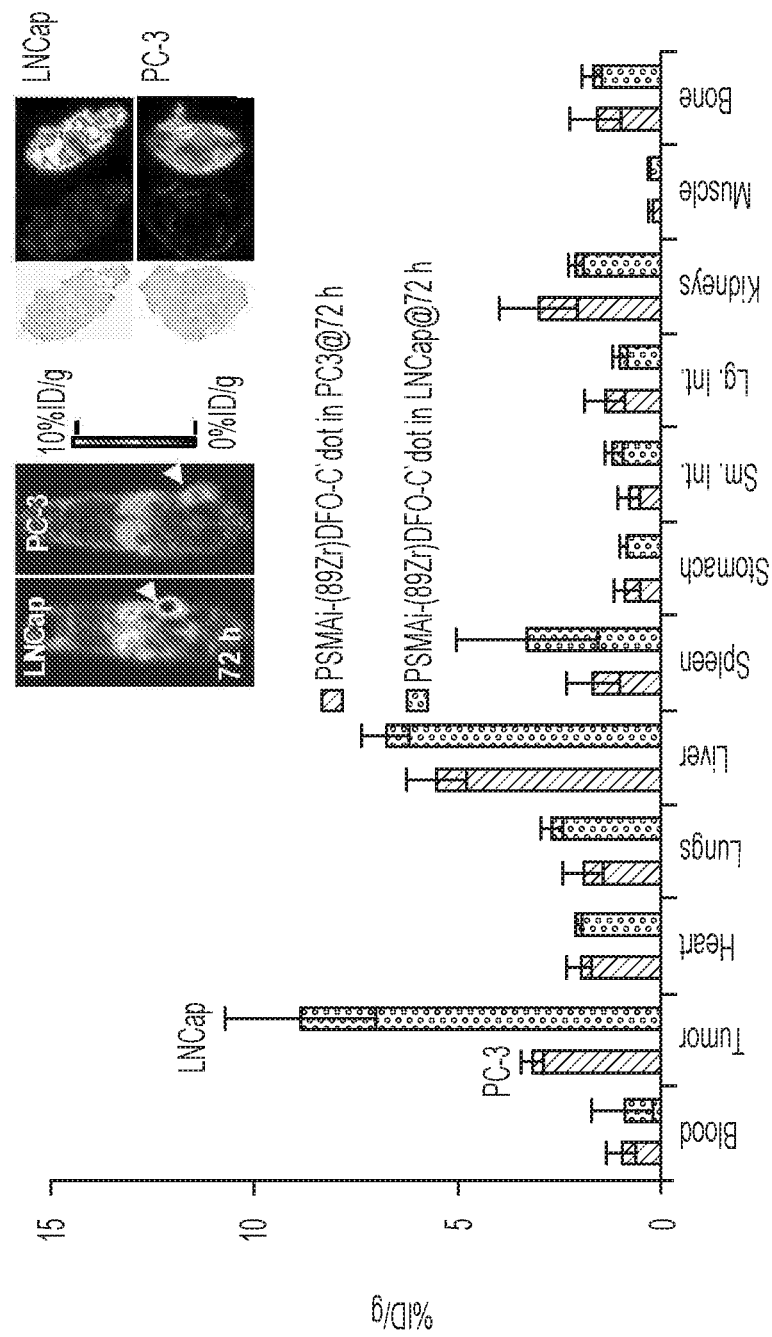
FIG. 13 shows a biodistribution study of PSMAi-$^{89}$ZR (DFO)-C' dots in PC-3 (n=5) and LNCaP (n=2) tumor-bearing mice. Bars represent mean % ID/g±sd. Inset: 72 h PET scan p.i. with corresponding histology, and autoradiography of probes.

$^{89}$Zr-labeled PSMAi-C' dots (e.g., PSMAi-($^{89}$Zr)DFO-C' dots) were also developed and tested for specific tumor targeting in PSMAi-positive (LNCaP) and negative tumor (PC-3) models. As shown in FIG. 13, (inset), more than a two-fold tumor uptake enhancement (~9% ID/g vs ~3.5% ID/g) was observed in LNCaP tumor-bearing mice. Ex vivo biodistribution at 72-h p.i. further confirmed the specific tumor uptake of as-designed probes (FIG. 13). In vivo radiostability was greater than 90% at 24-h p.i. Autoradiography further confirmed specific uptake and tissue penetration of PSMAi-($^{89}$Zr)DFO-C' dots in a PSMA-positive tumor model (FIG. 13—inset).

Methods

Following optimization of labeling procedures with radiometals, screening assays can determine which lead candidate particle probes and cell lines can be selected for internalization, PK, and tumor-targeting studies. For example, targeting efficiency, clearance, dosimetry, and product radiostability, established by initial PK evaluations in tumor-bearing mice, can be used to identify a lead particle product for in vivo imaging evaluations of primary lesions and metastatic disease with histologic correlation.

Optimize Surface Radiolabeling Conditions for PSMAi-Conjugated-C' Dots and GRP-Conjugated-C' Dots with $^{64}$Cu, $^{67}$Ga, or $^{89}$Zr.

In the final step, PSMA and GRPr targeted C' dots can be radiolabeled with $^{64}$Cu and $^{67}$Ga at various concentrations (~0.3-300 nmol) in acetate buffer (pH 5.5) for 30 min and at 70° C. to obtain PSMAi-($^{64}$Cu)NOTA-C' dots and GRP-($^{67}$Ga)DOTA-C' dots. For $^{89}$Zr labeling, as-synthesized PSMAi-DFO-C' dot can be incubated with $^{89}$Zr-oxalate at 37° C. for 30 min (pH 7-8). Radiolabeled PSMA-targeting C' dots and GRPr-targeting C' dots can be purified using PD-10 (G-25) size exclusion chromatography. For radiolabeling experiments, specific radiolabeling parameters can be determined for optimal radiolabeling efficiencies and high specific activities. Labeling can begin with the conditions shown to produce the highest specific activity. Quality control includes ITLC, HPLC, and cell-based receptor binding bioassays. Stability of radiolabeled C' dots can be determined in H$_2$O, PBS at 25° C. and mouse and human serum at 37° C.

Cellular Internalization and Efflux of Radiolabeled C' Dots.

Using radiolabeled particle conjugates, particle distributions within PSMA-expressing and GRPr-expressing LNCaP and PC3 cells can be investigated on the basis of binding and internalization studies with time-lapse microscopy and in vitro assays. Radiolabeled C' dot tracers can be incubated with cells over time (0.5-4 h), washed with acidic buffer to remove membrane-bound particles, and radioactivity quantified in cellular and acidic wash fractions. Binding specificity can be determined by incubation of C' dot tracers with excess non-radiolabeled PSMAi and GRP peptides and C' dots over the same time frame as the binding study. Efflux of radioactivity can be determined by allowing cellular uptake of radiolabeled particles, washing with acidic buffer, changing the cell media, and monitoring the release of radioactivity back into the media. Non-specific binding can be determined by blocking the receptor target with PMPA for PSMA and RM2 peptide for GRPr antagonist binding.

Moreover, PK screening and in vivo imaging of lead PSMAi-conjugated C' dot tracers and GRP-conjugated C' dot tracers in subcutaneous and orthotopic models derived from conventional/metastatic cell lines, as well as human prostate organoid-based models maximally expressing one/both targets, to identify probes with favorable targeting/clearance kinetics can be performed.

For example, screening PK studies of the provided compositions can be performed after intravenous (i.v.) injection of each radiolabeled lead candidate PSMA-, GRPr-targeting particle tracer into (i) non tumor-bearing athymic nu/nu mice (n=3 mice/C' dot tracer; —20 µCi/mouse) and (ii) separate cohorts of NOD-SCID (NOD.CB17-Prkdc$^{scid}$) tumor-bearing mice (at least 3 animals per cohort). For example, the following tumor xenografts can be investigated: conventional models using $15.0\times10^6$ cells (e.g., LNCaP, 22RV1, PC3), metastatic subclones using $15.0\times10^6$ cells (e.g., PSMA+ expressing LAPC4, VCaP), and organoid models using $5.0\times10^5$ cells. Additional cohorts serve as biological controls (e.g., PC3, for a non-PSMA model). Mice can be sacrificed at 4 specified time points up to 72 hours p.i. to select lead C' dot products for subsequent PET and SPECT imaging. Decay-corrected percentage of the injected dose per gram (% ID/g) values of major organs, tumor, blood, and urine can be assessed in a scintillation well-counter. Analytical radioHPLC and radioTLC can be used to assess Radiostability and Metabolites in Biological Specimens.

In vivo PET imaging and Analysis.

Particle tracers and tumor models yielding maximum targeted tumor uptake, clearance profiles, dosimetry, and radiostability can be used to identify a single lead PSMAi-functionalized C' dot probe or GRP-functionalized C' dot probe for PET and SPECT imaging, as well as for metastatic nodal mapping experiments. For imaging evaluations, separate cohorts of mice (n=10 per cohort) can be serially scanned (e.g., 15-30 min static images) over a 72-hr interval after i.v.-injection of ~300 µCi C' dot tracer/mouse. Region-of-interest (ROI) analyses can be performed over the tumor region and over major organs/tissues to record mean activities and target-to-background ratios.

Constructive Example 4

Develop Spectrally-Distinct NIR Dye-Containing Products from Lead C' Dot Candidates to Identify PSMA-Expressing Nodal Metastases, GRPr-Expressing Nodal Metastases in Preclinical Models Using Multiplexing Strategies and Correlative Histology The provided compositions can comprise spectrally-distinct NIR dye-containing products to identify nodal mestases in preclinical models.

For example, as shown in FIG. 14, Cy5.5 and CW800 dye-silane conjugates were added into the reaction mixture, together with TMOS, to generate the dye-encapsulating silica core, which is surface-functionalized to produce the final targeted and radiolabeled particle products—all as a 1-pot process. By FCS, per particle size and brightness indices were determined for representative batches of PSMAi-PEG-Cy5.5- (Table 3) and GRP-PEG-CW800-C' dots (Table 4) used herein.

TABLE 3

FCS measurements of cw800 channel

| Sample | Diameter (nm) | Dye Equivalent | Quantum Enhancement |
|---|---|---|---|
| cw800 Maleimide dye | 1.6 | 1 | 1 |
| GRP-PEG-cw800-C' dots | 6.0 | 2.8 | ~2 |

TABLE 4

FCS measurements of Cy5.5 channel

| Sample | Diameter | Dye Equivalent | Quantum Enhancement |
|---|---|---|---|
| Cy5.5 Maleimide dye | 1.3 | 1 | 1 |
| PSMAi-PEG-Cy5.5-C' dots | 6.2 | 1.5 | 1.8 |

In contrast to conventional methods that typically either utilize non-specific fluorescent dyes or probes that bind to a single target, a multiplexing imaging strategy that enables the simultaneous optical detection of multiple cancer markers within the lymphatic system can be used, in accordance with certain embodiments. This may facilitate the earlier detection, improved characterization, and more accurate localization of molecular cancer phenotypes in the intraoperative setting. In animal models and humans, such multiplexing tools offer detection capabilities needed to address heterogeneity of cancer target expression, staging, and treatment management. Further, these imaging strategies serve as reliable, real-time intraoperative roadmaps to guide the operating surgeon during SLN biopsy or resection.

Figure 15:
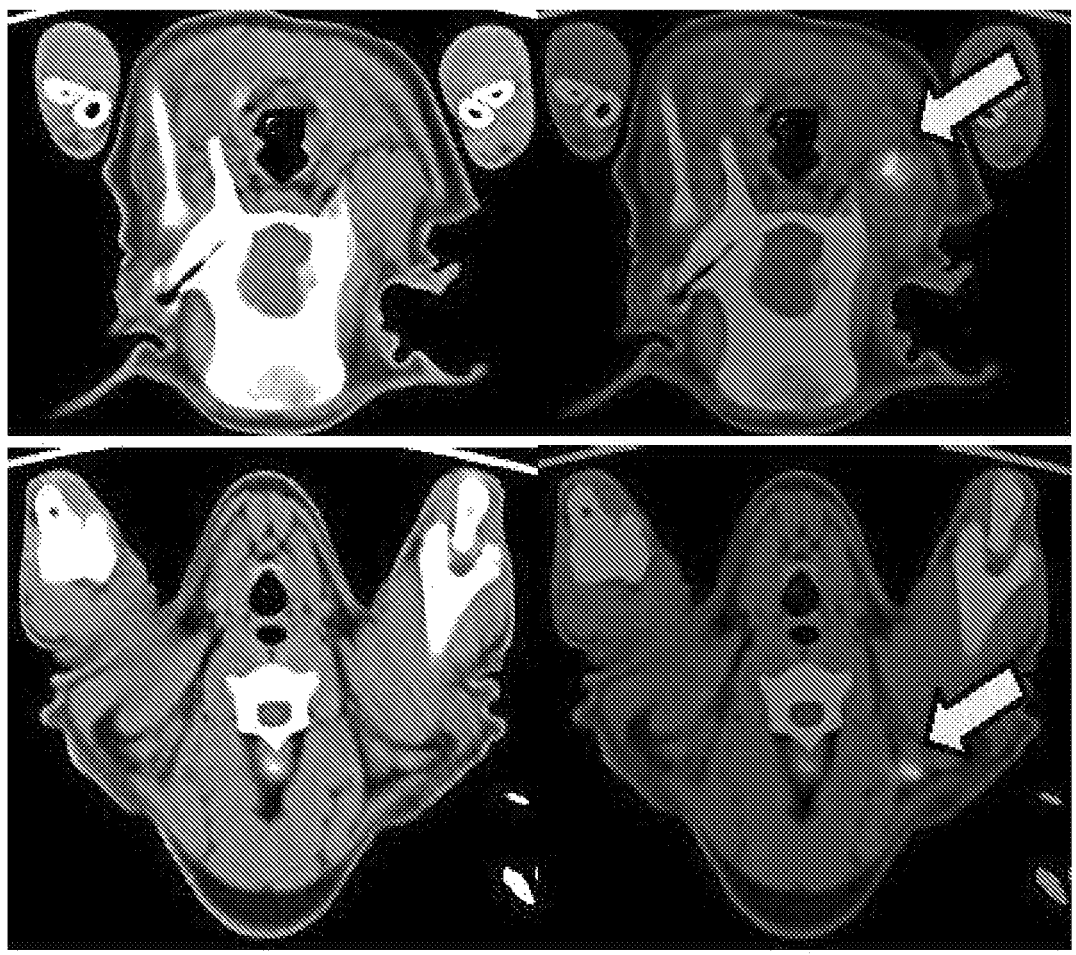
FIG. 15 shows a screening pre-operative modal mapping PET study in a metastatic melanoma miniswine with $^{124}$I-cRGDY-CW800-C'dots ("cRGDY" disclosed as SEQ ID NO: 1).

In proof-of-concept larger-animal metastatic melanoma studies, fluorescence-based multiplexing studies (along with preoperative PET) were conducted to determine whether real-time image-guided tumor phenotyping, using particle-mediated detection, identify metastatic nodes by assaying multiple cancer markers, specifically integrins and melanocortin-1 receptor, MC1-R (e.g., target of α-melanocyte stimulating hormone, αMSH). Two spectrally-distinct NIR dye-containing C' dots, each functionalized with a different melanoma-directed peptide (e.g., cRGDY-PEG-CW800-C'dots ("cRGDY" disclosed as SEQ ID NO: 1) and αMSH-PEG-Cy5.5-C'dots) were employed. In a representative miniswine, PET-CT screening was initially performed for identifying metastatic nodal disease after subdermal, peritumoral injection of one of these radiolabeled particles, $^{124}$I-cRGDY-PEG-CW800-C'dots ("cRGDY" disclosed as SEQ ID NO: 1), about a paravertebral melanomatous lesion (not shown). PET-avid nodes (arrows) were seen in the left upper/lower neck on high resolution PET-CT imaging (FIG. 15, right upper, lower panels). Nodes were marked, and the pig taken to the operating room for co-injection of 2.0 nanomoles each of spectrally-distinct "cold" cRGDY-PEG-CW800-C'dots ("cRGDY" disclosed as SEQ ID NO: 1) and αMSH-PEG-Cy5.5-C' dots (FIG. 16A). Real-time optical imaging guidance was performed showing high fluorescence signal localized to the tumor lymphatics and nodes draining the primary tumor site (top to bottom). Signal in pathology-proven high (FIG. 16A; row 3) and low (FIG. 16A; row 5) tumor burden lymph nodes were detected in the 700 nm (green; αMSH-Cy5.5-C' dots) and 800 nm (red; cRGDY-CW800-C' dots ("cRGDY" disclosed as SEQ ID NO: 1)) channels of a multichannel fluorescence camera system; yellow signal reflects co-expression of both signals (e.g., markers) in each node. Correlative histopathology of the high tumor burden node (FIG. 16B, upper panel) shows complete replacement of the node with melanoma on H&E staining and corresponding high Cy5.5 fluorescence signal on high power confocal microscopy images. The relative fluorescent intensities of sections taken from this high tumor burden node (FIG. 16B, lower panel) also shows co-localization of both MC1R- and integrin-targeting particles with DAPI counterstaining. Without wishing to be bound to any theory, this data suggests specific binding/accumulation of particle probes in this melanoma-replaced node. To increase the sensitivity of detection of micrometastases, and to allow distinction between melanoma cells and melanin-laden macrophages, selected sections were stained by immunohistochemistry (IHC) for HMB-45 and MITF, as well as integrins (FIG. 16C). MiTF, a transcription factor upregulated by MC1-R activation in melanoma cells, was positive in multiple sections taken from the high tumor burden node ('LN') and primary tumor tissue.

Transgenic Mouse Models of PC for Mapping of Metastatic Disease in Lymph Nodes and Other Tissues The examples provided herein use the transgenic adenocarcinoma mouse prostate (TRAMP) cancer model. Prostate cancer develops in mice in which the SV40-T antigen oncogene is driven by the rat probasin gene promoter in the prostate epithelium. The TRAMP model is characterized by the development of prostatic neuroendocrine carcinoma in 4-7 months with metastases forming in the LNs, lung, adrenal gland and bone in 4-9 months. The incidence of metastases is nearly 100%.

Figure 17:
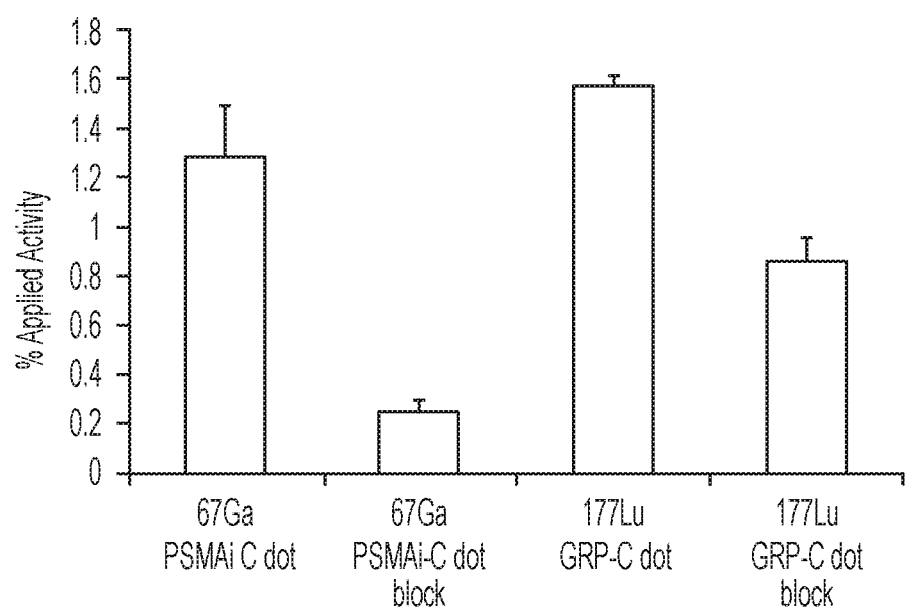
FIG. 17 shows cell biding of $^{67}$Ga(NOTA)-PSMAi-C' dots and $^{177}$Lu(DOTA)-PSMAi-C' dots to the TRAMP C2 cell line alone or in the presence of a selective inhibitor.

The advantages of the TRAMP model are the development of disease that mirrors human pathology in an immune competent mouse, coupled with the formation of LN and bone metastases. Disadvantages are that the biology/physiology of mouse prostate is not the same as the human organ. For example, the mouse prostate is not a single organ, as in human, but has 4 lobes, different from the single organ human prostate. The advantage of the TRAMP model is the ability to image metastatic disease and nodal metastases with PSMA- and GRPr-targeting C' dots using PET and fluorescence-based multiplexing. Binding studies of PSMAi-($^{67}$Ga)NOTA-C' dots and GRP-($^{177}$Lu)DOTA-C' dots to the TRAMP-C2 cell line were examined (FIG. 17). The TRAMP-C2 cell line was derived from TRAMP prostate tumors. Both the PSMAi-($^{67}$Ga)NOTA-C' dots and GRP-($^{177}$Lu)DOTA-C' dots bound the TRAMP-C2 cell line. PSMAi-($^{67}$Ga)NOTA-C' dot binding can be reduced dramatically with addition of the PSMA inhibitor, PMPA, while GRP-($^{177}$Lu)DOTA-C' dot binding was significantly reduced by addition of an excess of GRPr targeting RM2 peptide, which demonstrated selective and receptor-mediated binding to the TRAMP cell line for both C' dot conjugates. This model enables proof-of-concept studies to be conducted for multiplexed detection of nodal metastases using a cocktail of PSMAi-PEG-Cy5.5-C' dots and GRP-PEG-CW800-C' dots.

Figure 18A:
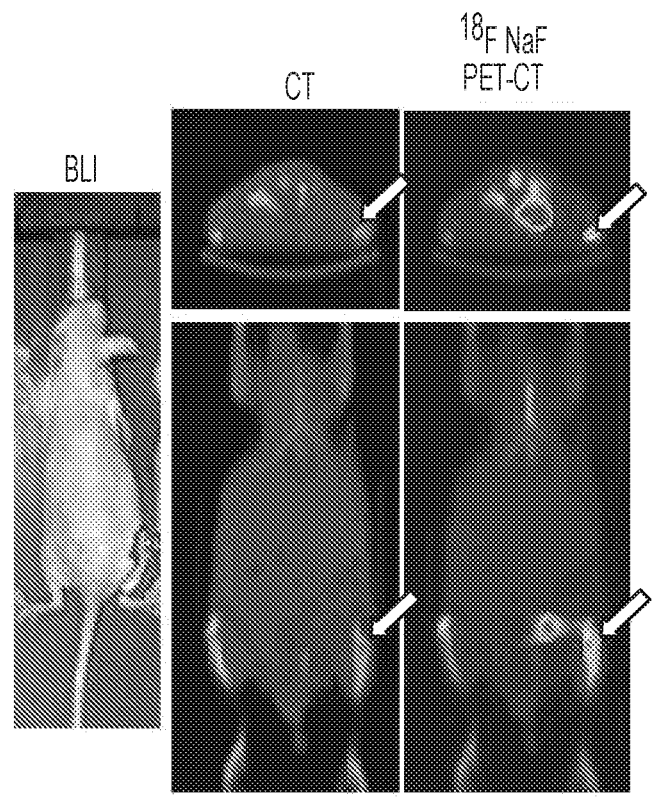
FIG. 18A shows bony metastases (arrow) arising from the LAPC4 sub-clone 4 weeks after intra-cardiac injection of luciferase-expressing cells using bioluminescence imaging (BLI) and $^{18}$F—NaF PET-CT imaging (arrows).
Figure 18B:
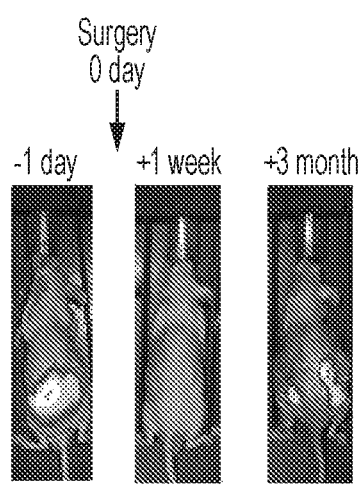
FIG. 18B shows spontaneous distal metastases of LAPC4 sub-clone were identified on BLI.
Figure 18C:
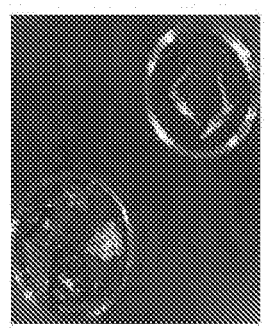
FIG. 18C shows BLI of different organs harvested in B showing metastases in liver, kidney and femur.

Although mouse models have made contributions to the identification of genetic lesions involved in high-grade prostatic intraepithelial neoplasia lesions and locally invasive prostate cancer, most mouse models are less accurate in modeling the progression to metastatic disease. Recently, several spontaneous and experimental metastatic models, such as LAPC4 (and VCaP) subclones have shown high metastatic efficiency (e.g., —70-80%; unpublished data), with resulting features of hormone-dependent growth and metastases. One such LAPC4 metastatic subclone (FIGS. 18A-18C) may better recapitulate human disease. Following intra-cardiac injection of a luciferase (luc+)-expressing LAPC4 metastatic subclone, mice were monitored weekly with bioluminescence imaging (BLI) and $^{18}$F-sodium fluoride (NaF). Using this model, metastatic tumor was detected on dual-modality (PET-BLI) imaging in multiple organs (liver, kidney and bone) in 80% of mice over the course of several months.

Methods

These studies can be performed in parallel with Phase 1 clinical trials, and can serve to identify and qualify reliable biomarkers that can be validated in Phase 1 trials and in multiplexing clinical trial designs.

TRAMP Model

On the basis of data showing co-expression of PSMA and GRPr (FIG. 17) targets in the well-established TRAMP mouse model (https://www.jax.org/strain/003135), an initial screen of TRAMP mice can be performed for metastatic nodes and other sites of metastatic disease (e.g., bone) by at least 30 weeks of age following i.v. injection of $^{18}$F-fluorodeoxyglucose ($^{18}$F-FDG) using PET-CT imaging. This can be followed by a single-dose i.v. injection (1-2 days later) of lead dual-modality (PET-optical) C' dot probes for targeting tumor, nodes, or other metastases expressing (i) PSMA (n=10 mice), (ii) GRPr (n=10 mice), or (iii) both markers (n=10 mice).

In accordance with certain embodiments, a multispectral fluorescence camera system (e.g., Quest Spectrum) for multiplexed detection of nodal disease (see data, FIGS. 16A-16C) is used to image the described compositions. In these studies, the timing of disease localization can be optimized by weekly hybrid PET-MR imaging scans following i.v. particle tracer injection. Once PET-avid disease is identified, optical signal intensity can be assessed as to whether it is adequate to visualize sites of metastatic disease (e.g., nodes) following surgical exposure and using the Quest Spectrum™ camera for detecting optical signal in one or both fluorescence channels (e.g., Cy5.5, CW800).

When the foregoing conditions have been determined for primary/metastatic disease detection for each lead candidate C' dot probe in this model, the experiments can be repeated as a multiplexing experiment to acquire data for each non-radiolabeled probe independently (n=10 mice/C' dot probe), and then together (n=10 mice). For NIR optical imaging evaluations, maximum in situ tumor, nodal, and background signal intensities can be measured using ROI analysis tools for the camera system (Architector Vision Suite, QMI), and contrast-to-background ratios needs to be greater than or equal to 1.1 (used in clinical trial studies) to be considered positive. Importantly, in vivo detection sensitivity can also be determined by injecting serial particle dilutions into the prostate gland itself and measuring optical signal at different gains, exposure times, and camera working distances.

Metastatic Models (LAPC4, VCaP, PC3).

The procedure described above can then be applied to a spontaneous metastatic model by orthotopically-injecting $5.0 \times 10^5$ luciferase (luc+)-expressing VCaP, LAPC4, or PC3 cells into the prostate gland of NOD-SCID mice (n=10 mice per cell type) via laparotomy. The primary tumor can be surgically removed 3 weeks p.i. to enable long-term monitoring of metastatic nodal disease. Primary and metastatic tumor can be imaged weekly by BLI. For these highly metastatic models, metastases can be detected systemically, including LNs, in ~70% of the mice over a 3-4 week interval p.i.

Figure 19:
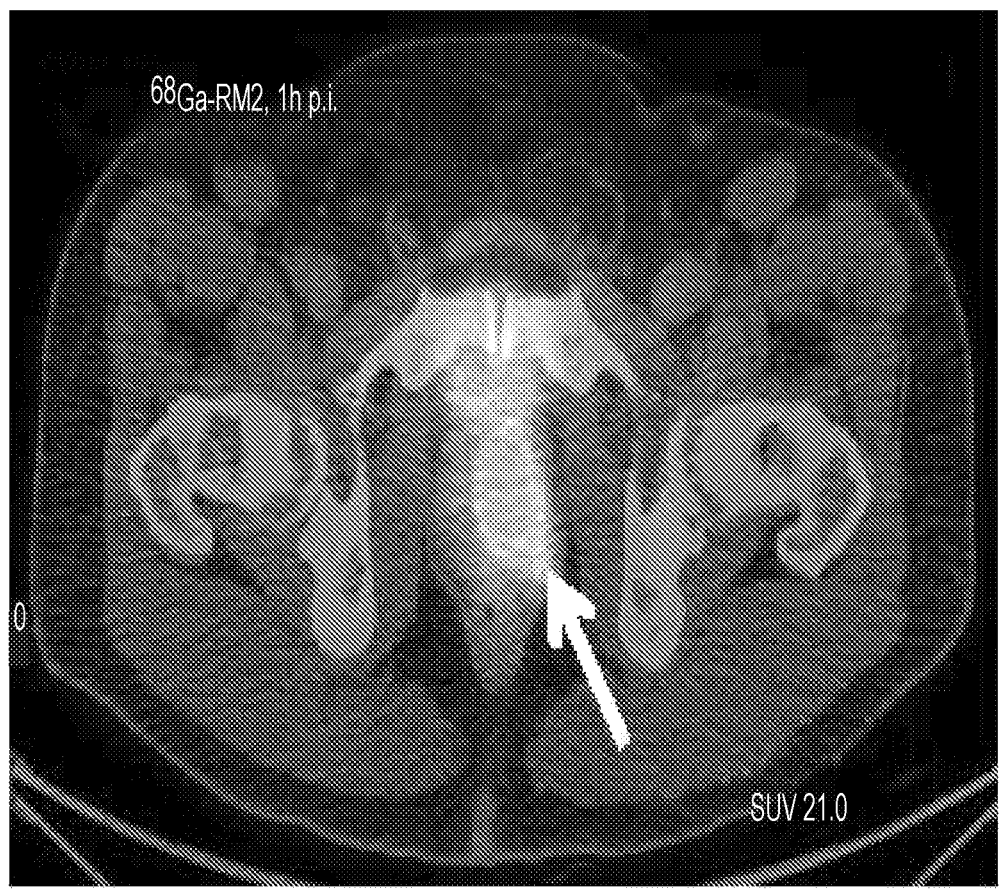
FIG. 19 shows uptake of $^{68}$Ga-RM2 (GRPr ligand) in a patient with newly diagnosed Gleason 9 PC.
Figure 20A:
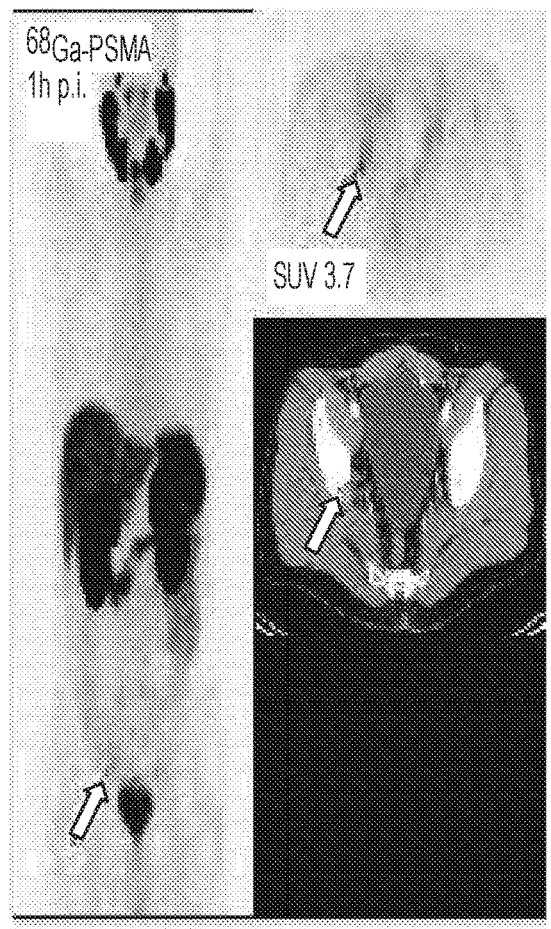
FIGS. 20A-20B show a patient with biochemical recurrence of PC imaged with PSMA ligand $^{68}$Ga-PSMA-11 and GRPr ligand $^{68}$Ga-RM2. $^{68}$Ga-PSMA-11 scan acquired 4 weeks after the $^{68}$Ga-RM2 scan. Retroperitoneal LN metastases are better visualized on the GRPr scan than on the PSMA scan.
Figure 20B:
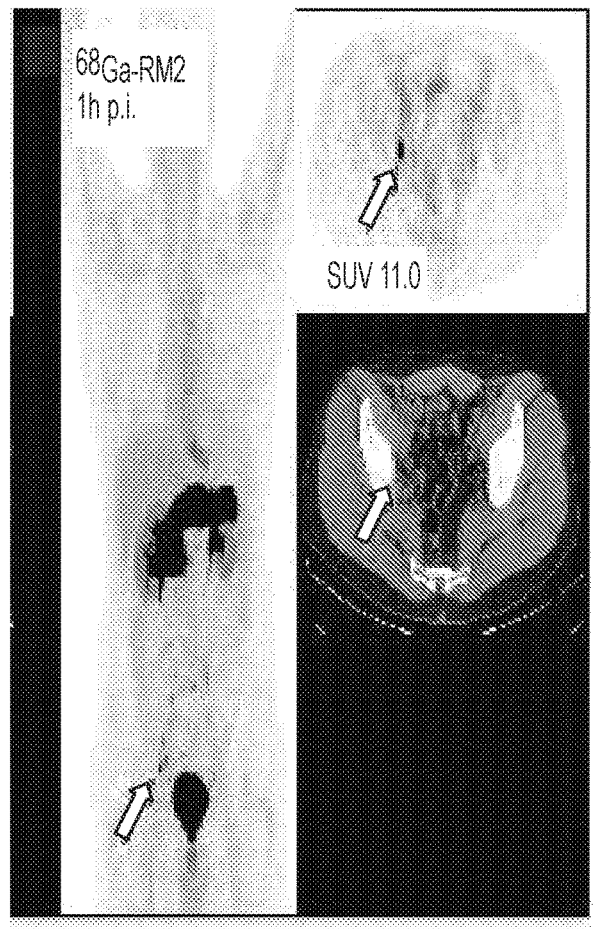

Clinical PET experiments have demonstrated high uptake of the $^{68}$Ga-RM2 tracer in a newly-diagnosed PC lesion (FIG. 19) or in metastatic LNs in a patient with biochemical recurrence of PC (FIGS. 20A-20B). In the latter case, both $^{68}$Ga-RM2 and -PSMA-11 tracers were administered, noting significantly better visualization of nodes with $^{68}$Ga-RM2; this observation underscores the importance of examining multiple clinical PC markers in these patient cohorts. Of note, very high RES and renal uptake is noted for the PSMA-targeting probe (left panel), in addition to high pancreatic uptake for the $^{68}$Ga-RM2 probe (right panel).

What is claimed is:

1. A composition comprising a prostate specific membrane antigen inhibitor (PSMAi)/chelator construct covalently attached to a macromolecule, wherein the construct has the structure:

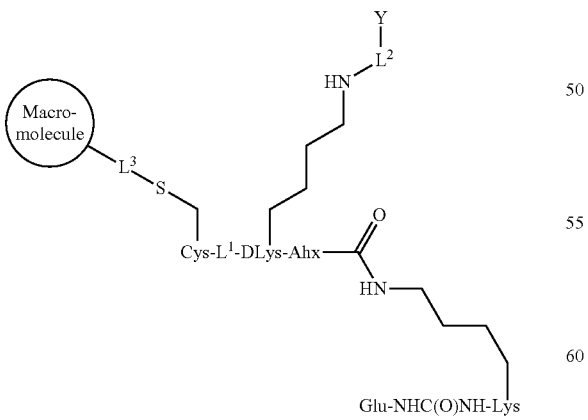

wherein:

$L^1$ is a peptidic fragment comprising from 1 to about 10 natural or unnatural amino acid residues, or an optionally substituted, bivalent, $C_{1-20}$ saturated or unsaturated, straight or branched, hydrocarbon chain, wherein one or more methylene units of the hydrocarbon chain are optionally and independently replaced by —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;

$L^2$ is an optionally substituted, bivalent, $C_{1-10}$ saturated or unsaturated, straight or branched, hydrocarbon chain, wherein one or more methylene units of the hydrocarbon chain are optionally and independently replaced by -Cy-, —CHOH—, —NR—, —N(R)C(O)—, —C(O)N(R)—, —N(R)SO$_2$—, —SO$_2$N(R)—, —O—, —C(O)—, —OC(O)—, —C(O)O—, —S—, —SO—, —SO$_2$—, —C(=S)—, or —C(=NR)—;

$L^3$ is a covalent bond, or a crosslinker derived from a bifunctional crosslinking reagent, that conjugates a sulfhydryl of the (PSMAi)/chelator construct to a reactive moiety of the macromolecule, each -Cy- is independently an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

Y is a chelator moiety; and

R is hydrogen, $C_{1-6}$ alkyl, or a nitrogen protecting group;

wherein each amino acid residue, unless otherwise indicated, may be protected or unprotected on its terminus and/or side chain group.

2. The composition of claim 1, wherein $L^1$ is a peptidic fragment comprising 1, 2, 3, 4, or 5 natural or unnatural amino acid residues.

3. The composition of claim 1, wherein $L^1$ comprises one or two units of 6-aminohexanoic acid (Ahx).

4. The composition of claim 3, wherein $L^1$ is -Ahx-Ahx-.

5. The composition of claim 1, wherein $L^1$ is a $C_{1-10}$ saturated or unsaturated, straight or branched, hydrocarbon chain, wherein one or more methylene units of the hydrocarbon chain are optionally and independently replaced by —NR—, —O—, or —C(O)—.

6. The composition of claim 1, wherein $L^1$ comprises one or more units of —(CH$_2$CH$_2$O)— or —(OCH$_2$CH$_2$)—.

7. The composition of claim 1, wherein $L^2$ is a $C_{1-3}$ saturated or unsaturated, straight or branched, hydrocarbon chain, wherein one or more methylene units of the hydrocarbon chain are optionally and independently replaced by -Cy-, —NR—, —N(R)C(O)—, —C(O)N(R)—, —O—, —C(O)—, —OC(O)—, —C(O)O—, or —C(=S)—.

8. The composition of claim 7, wherein $L^2$ is a $C_{1-3}$ saturated or unsaturated, straight or branched, hydrocarbon chain, wherein one, two, or three methylene units of the hydrocarbon chain are optionally and independently replaced by -Cy-, —NR—, —C(O)—, or —C(=S)—.

9. The composition of claim 7, wherein -Cy- is phenylene.

10. The composition of claim 7, wherein $L^2$ is —C(O)—, —C(O)NH-phenylene, or —C(=S)NH-phenylene.

11. The composition of claim 1, wherein the chelator moiety is DOTA.

12. The composition of claim 1, wherein the chelator moiety is NOTA.

13. The composition of claim 1, wherein $L^3$ is a cross-linker derived from a bifunctional crosslinking reagent that conjugates a sulfhydryl of the (PSMAi)/chelator construct to a reactive moiety of the macromolecule.

14. The composition of claim 1, wherein the bifunctional crosslinking reagent is a maleimide or haloacetyl.

15. The composition of claim 1, wherein the bifunctional crosslinking reagent is a maleimide.

16. The composition of claim 1, wherein the macromolecule is a nanoparticle.

17. The composition of claim 1, wherein the macromolecule has a diameter no greater than 20 nm.

18. The composition of claim 1, wherein the macromolecule comprises:

a fluorescent silica-based nanoparticle comprising:
a silica-based core;
a fluorescent compound within the core;
a silica shell surrounding a portion of the core; and
an organic polymer attached to the nanoparticle, thereby coating the nanoparticle, wherein the nanoparticle has a diameter no greater than 20 nm.

19. The composition of claim 1, wherein from 1 to 100 PSMAi ligands are attached to the macromolecule.

20. The composition of claim 1, further comprising a radiolabel.

21. The composition of claim 1, wherein the chelator moiety comprises a member selected from the group consisting of N,N'-Bis(2-hydroxy-5-(carboxyethyl)-benzyl)ethylenediamine-N,N'-diacetic acid (HBED-CC), 1,4,7,10-tetraazacyclododecane-1,4,7,10-tetraacetic acid (DOTA), 1,4,7-triazacyclononane-N,N',N''-triacetic acid (NOTA), diethylenetriaminepentaacetic (DTPA), desferrioxamine (DFO), and triethylenetetramine (TETA).

22. A composition comprising a prostate specific membrane antigen inhibitor (PSMAi)/chelator construct covalently attached to a macromolecule, wherein the construct has the structure:

23. A method of making the composition of claim 1, the method comprising:

loading an orthogonally protected lysine building block comprising a suitable protecting group on a resin;

removing the suitable protecting group from the orthogonally protected lysine building block to produce a first compound on the resin;

contacting a protected glutamic acid with suitable reagents to produce a glutamic isocyanate building block; and contacting the glutamic isocyanate building block with a free α amino group of the first compound to yield a second compound comprising a fully protected urea on the resin.

24. The composition of claim 1, wherein the construct has the structure:

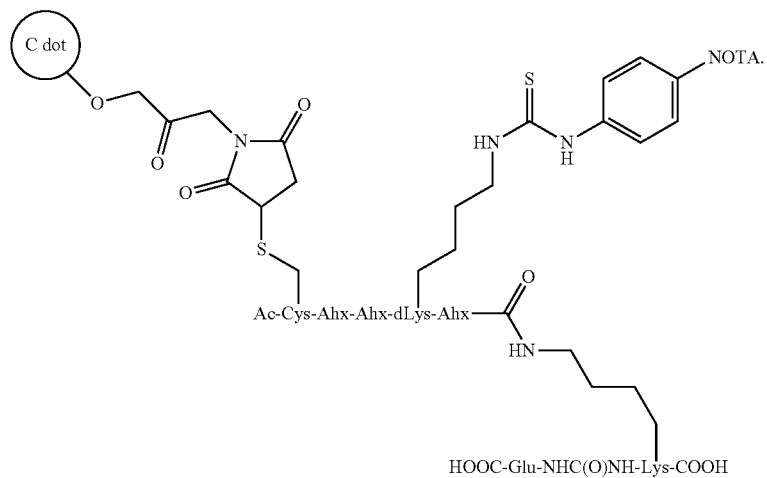
25. The composition of claim 1, wherein the construct has the structure:
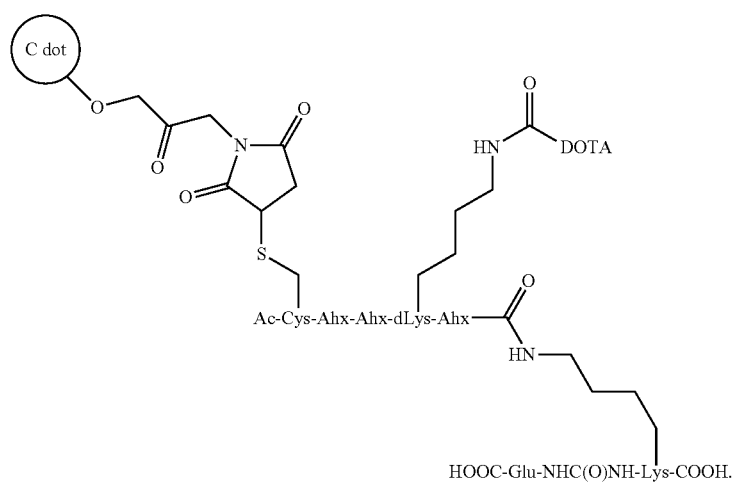
* * * * *